(12) United States Patent
Mihranyan

(10) Patent No.: US 11,278,563 B2
(45) Date of Patent: Mar. 22, 2022

(54) RAPID RELEASE PHARMACEUTICAL FORMULATIONS CONTAINING ALGAL CELLULOSE

(71) Applicant: Albert Mihranyan, Uppsala (SE)

(72) Inventor: Albert Mihranyan, Uppsala (SE)

( * ) Notice: Subject to any disclaimer, the term of this patent is extended or adjusted under 35 U.S.C. 154(b) by 0 days.

(21) Appl. No.: 16/077,044

(22) PCT Filed: Feb. 10, 2017

(86) PCT No.: PCT/GB2017/050345
§ 371 (c)(1),
(2) Date: Aug. 9, 2018

(87) PCT Pub. No.: WO2017/137762
PCT Pub. Date: Aug. 17, 2017

(65) Prior Publication Data
US 2019/0038661 A1  Feb. 7, 2019

(30) Foreign Application Priority Data
Feb. 12, 2016  (GB) .................................... 1602579

(51) Int. Cl.
| | |
|---|---|
| A61K 31/717 | (2006.01) |
| A61K 31/192 | (2006.01) |
| A61K 9/14 | (2006.01) |
| A61K 31/405 | (2006.01) |
| A61K 31/565 | (2006.01) |
| A61K 31/5415 | (2006.01) |
| A61K 31/196 | (2006.01) |
| A61K 9/16 | (2006.01) |
| A61P 29/00 | (2006.01) |
| A61K 31/166 | (2006.01) |
| A61K 31/57 | (2006.01) |

(52) U.S. Cl.
CPC ............ *A61K 31/717* (2013.01); *A61K 9/146* (2013.01); *A61K 9/16* (2013.01); *A61K 31/192* (2013.01); *A61K 31/196* (2013.01); *A61K 31/405* (2013.01); *A61K 31/5415* (2013.01); *A61K 31/565* (2013.01); *A61K 31/166* (2013.01); *A61K 31/57* (2013.01); *A61K 2300/00* (2013.01); *A61P 29/00* (2018.01)

(58) Field of Classification Search
CPC ............................... A61K 9/146; A61K 31/717
See application file for complete search history.

(56) References Cited

U.S. PATENT DOCUMENTS

| | | |
|---|---|---|
| 2005/0053665 A1 | 3/2005 | Ek et al. |
| 2007/0021499 A1 | 1/2007 | Dancer et al. |
| 2012/0295988 A1 | 11/2012 | Babcock et al. |

FOREIGN PATENT DOCUMENTS

| | | |
|---|---|---|
| EP | 2 135 601 | 12/2009 |
| JP | H0970424 | 3/1997 |
| WO | WO 00/56726 | 9/2000 |
| WO | WO 2006/061716 | 6/2006 |

OTHER PUBLICATIONS

Carlsson, D. et al., International Journal of Pharmaceutics, "Aspirin degradation in surface-charged TEMPO-oxidized mesoporous crystalline nanocellulose", 2014, vol. 461, pp. 74-81; available online Nov. 2013 (Year: 2013).*
Carlsson D. et al., International Journal of Pharmaceutics, "Aspirin degradation in surface-charged TEMPO-oxidized mesoporous crystalline nanocellulose", 2014, vol. 461, pp. 74-81 (Year: 2014).*
Tozuka, Y. et al., Chem Pharm. Bull., "Effect of Pore Size of FSM-16 on the Entrapment of Flurbiprofen in Mesoporous Structures", 2005, vol. 53, No. 8, pp. 974-977 (Year: 2005).*
Koyama, M. et al., Cellulose, "Systematic survey on crystalline features of algal celluloses", 1997, vol. 4, p. 147-160 (Year: 1997).*
Ali, Ahmed Shaker. et al. "Molecular behavior of flufenamic acid in physical and ground mixtures with fiorite." *Chemical and Pharmaceutical Bulletin* 40.5 (1992): 1289-1294.
Amidon, Gordon L., et al. "A theoretical basis for a biopharmaceutic drug classification: the correlation of in vitro drug product dissolution and in vivo bioavailability." *Pharmaceutical Research* 12.3 (1995): 413-420.
Carlsson, Daniel O., et al. "Susceptibility of Iα-and Iβ-dominated cellulose to TEMPO-mediated oxidation." *Biomacromolecules* 16.5 (2015): 1643-1649.
Carlsson Daniel O., et al. "Aspirin degradation in surface-charged TEMPO-oxidized mesoporous crystalline nanocellulose." *International Journal of Pharmaceutics* 461.1-2 (2014): 74-81.
Crowley, Michael M., et al. "Pharmaceutical applications of hot-melt extrusion: part I." *Drug Development and Industrial Pharmacy* 33.9 (2007): 909-926.
Dawood, M. Yusoff. "Nonsteroidal anti-inflammatory drugs and changing attitudes toward dysmenorrhea." *The American Journal of Medicine* 84.5 (1988): 23-29.
Diener et al., "Current diagnosis and treatment of migraine", *Der Schmerz*, 2008, 22 (Suppl. 1), 51-58. English Abstract.
Dion, Max, et al. "Van der Waals density functional for general geometries." *Physical Review Letters* 92.24 (2004): 246401.
Ek, Ragnar, et al. "Cellulose powder from *Cladophora* sp. algae." *Journal of Molecular Recognition: An Interdisciplinary Journal* 11.1-6 (1998): 263-265.
Gao, Jiali, et al. "Self-Assembly of Nanocellulose and Indomethacin into Hierarchically Ordered Structures with High Encapsulation Efficiency for Sustained Release Applications." *ChemPlusChem* 79.5 (2014): 725-731.

(Continued)

*Primary Examiner* — Bahar Craigo
(74) *Attorney, Agent, or Firm* — Parker Highlander PLLC

(57) ABSTRACT

There is provided a pharmaceutical composition comprising cellulose obtained from algae, or a derivative of said cellulose, and an active pharmaceutical ingredient (e.g. from Type 2 and 4 BCS class), wherein the active pharmaceutical ingredient is in a predominantly amorphous form. Compositions of the invention find particularly utility as formulations comprising BCS Type 2 and 4 drugs, including NSAIDs or other drugs, that may be employed in the treatment of migraine or dysmenorrhea, as well as formulations comprising other poorly soluble active ingredients where rapid release in vivo is advantageous.

16 Claims, 23 Drawing Sheets

(56) References Cited

OTHER PUBLICATIONS

Gustafsson, Christina, et al. "Evaluation of surface and bulk characteristics of cellulose I powders in relation to compaction behavior and tablet properties." *Drug Development and Industrial Pharmacy* 29.10 (2003): 1095-1107.
Hawkey. C. J. "COX-2 inbibitors." *The lancet* 353.9149 (1999): 307-314.
International Search Report for PCT/GB2017/050345 dated May 31, 2017.
Jabeen Saima, et al., "Raman and IR spectroscopic studies of fenamates—Conformational differences in polymorphs of flufenamic acid, mefenamic acid and tolfenamic acid." *Spectrochimica Acta Part A: Molecular and Biomolecular Spectroscopy* 96 (2.012): 972-985.
Kaufman, David W., et al. "Recent patterns of medication use in the ambulatory adult population of the United States: the Slone survey." *Jama* 287.3 (2002): 337-344.
Kimura. Minoru, et al. "Mesoporous structures in never-dried softwood cellulose fibers investigated by nitrogen adsorption." *Cellulose* 21.5 (2014): 3193-3201.
Kolakovic, Ruzica, et al. "Evaluation of drag interactions with nanofibrillar cellulose." *European Journal of Pharmaceutics and Biopharmaceutics* 85.3 (2013): 1238-1244.
Kolakovic, Ruzica, el al. "Spray-dried nanofibrillar cellulose microparticles for sustained drug release." *International Journal of Pharmaceutics* 430.1-2 (2012): 47-55.
Konno, Tsutomu, Koji Kinuno, and Katsuo Kataoka. "Physical and chemical changes of medicinals in mixtures with adsorbents in the solid state. I.: Effect of vapor pressure of the medicinals on changes in crystalline properties." *Chemical and Pharmaceutical Bulletin* 34.1 (1986): 301-307.
Konno, Tsutomu, and Koji Kinuno. "Physical and Chemical Changes of Medicinals in Mixtures with Adsorbents in the Solid State. II.: Application of Reduced Pressure Treatment for the Improvement of Dissolution of Flufenamic Acid." *Chemical and Pharmaceutical Bulletin* 37.9 (1989): 2481-2484.
Konno, Tsutomu. "Physical and Chemical Changes of Medicinals in Mixtures with Adsorbents in the Solid State. III.: Determination of Vapor Pressure of Solid Drugs by Steam Distillation." *Chemical and Pharmaceutical Bulletin* 38.4 (1990): 1032-1034.
Konno, Tsutomu. "Physical and Chemical Changes of Medicinals in Mixtures with Adsorbents in the Solid State. IV.: Study on Reduced-Pressure Mixing for Practical Use of Amorphous Mixtures of Flufenamic Acid," *Chemical and Pharmaceutical Bulletin* 38.7 (1990): 2003-2007.
Lindenberg, Marc, Sabine Kopp, and Jennifer B. Dressman. "Classification of orally administered drugs on the World Health Organization Model list of Essential Medicines according to the biopharmaceutics classification system." *European Journal of Pharmaceutics and Biopharmaceutics* 58.2 (2004): 265-278.
Livshits, Anna, and Daniel S. Seidman. "Role of non-steroidal anti-inflammatory drugs in gynecology." *Pharmaceuticals* 3.7 (2010): 2082-2089.
López-Mejías, Vilmalí, Jeff W. Kampf, and Adam J. Matzger. "Nonamorphism in flufenamic acid and a new record for a polymorphic compound with solved structures." *Journal of the American Chemical Society* 134.24 (2012): 9872-9875.
Matsumoto, K. "Aspirin hydrolysis in mixtures with porous crystalline cellulose." *Drug Stability* 1 (1996): 92-97.
Matsumoto, Kazuhiro, et al. "Effect of pore size on the gaseous adsorption of ethenzamide on porous crystalline cellulose and the physicochemical stability of ethenzamide after storage." *Chemical and Pharmaceutical Bulletin* 46.2 (1998): 314-318.
Matsumoto, et al. "Physicochemical characteristics of porous crystalline cellulose and formation of an amorphous state of ethenzamide by mixing." *International Journal of Pharmaceutics* 108.3 (1994): 167-172.

Mihranyan, Albert. "Cellulose from cladophorales green algae: From environmental problem to high-tech composite materials." *Journal of Applied Polymer Science* 119.4 (2011): 2449-2460.
Mihranyan, A., Maria Strömme, and R. Ek. "Influence of cellulose powder structure on moisture-induced degradation of acetylsalicylic acid." *European Journal of Pharmaceutical Sciences* 27.2-3 (2006): 220-225.
Mihranyan, Albert, et al. "Moisture sorption by cellulose powders of varying crystallinity." *International Journal of Pharmaceutics* 269.2 (2004): 433-442.
Mihranyan, Albert, et al. "Influence of the nanocellulose raw material characteristics on the electrochemical and mechanical properties of conductive paper electrodes." *Journal of Materials Science* 47.10 (2012): 4463-4472.
Mohanta, Vaishakhi, Giridhar Madras, and Satish Patil. "Layer-by-layer assembled thin films and microcapsules of nanocrystalline cellulose for hydrophobic drug delivery." *ACS Applied Materials & Interfaces* 6.22 (2014): 20093-20101.
Moser, Peter, Alfred Sallmann, and Irmgard Wiesenberg. "Synthesis and quantitative structure-activity relationships of diclofenac analogs." *Journal of Medicinal Chemistry* 33.9 (1990): 2358-2368.
Nagata, Kazunori, Hirokazu Okamoto, and Kazumi Danjo. "Naproxen particle design using porous starch." *Drug Development and Industrial Pharmacy* 27.4 (2001): 287-296.
Nakai, Yoshinobu, et al. "Effect of Grinding on Physical and Chemical Properties of Crystalline Medicinals with Microcrystalline Cellulose. II.: Retention of Volatile Medicinals in Ground Mixture." *Chemical and Pharmaceutical Bulletin* 26.10 (1978): 2983-2989.
Nakai, Yoshinobu, et al. "Interaction of medicinals and porous powder. I. Anomalous thermal behavior of porous glass mixtures." *Chemical and Pharmaceutical Bulletin* 32.11 (1984): 4566-4571.
Nakai, Yoshinobu, Keiji Yamamoto, and Satoshi Izumikawa. "Interaction of Medicinals and Porous Powder. III.: Effects of Pore Diameter of Porous Glass Powder on Crystalline Properties." *Chemical and Pharmaceutical Bulletin* 37.2 (1989): 435-438.
Nakai, Y., et al. "Interaction of Medicinals and Porous Powder. 2. Sublimation of Benzoic-Acid From Mixture With Porous-Glass Powder." *Yakugaku Zasshi-Journal of the Pharmaceutical Society of Japan* 105.3 (1985): 296-299.
Nakai, Yoshinobu. "Molecular behavior of medicinals in ground mixtures with microcrystalline cellulose and cyclodextrins." *Drug Development and Industrial Pharmacy* 12.7 (1986): 1017-1039.
Nicolai, E., and Reginald Dawson Preston. "Cell-wall studies in the Chlorphyceae. I. A general survey of submicroscopic structure in filamentous species." *Proceedings of the Royal Society of London. Series B-Biological Sciences* 140.899 (1952): 244-274.
Oguchi, Toshio, et al. "Freeze-Drying of Drug-Additive Binary Systems. II.: Relationship between Decarboxylation Behavior and Molecular States of p-Aminosalicylic Acid." *Chemical and Pharmaceutical Bulletin* 37.11 (1989): 3088-3091.
Oguchi, Toshio, et al. "Dissolution studies in organic solvents for evaluating hydrogen-bond matrix of cellulose in the ground mixture." *International Journal of Pharmaceutics* 113.1 (1995): 97-102.
Oguchi, Toshio, et al. "Improved dissolution of naproxen from solid dispersions with porous additives." *Journal of Pharmaceutical Science and Technology*, Japan 57.3 (1997): 168-173.
Pham-The, Hai, et al. "Provisional classification and in silico study of biopharmaceutical system based on caco-2 cell permeability and dose number." *Molecular Pharmaceutics* 10.6 (2013): 2445-2461.
Qian, Ken K., et al. "Characterization of medicinal compounds confined in porous media by neutron vibrational spectroscopy and first-principles calculations: a case study with ibuprofen." *Pharmaceutical Research* 29.9 (2012): 2432-2444.
Qian, Ken K., Dale E. Wurster, and Robin H. Bogner. "Spontaneous crystalline-to-amorphous phase transformation of organic or medicinal compounds in the presence of porous media, part 3: effect of moisture." *Pharmaceutical Research* 29.10 (2012): 2698-2709.
Román-Pérez, Guillermo, and José M. Soler. "Efficient implementation of a van der Waals density functional: application to double-wall carbon nanotubes." *Physical Review Letters* 103.9 (2009): 096102.

(56) References Cited

OTHER PUBLICATIONS

Shah, Sejal, et al. "Melt extrusion with poorly soluble drugs." *International Journal of Pharmaceutics* 453.1 (2013): 233-252.

Shinkuma, Denji, et al. "Correlation between dissolution rate and bioavailability of different commercial mefenamic acid capsules." *International Journal of Pharmaceutics* 21.2 (1984): 187-200.

Soler, José M., et al. "The SIESTA method for ab initio order-N materials simulation." *Journal of Physics: Condensed Matter* 14.11 (2002): 2745.

Strickley, Robert G. "Solubilizing excipients in pharmaceutical formulations." *Encyclopedia of Pharmaceutical Science and Technology, Six Volume Set (Print)*. CRC Press, 2013. 3207-3235.

Strømme, Maria, Albert Mihranyan, and Ragnar Ek. "What to do with all these algae?." *Materials Letters* 57.3 (2002): 569-572.

Svensson, Anna, et al. "Preparation of dry ultra-porous cellulosic fibres: Characterization and possible initial uses." *Carbohydrate Polymers* 92.1 (2013): 775-783.

Takagi, Toshihide, et al. "A provisional biopharmaceutical classification of the top 200 oral drug products in the United States, Great Britain, Spain, and Japan." *Molecular Pharmaceutics* 3.6 (2006): 631-643.

Tozuka, Yuichi, et al. "Molecular states of 2-naphthoic acid in solid dispersions with porous crystalline cellulose, as investigated by fluorescence spectroscopy." *Bulletin of the Chemical Society of Japan* 73.7 (2000): 1567-1572.

Tozuka, Yuichi, et al. "Fluorometric studies of pyrene adsorption on porous crystalline cellulose." *Journal of Colloid and Interface Science* 205.2 (1998): 510-515.

Tozuka, Yuichi, et al. "Solid-state fluorescence study of naphthalene adsorption on porous material." *Journal of Colloid and Interface Science* 248.2 (2002): 239-243.

Tozuka, Y., et al. "Adsorption state of naphthoic acids on folded sheets mesoporous materials with different pore sizes." *Journal of Drug Delivery Science and Technology* 19.6 (2009): 401-404.

Williams, Adrian C., et al. "Disorder and dissolution enhancement: Deposition of ibuprofen on to insoluble polymers." *European Journal of Pharmaceutical Sciences* 26.3-4 (2005): 288-294.

Yamamoto, Keiji, Waree Limwikrant, and Kunikazu Moribe. "Analysis of molecular interactions in solid dosage forms; challenge to molecular pharmaceutics." *Chemical and Pharmaceutical Bulletin* 59.2 (2011): 147-154.

Ylikorkala, Olavi. "Prostaglandin synthesis inhibitors in menorrhagia, intrauterine contraceptive device-induced side effects and endometriosis." *Pharmacology & Toxicology* 75 (1994): 86-88.

Yonemochi et al., "Encyclopedia of Surface and Colloid Science", vol. 6, 5068-5077, Somasundaran (ed), Taylor & Francis, 2nd edition (1986).

Yonemochi, Etsuo, et al. "Acceleration of the addition reaction of succinic anhydride and p-nitroaniline in controlled-pore glass solid dispersions." *Chemical and Pharmaceutical Bulletin* 37.11 (1989): 3083-3087.

Yonemochi, Etsuo, et al. "Diffusion and reaction of p-nitroaniline and succinic anhydride in controlled pore glass." *Chemical and Pharmaceutical Bulletin* 39.4 (1991): 1023-1026.

Yonemochi, Etsuo, et al. "Thermal behavior of methyl p-hydroxybenzoate in controlled-pore glass solid dispersion." *Journal of Colloid and Interface Science* 173.1 (1995): 186-191.

Ajayan, Pulickel M. "Capillarity-induced filling of carbon nanotubes." *Nature* 361.6410 (1993): 333-334.

Alcoutlabi, Mataz, and Gregory B. McKenna. "Effects of confinement on material behaviour at the nanometre size scale." *Journal of Physics: Condensed Matter* 17.15 (2005): R461.

Jackson, Catheryn L., and Gregory B. McKenna. "Vitrification and crystallization of organic liquids confined to nanoscale pores." *Chemistry of Materials* 8.8 (1996): 2128-2137.

Lombardo, Salvatore, et al. "Toward improved understanding of the interactions between poorly soluble drugs and cellulose nanofibers." *Langmuir* 34.19 (2018): 5464-5473.

Mantas, Athanasios, and Albert Mihranyan. "Immediate-release nifedipine binary dry powder mixtures with nanocellulose featuring enhanced solubility and dissolution rate." *Pharmaceutics* 11.1 (2019): 37.

Mantas, Athanasios, et al. "Amorphisation of Free Acid Ibuprofen and Other Profens in Mixtures with Nanocellulose: Dry Powder Formulation Strategy for Enhanced Solubility." *Pharmaceutics* 11.2 (2019): 68.

Prasad, By R., and S. Lele. "Stabilization of the amorphous phase inside carbon nanotubes: solidification in a constrained geometry." *Philosophical magazine letters* 70.6 (1994): 357-361.

Rengarajan, G. T., et al. "Stabilization of the amorphous state of pharmaceuticals in nanopores." *Journal of Materials Chemistry* 18.22 (2008): 2537-2539.

\* cited by examiner

RAPID RELEASE PHARMACEUTICAL FORMULATIONS CONTAINING ALGAL CELLULOSE

This application is a national phase application under 35 U.S.C. § 371 of International Application No. PCT/GB2017/050345, filed Feb. 10, 2017, which claims priority to United Kingdom Patent Application No. 1602579.3 filed Feb. 12, 2016. The entire text of each of the above referenced disclosures is specifically incorporated herein by reference.

FIELD OF THE INVENTION

This invention relates to new pharmaceutical compositions that provide for rapid release of active ingredients, such as Type 2 and 4 BCS drugs, featured with low solubility in the gastrointestinal tract. The invention also relates to methods of manufacturing such pharmaceutical compositions.

BACKGROUND

In order to provide the desired effect in the body, an orally taken drug needs to be absorbed from the gastrointestinal tract (GIT). The latter can only occur if the drug is dissolved first. Based on these considerations, a widely accepted Biopharmaceutics Classification System (BCS) was developed in 1995, in which all drugs can be divided in 4 general groups based on combination of two main criteria, viz. drug solubility and permeability (Amidon, G. L. et al. 1995. Pharm. Res. 12(3):413-420).

| Type 1 | Type 2 | Type 3 | Type 4 |
|---|---|---|---|
| High solubility High permeability | Low solubility High permeability | High solubility Low permeability | Low solubility Low permeability |

According to FDA BCS guidelines, the following boundaries are currently valid:

A drug substance is considered HIGHLY SOLUBLE when the highest dose strength is soluble in <250 ml water over a pH range of 1 to 7.5.

A drug substance is considered HIGHLY PERMEABLE when the extent of absorption in humans is determined to be >90% of an administered dose, based on mass-balance or in comparison to an intravenous reference dose.

A drug product is considered to be RAPIDLY DISSOLVING when >85% of the labeled amount of drug substance dissolves within 30 minutes using USP apparatus I or II in a volume of <900 ml buffer solutions.

Further, a dose number $D_0$ may also be useful as a solubility indicator:

$$D_0 = \frac{M_0}{V_0 \times S_{app}} \quad (1)$$

wherein $M_0$ is the maximum dose, $V_0$ is the volume available for dissolution, normally 250 ml, and $S_{app}$ is the apparent solubility of the drug in the medium. Thus, $D_0 < 1$ in a range of pH between 1 and 7.5 indicates good solubility, whereas if $D_0 > 1$ at any pH the solubility of a drug is poor.

Consequently, BCS Type 2 and 4 drugs are featured with low solubility and significant research and development has been devoted to enhance their bioavailability. The present invention pertains to enhancing the solubility and bioavailability of Type 2 and 4 BCS drugs. Formulations containing various APIs which are Type 2 or 4 BCS drugs are disclosed in Takagi et al. Mol. Pharm. 2006; 3(6): 631-643; Lindenberg et al. Eur. J. Pharm. Biopharm. 2004; 58: 265-278; and Pham The et al. Mol. Pharm. 2013; 10: 2445-2461. These references mainly deal with those on the WHO essential drugs list. However, the invention is useful also for developmental substances since it is known that at least more than half and as much as 90% of drug candidates are poorly soluble substances. In the context of the drug substances useful in the present invention, the molecular descriptors for typical BCS Type 2 and 4 substances can be used as summarized by Pham T. et al. Mol. Pharm. 2013; 10: 2445-2461, provided that they contain at least one aromatic ring or polycondensed cyclic structure.

TABLE 1

Typical molecular descriptors of various classes BCS drugs. Table adapted from Pham T. et al. Mol. Pharm. 2013; 10: 2445-2461.

| | Type 1 BCS | Type 2 BCS | Type 3 BCS | Type 4 BCS |
|---|---|---|---|---|
| Dose range, mg | 0.3-1000 | 10-800 | 0.25-1000 | 2-750 |
| Dose max mean/median, mg | 135.92/60 | 218.49/200 | 210.37/50 | 271.86/200 |
| Papp mean/median cm/s | 46.00/34.89 | 43.54/36.50 | 4.07/1.88 | 4.21/2.16 |
| Mw range | 135.23-479.58 | 169.57-1050.39 | 102.11-781.05 | 225.18/1202.84 |
| Mw mean/median | 290.50/289.41 | 340.39/318.23 | 349.48/348.82 | 499.56/425.96 |
| logP range | −0.97 to 5.20 | −4.61 to 5.70 | −5.50 to 4.63 | −0.32 to 5.10 |
| logP mean/median | 2.34/2.32 | 2.53/2.78 | 1.13/1.18 | 1.97/1.63 |
| logD pH6 range | −1.55 to 4.51 | −8.75 to 5.10 | −7.69 to 3.65 | −7.98 to 6.61 |
| logD pH6 mean/median | 0.71/0.65 | 1.81/1.9 | −0.88/−1.11 | 1.37/1.28 |
| logD pH7.5 range | −1.72 to 5.18 | −8.24 to 5.07 | −7.69 to 5.18 | −8.11 to 6.6 |
| logD pH7.5 mean/median | 1.34/1.18 | 1.63/1.67 | −0.56/−0.73 | 1.40/1.00 |

TABLE 1-continued

Typical molecular descriptors of various classes BCS drugs. Table adapted from Pham T. et al. Mol. Pharm. 2013; 10: 2445-2461.

|  | Type 1 BCS | Type 2 BCS | Type 3 BCS | Type 4 BCS |
|---|---|---|---|---|
| nHA + B range | 1-15 | 1-40 | 2-27 | 1-28 |
| nHA + B mean/median | 4.97/4 | 6.24/6 | 8.81/8 | 10.81/10 |
| RBN, range | 0-13 | 0-19 | 0-16 | 1-20 |
| RBN, mean/median | 4.12/4 | 4.34/4 | 5.07/4 | 7.56/7 |

RBN, rotating bonds number;
nHA + B total number of hydrogen bond acceptors and donors;
Papp apparent permeability;
logD pH dependent distribution coefficient in octanol-water;
logP partition coefficient in octanol-water;
Mw molecular weight Most of NSAIDs are normally Type 2 or 4 BCS substances with low solubility although some of them, such as salicylic acid derivatives e.g. ASA, salicylic acid, ethenzamide, etc, or acetaminophen, are classed as Type 1 (or Type 3) substances. NSAIDs are a practical model of poorly soluble drugs because they are affordable and have relatively low toxicity as compared to other pharmacological classes of drugs and therefore are less hazardous for research personnel and environment.

Over-the-counter (OTC) NSAIDs are the most frequently used individual medical products taken between 17 to 23% of the population (Kaufman D W, et al., 2002. JAMA, 287(3):337-344). More than thirty billion tablets are sold annually and tens of millions of people take NSAIDs every day. For ibuprofen alone, over one hundred billion tablets have been sold OTC in USA, since it became available for consumers in 1984.

Pharmacologically, NSAIDs act by interacting with the cyclooxygenase (COX) enzymes thereby inhibiting the arachidonic acid (AA) cascade production of prostaglandins (PGs), e.g. PGE2 and PGF2a, which play a key role in inflammation and pain.

NSAIDs mimic AA to be able to inhibit COX, i.e. (i) they contain a centre of acidity or a free carboxylic group and (ii) are largely lipophilic and feature at least one aromatic ring. Normally, NSAIDs have a centre of acidity, typically represented by a carboxylic acid group or alternatively by enolic group, hydroxamic acid, sulfonamide, or a tetrazole ring. The acidic group of NSAIDs is important for H-bonding with the polar region at Arg120 and oppositely located Tyr355 of COX (Hawkey 1999. Lancet 353:307-314). The presence of aromatic rings renders NSAIDs lipophilic. Except for a limited number of NSAIDs, such as aspirin, ethenzamide, or ibuprofen, the predominant majority of NSAIDs have 2 aromatic rings, which are capable of forming a twisted conformation relative to each other. It is believed that it is beneficial when the two rings are twisted relative to each other to a maximum degree (Moser, et al., 1990, J. Med. Chem., 33, 2358-2368). Thus, the lipophilicity of NSAID molecules is essential for inhibition of COX enzymes. Furthermore, it also ensures unhindered passive diffusion across biological membranes. The overall lipophilic character of NSAIDs results in poor solubility-limited bioavailability, i.e. Type 2 and 4 BCS drugs.

While NSAIDs are typically used as analgesics, antiinflammatory drugs and antipyretics, they can also be useful for treatment of primary dysmenorrhea and migraine.

Speed of absorption is crucial in the pharmacological treatment of certain conditions, such as migraine attacks and primary dysmenorrhea, since the fastest possible alleviation of symptoms is desired. Most NSAIDs have poor solubility and thereby poor bioavailability. They are typically administered in high doses (due, in part, to the low solubility/bioavailability) and the peak plasma concentration is reached usually in 2 hours.

The administration of high doses of NSAIDs in order to achieve a therapeutic effect is partly the reason for the side effects, such as gastric ulcers, associated with these drugs. Some 10% to 50% of patients are unable to tolerate treatment with NSAIDs because of side effects, including abdominal pain, diarrhoea, and upset stomach. Approximately 15% of patients on long-term treatment with NSAIDs develop a peptic ulcer (ulceration of the stomach or duodenum). Even though many of these patients with ulcers do not have symptoms and are unaware of their ulcers, they are at risk of developing serious ulcer complications such as bleeding or perforation of the stomach.

There is therefore a need to provide formulations containing NSAIDs, and other drugs, which are able to alleviate symptoms (of conditions such as migraine and dysmenorrhea) as rapidly as possible while minimising the risk of side effects for the patient.

Oral route of drug administration is the most frequently used and convenient route for administration of many drugs. Microcrystalline cellulose is an important tableting excipient for oral administration. European Pharmacopoiea defines microcrystalline cellulose (MCC) as purified, partially depolymerized cellulose, prepared by treating α-cellulose, obtained as a pulp from fibrous plant material, with mineral acids. Although the primary aim of treating α-cellulose with mineral acid to a so-called level-off degree of polymerization (DP 100-350) is to remove amorphous regions of cellulose, the overall degree of crystallinity of MCC does not exceed 80% as measured by XRD (Mihranyan et al. Int. J. Pharm. 2004; 269 (2), 433-442). Normally MCC is an essentially non-porous powder featuring a surface area around 0.5-1 $m^2/g$ as measured by nitrogen gas adsorption (ibid). MCC is normally produced by spray-drying of the cellulose slurry that is obtained following the acidic hydrolysis.

Oguchi T. et al., Yakuzaigaku, Vol. 57, No. 3 (1997) 168 discusses the use of a porous form of microcrystalline cellulose, referred to as "porous crystalline cellulose" PCC, as a drug carrier in a composition with naproxen. However, the manner in which the drug carrier is prepared is not disclosed. Here and throughout the text the term PCC refers solely to an undisclosed material supplied by Asahi Kasei, Japan. In the disclosed document, no details of PCC preparation method are presented.

Matsumoto K. et al., Chem. Pharm. Bull. 46(2) 314-318 (1998) discloses the use of PCC in mixtures with ethenzamide, i.e. a type 1(3) BCS substance. No details regarding the preparation of the excipient are provided. The material described therein displays poor stability in the presence of moisture as it progressively loses its specific surface area when exposed to various relative humidities.

Tozuka Y., et al. Bull. Chem. Soc. Jpn., 73, 1567-1572 (2000) discloses a composition of PCC with 2-naphthoic acid. However, very little information concerning the origin of the PCC is provided, and there is no mention of an improvement in the sensitivity of PCC to moisture.

Nakai Y. et al., Chem. Pharm. Bull. 26(10) 2983-2989 (1978) discloses compositions of MCC with naphthalene, camphor and o-cresol. Nakai Drug Dev. Ind. Pharm. 1986; 12(7): 1017-1039 discloses formulations containing ground MCC mixtures having enhanced solubility. It is clear from Nakai (1986) that the drugs are not stable in the formulations disclosed therein. Furthermore, it is evident from the XRD data that the structure of the MCC gradually changes resulting in the MCC becoming progressively more amorphous.

The listing or discussion of an apparently prior-published document in this specification should not necessarily be taken as an acknowledgement that the document is part of the state of the art or is common general knowledge.

DISCLOSURE OF THE INVENTION

According to the invention, there is provided a pharmaceutical composition comprising cellulose obtained from algae, or a derivative of said cellulose, and an active pharmaceutical ingredient, wherein the active pharmaceutical ingredient (e.g. a Type 2 or 4 BCS substance) is in a predominantly amorphous form. Compositions comprising such features are hereinafter referred to together as "the compositions of the invention".

We have advantageously found that compositions of the invention provide for rapid release of Type 2 and 4 BCS active ingredients and an enhancement of their bioavailability in the gastrointestinal tract (GIT) following peroral administration of the composition. In one embodiment, substantially all (e.g. at least about 85%) of the drug is released from the formulation in the first hour following administration of the formulation. The release may also be such that amount of drug released from the composition reaches a plateau within a short space of time (e.g. within about 1 hour, such as within about 15 minutes). That is, substantially all (e.g. at least about 90%) of the total amount of drug that is released during the first 24 hours may be released during the first hour (e.g. during the first 15 minutes). In the present application, the terms "rapid release" and "intermediate release" are used interchangeably. The compositions of the invention are not limited to oral administration, and can be delivered by other routes, as is discussed elsewhere herein.

The term "rapid release" will be understood by the skilled person to refer to compositions that provide, and/or are adapted to provide, for a "quick" and/or an "immediate" release of drug (in which drug is released at a sufficiently high rate for a sufficient period of time to produce a therapeutic response in a very short time) from the formulation. Release from the formulation refers to release of the drug from the network structure of the cellulose.

The compositions of the invention are also advantageous as they exhibit an increased physical stability of the active pharmaceutical ingredient (e.g. an increased stability of its physical form) within the formulation. In the compositions of the invention, the active pharmaceutical ingredient, which is typically a Type 2 or 4 BCS substance, is present in a predominantly amorphous form and the compositions allow the active pharmaceutical ingredient to remain in such a predominantly amorphous form for an extended period of time (e.g. up to at least 1 month, such as up to at least six months). Upon release from the cellulose carrier, the active pharmaceutical ingredient is provided in a form having a high degree of amorphicity compared to other formulations. This in turn enhances the rate of dissolution of the active pharmaceutical ingredient in surrounding media, and accelerates uptake by the body.

Enhanced dissolution is particularly important for Type 2 and 4 BCS active ingredients as these substances have a low solubility profile. By enhancing the dissolution rate of the active pharmaceutical ingredient following administration, the overall dose of drug that is provided to the subject may be reduced while still achieving the intended therapeutic benefits.

The compositions of the invention comprise cellulose obtained from one or more species of algae by hydrolysis with strong mineral acid. Said cellulose may be provided either in the form in which it is naturally produced, or as a derivative of such a form. Derivatives that may be mentioned in this respect are produced by surface limited modification of cellulose without its dissolution. The chemical routes of modification may include any of the known surface limited reactions involving primary and secondary alcohols such as but not limited to TEMPO-mediated oxidation, acylation, etherification, epoxylation, sulfonation, phosphorylation, and halogenation, e.g. chlorination, bromination, or iodination. Such derivatives may therefore include $C_{1-4}$ alkyl ether derivatives (such as methyl cellulose and ethyl cellulose), and $C_{1-4}$ acyl ester derivatives (such cellulose acetate, cellulose propionate and cellulose butyrate). Such derivatives are typically only present at the $2^{nd}$, $3^{rd}$ and $6^{th}$ carbon atoms of the D-glucose units. It is also preferred that, when the cellulose is provided in the form of a derivative, it is a surface modified cellulose. By this we mean that the cellulose has been modified primarily at only the exposed surfaces of the network structure rather than at every modifiable position on every D-glucose unit within the cellulose network. By limiting the modifications to only the surface regions, the large scale structure of the cellulose that is present prior to chemical modification can be preserved during and after chemical modification. For the avoidance of doubt, the surface- and bulk-modified celluloses can be discerned by their degree of crystallinity, i.e. the degree of crystallinity of surface modified cellulose will be essentially unaltered following chemical modification, whereas that of bulk modified cellulose will be significantly reduced, compared to the unmodified cellulose.

Cellulose is a natural polymer made from D-glucose units, which condense through $\beta(1\rightarrow4)$-glycosidic bonds. This linkage motif contrasts with that for $\alpha(1\rightarrow4)$-glycosidic bonds present in starch, glycogen, and other carbohydrates. Cellulose is a straight chain polymer: unlike starch, no coiling or branching occurs, and the polymer adopts an extended and rather stiff rod-like conformation, aided by the equatorial conformation of the glucose residues. The multiple hydroxyl groups on the glucose from one chain form hydrogen bonds with oxygen atoms on the same or on a neighbouring chain, holding the chains firmly together sideby-side and forming microfibrils with high tensile strength. This confers tensile strength in cell walls, where cellulose microfibrils are meshed into a polysaccharide matrix. MCC, which is produced by mineral acid hydrolysis of cellulose to a level-off degree of polymerisation (DP 100-350), is particularly useful as a pharmaceutical tableting aid.

Regardless of its source, native cellulose (or cellulose I) is a mixture of two allomorphs: cellulose Iα and cellulose Iβ. The triclinic Iα allomorph is predominant in algal-bacterial celluloses, whereas the cotton-ramie types of cellulose are rich in the Iβ allomorph. The distinctive properties of highly crystalline cellulose in XRD are the very well-resolved and narrow peaks, especially at 2θ values of 14 and 16°, which are not common for the native cellulose obtained from higher plants (Mihranyan, A. (2011), *J. Appl. Polym.* 119: 2449-2460). The detailed discussion on distinctive properties of cellulose allomorphs can be found e.g. in Carlsson et al. 2015. Biomacromolecules, 16(5): 1643-1649. Furthermore, the mineral acid hydrolysed highly crystalline algae cellulose features a degree of crystallinity (DP) that is much higher than the level-off DP of MCC. For comparison, Mihranyan et al. J Mater Sci (2012) 47:4463-4472 reports a DP of the order of ~1600 as measured via the viscosity of dissolved cellulose in Cuen reagent.

According to Nicolai and Preston (*Proc R Soc London Ser B* 1952, 140, 244) three groups of algae species can be classified according to their cell wall constituents. For the subject-matter of the present invention particularly useful are Group 1 algae which includes green algae in which native cellulose is the major component of the cell walls and which is usually highly crystalline. To these algae belong those of the Cladophorales (*Cladophora, Chaetomorpha, Rhizoclonium,* and *Microdyction*) and a few members of Siphonocladales (*Valonia, Dictyosphaeria, Siphonocladus,* and *Boergesenia*) orders.

The cellulose derived from marine green algae, for example, from *Valonia* or *Cladophora*, is featured with an exceptionally high degree of crystallinity. The degree of crystallinity may be around 95%, as obtained from XRD. The distinctive properties of highly crystalline cellulose in XRD are the very well-resolved and narrow peaks, especially at 2θ values of 14 and 16°, which are not common for the native cellulose obtained from higher plants (Mihranyan, A. (2011), *J. Appl. Polym. Sci.*, 119:2449-2460).

One process of obtaining the cellulose from the source algae typically resembles that of production of pharmaceutical grades of MCC (e.g. Avicel™ type) and, apart from bleaching and base extraction to liberate α-cellulose, also involves mineral acid hydrolysis of the algae as described e.g. in Mihranyan et al. Int. J. Pharm. 2004; 269 (2), 433-442. Methods are also disclosed in Ek, R., et al., Journal of Molecular Recognition, Vol. 11, 263-265 (1998). One skilled in the art will appreciate that pharmaceutical grades of native cellulose may additionally include powdered cellulose (e.g. of Arbocel™ type), which is not produced by acidic hydrolysis of α-cellulose, but rather by its comminution. However, MCC as a tabletting aid is preferrable to powdered cellulose.

Formulations containing microcrystalline cellulose (MCC) and "porous crystalline cellulose" (PCC) are disclosed in Tozuka Y., et al. *Bull. Chem. Soc. Jpn.*, 73, 1567-1572 (2000), and Nakai Y. et al., *Chem. Pharm. Bull.* 26(10) 2983-2989 (1978). While it is normally not described how exactly the MCC/PCC materials were produced, the cellulose materials used in those studies are derived from non-algal sources, based on the presented XRD profiles. The algal cellulose is particularly useful as it retains its large surface area even when exposed to several cycles of fluctuating humidity levels over the entire range between 0 and 100% relative humidity (RH). It is believed that the unusually high degree of crystallinity for algae cellulose provides the unusual rigidity to cellulose microfibrils which can withstand the capillary forces arising during drying when water is removed. Highly crystalline algae cellulose forms stronger tablets than MCC (Gustaffson et al. *Drug Dev. Ind. Pharm.* 2003; 29(10): 1095-1107; Strømme et al *Mat. Lett.* 2002; 57: 569-572).

Marine green algae, such as *Boergesenia, Cladophora,* and *Valonia,* contain broad microfibrils with a high degree of crystallinity, whereas wood cellulose has relatively high level of amorphous cellulose content. The cellulose microfibrils of algal origin are 10-30 nm in width as compared to microfibrils of cellulose derived from wood, which are 5 nm in width. PCC described by Matsumoto et al. *Chem. Pharm. Bull.* 46(2) 314-318 (1998) collapses into a non-porous structure, when exposed to fluctuating levels of humidity.

Thus, in the compositions of the invention, the cellulose or derivative thereof is obtained from algae. Preferably the algae is a "Group 1" algae as defined by Nicolai and Preston (*Proc R Soc London Ser B* 1952, 140, 244). That is, preferred algae include green algae in which native cellulose is the major component of the cell walls and which is usually highly crystalline. To these algae belong those of the Cladophorales (*Cladophora, Chaetomorpha, Rhizoclonium,* and *Microdyction*) and a few members of Siphonocladales (*Valonia, Dictyosphaeria, Siphonocladus,* and *Boergesenia*) orders.

In a preferred embodiment, the cellulose or derivative thereof is obtained from algae of the Cladophorales and Siphonocladales order. For example, the cellulose or derivative thereof may be obtained from algae of the genus *Cladophora, Chaetomorpha, Rhizoclonium,* or *Microdyction*. In a particularly preferred embodiment, the cellulose is obtained from algae of the genus *Cladophora*.

As is hereinbefore described, the cellulose derived from marine green algae, for example, from *Valonia* or *Cladophora*, is noted to have an exceptionally high degree of crystallinity. The degree of crystallinity may be around 95%, as obtained from XRD. The degree of cellulose crystallinity (CrI) from XRD is calculated according to the well known formula:

$$CrI = \frac{I_{22} - I_{18}}{I_{22}} \times 100 \qquad (2)$$

where $I_{22}$ is the overall intensity (i.e. the height) of the peak at 2θ about 22° and $I_{18}$ is the intensity of the amorphous background at 2θ about 18°.

The cellulose derived from marine green algae, for example, from *Valonia* or *Cladophora*, can be processed (e.g. via bleaching, α-cellulose extraction, acid hydrolysis, and/or spray-drying) to have a relatively high surface area, typically in the region of 100 $m^2/g$. This can be contrasted with microcrystalline cellulose which has a surface area of typically about 1 $m^2/g$. Celluloses which have a significantly lower surface area (e.g. below about 80 $m^2/g$) have generally been found to be much less capable of maintaining any adsorbed substances in an amorphous state.

Wood-derived cellulose that is conventionally used in pharmaceutical excipients generally contains a much lower degree of crystallinity (for example 80% crystallinity for PCC and MCC as measured by XRD; see Mihranyan et al.

Int. J. Pharm. 2004; 269 (2), 433-442). Thus, preferred celluloses and cellulose derivatives that may be mentioned includes those which are substantially crystalline. For example, celluloses and cellulose derivatives that may be mentioned includes those which are at least about 80% crystalline, such as at least about 90% crystalline. In particularly preferred embodiments, the celluloses or cellulose derivative is at least about 95% crystalline as measured by XRD.

The use of algae-derived cellulose in the compositions of the invention is also advantageous in that the compositions show improved long term storage characteristics, particularly under conditions of fluctuating humidity. The algae-derived cellulose is better able to withstand high levels of humidity and subsequent dewatering compared to many wood-derived celluloses. Exposure to humidity is known to cause certain wood-derived celluloses to undergo irreversible agglomeration upon dewatering which results in a decrease in the overall surface area to a much greater extent that is observed for algal-derived celluloses. When amorphous active substances are present within the cellulose microstructure, such changes can further lead to (re)crystallization of the active ingredient which is detrimental to the dissolution profile of the overall composition.

Further, algae-derived celluloses also tend to absorb much lower levels of moisture compared to other (e.g. wood-derived) celluloses. This may potentially be of benefit in retaining the drug in an amorphous state since water increases the overall molecular mobility and may act as a plasticizer.

The ability of algal-derived celluloses (or derivatives thereof) to form stable amorphous mixtures with an active pharmaceutical ingredient is an important advantage for these materials. The data in the examples show that test materials are physically stable for up to 6 months at room temperature and 40% relative humidity, as followed by X-ray diffraction analysis.

The compositions of the invention have both good physical and good chemical stability. Physical stability refers to stability to undesired solid-state transformations of the drug, the excipient, or both. Examples of solid-state transformations include collapse of cellulose porous structure, amorphous-crystalline transformations, and the formation of polymorphs. A stable amorphous composition is one in which the drug in the composition remains present in a predominantly amorphous state, e.g. ≥90% amorphous following long term storage (e.g. storage for at least 2 months under ambient conditions). Changes in amorphicity may be quantified using melting enthalpy data obtained in differential scanning calorimetry (DSC). Alternatively, this may be qualitatively verified by the absence of sharp peak in XRD which would otherwise be indicative of crystalline drug and/or its polymorph.

The WHO essential drugs list includes the following Type 2 and 4 BCS drug categories: antihelminthic, anticonvulsant, antiepileptic, antibacterial, antiulcerative, antihyperlipidemic, anticholelithogenic, antimanic, antimigraine, antiamebic, antiviral, diuretic, antihypertensive, antipsychotic, analgesic, antipyretic, anti-inflammatory, antihistaminic, gastroprokinetic, antidiabetic, antiasthmatic, antianginal, immunosuppressant, antiobesity, antiosteoporotic, antihyperlididemicm, antiandrogen, contraceptive, antidysmenoreic, antiparkinsonian, anticoagulant, anticancer, anticirrhosis (biliary), anxyolithic, sedative, antifungal. The compositions of the invention are particularly suited for use with these drugs.

The compositions of the invention are also particularly suited for use with drugs which are solid under ambient conditions (e.g. drugs which have a melting point of at least 25° C.). Such drugs would benefit from the increased ability that algal cellulose has for retaining the drug in a predominantly amorphous state.

In one embodiment, the composition of the invention contains an active pharmaceutical ingredient that is considered to have low solubility according to FDA BCS guidelines. For example, the active pharmaceutical ingredient may be one for which the highest dose strength is not completely soluble in 250 ml water over a pH range of 1 to 7.5.

In a preferred embodiment, the composition of the invention contains an active pharmaceutical ingredient that has a dose number ($D_0$) greater than 1 at all pH values.

Active ingredients that may be employed in compositions of the invention preferably include Type 2 or 4 BCS active pharmaceutical ingredients, including among others non-steroidal anti-inflammatory drugs (NSAIDs) as normally described in pharmacological literature. NSAIDs are particularly suited to the compositions of the present invention due to the enhanced bioavailability, rapid release characteristics and reduced administered dose that can be achieved when used in these compositions. Apart from their several pharmacological effects, NSAIDs are useful in the treatment of dysmenorrhea and migraine, and in both cases rapid delivery of the drug aids in alleviating symptoms quickly. NSAIDs are also frequently suited for the compositions of the present invention given the presence of one or more aromatic rings or polycondensed cyclic structures (fully or partially saturated) and one or more hydrogen bond donors/acceptors in the drug molecule structures.

To illustrate the inventive concept, compositions of the invention in which the active pharmaceutical ingredient is an NSAID are described in the examples. However, the invention is not limited to such drug compounds. For the avoidance of doubt, the compositions of the invention may contain any active pharmaceutical ingredient, and preferably contain at least one active pharmaceutical ingredient that is a Type 2 or 4 BCS active pharmaceutical ingredient which has the molecular features discussed above.

Other particular active ingredients that may be employed in compositions of the invention include steroids and cholates. Steroids, in particular corticosteroids, are mainly used to reduce inflammation and suppress the immune system. They are used to treat conditions such as asthma, allergic rhinitis and hay fever, urticarial (hives), atopic eczema, chronic obstructive pulmonary disease (COPD), painful and inflamed joints, muscles and tendons, lupus, inflammatory bowel disease (IBD) (including Crohn's disease and ulcerative colitis), giant cell arteritis, polymyalgia rheumatica, and multiple sclerosis (MS). Progesterone, a natural steroid sex hormone, and its analogues, such as estradiol (e.g. ethynyl estradiol), progestin or estrogen, are used in treatment of primary dysmenorrhea. Cholates (in particular cholic acid, deoxycholic acid, ursodeoxycholic acid) may be used in the treatment of bile acid synthesis disorders due to single enzyme defects and peroxisomal disorders (such as Zellweger syndrome). Ursodeoxycholic acid is used for treatment of primary biliary cirrhosis.

In embodiments of the invention in which the active pharmaceutical ingredient may be an NSAID, particularly preferred NSAIDs include propionic acid derivatives (such as alminoprofenb, benoxaprofen, carprofen, dexibuprofen, dexketoprofen, fenbufen, fenoprofen, flunoxaprofen, flurbiprofen, ibuprofen, ibuproxam, indoprofen, ketoprofen, loxoprofen, miroprofen, naproxen, oxaprozin, pirprofen, suprofen, tarenflurbil, tepoxalin, tiaprofenic acid, vedaprofen, and naproxcinod), acetic acid derivatives (such as aceclofenac, acemetacin, alclofenac, amfenac, bendazac, bromfenac, bumadizone, bufexamac, diclofenac, difenpiramide, etodolac, felbinac, fentiazac, indomethacin, indomethacin farnesil, ketorolac, lonazolac, oxametacin, proglumetacin, sulindac, tolmetin, zomepirac, and nabumetone), Oxicams (also referred to as "enolic acid derivatives"; such as ampiroxicam, droxicam, isoxicam, lornoxicam, meloxicam, piroxicam, tenoxicam, and phenylbutazone (bute)), anthranilic acid derivatives (so-called "fenamates"; such as azapropazoner, etofenamate, flufenamic acid, flunixin, meclofenamic acid, mefenamic acid, morniflumate, niflumic acid, and tolfenamic acid), selective COX-2 inhibitors (such as apricoxib, celecoxib, cimicoxib, deracoxib, etoricoxib, firocoxib, lumiracoxib, mavacoxib, parecoxib, robenacoxib, rofecoxib, and valdecoxib), pyrazolones and pyrazolidines (such as aminophenazone, ampyrone, azapropazone, clofezone, famprofazone, feprazone, kebuzone, metamizole, mofebutazone, morazone, nifenazone, oxyphenbutazone, phenazone, phenylbutazone, propyphenazone, sulfinpyrazone and suxibuzone), and sulfonanilides (such as nimesulide).

Particularly preferred NSAIDS include arylpropionic acid derivatives (e.g. ibuprofen, ketoprofen, flurbiprofen, and naproxen) anthranilic acid derivatives (e.g. flufenamic acid, mefenamic acid, and tolfenamic acid), acetic acid derivatives (e.g. indomethacin, and sulindac), and enolic acid derivatives (e.g. pyroxicam).

In embodiments of the invention in which the active pharmaceutical ingredient may be a steroid or a cholate, particularly preferred active pharmaceutical ingredients include a contraceptive such as progesterone, estradiol (e.g. ethynyl estradiol), progestin, estrogen, cholic acid, deoxycholic acid or ursodeoxycholic acid.

Active pharmaceutical ingredients that are particularly useful in the compositions of the invention include compounds which contain at least one aromatic ring or a polycondensed (fully or partially saturated) cyclic structure, optionally wherein the molecule also contains at least one hydrogen bond donor or hydrogen bond acceptor. Hydrogen bond donors include at least one XH moiety wherein X=C, N, O, or S (preferably wherein X=N or O). Hydrogen bond acceptors include oxygen and nitrogen atoms. Other active pharmaceutical ingredients that are particularly useful in the compositions of the invention include compounds which contain at least one aromatic ring or a polycondensed cyclic structure, and at least one hydrogen bond donor or hydrogen bond acceptor. Without wishing to be bound by theory, it is believed that such compounds are able to participate in hydrophobic interactions ($\pi$-XH interactions wherein X=C, N, O, S; and $\pi$-$\pi$ interactions) with large surface area hydroxyl-rich portions of the cellulose.

Results obtained from molecular modelling studies suggest that the rapid-release characteristics observed for the compositions containing ibuprofen or flufenamic acid in the Examples will similarly be observed for compositions of the invention containing other drug molecules which have at least one aromatic ring or a polycondensed (fully or partially saturated) cyclic structure, particularly where the drug molecule also contains at least one hydrogen bond donor or hydrogen bond acceptor.

The molecular modelling studies are summarised here. Interaction energies between aromatic organic molecules (AOM) and cellulose were probed using density functional theory (DFT) with respect to weak intermolecular interactions such as H-bonding, rr-rr stacking, and $\pi$-OH bonds.

Three model AOMs, viz. benzene, benzamide and benzoic acid, were used for ab initio simulations with cellulose using cellobiose as the structural monomer. No consideration to different cellulose allomorphs or cellulose crystal planes was taken. All pre-relaxation molecular coordinates were acquired from the PubChem Compounds Database. The Van der Waals exchange-correlation functional vdW-DF by Dion et al (Dion M. et al. (2004), Phys. Rev. Lett. 92, 246401) as implemented by Roman-Perez and Soler (Soler J M et al (2002) J. Phys. Condens. Matter 14, 2745-2779; Roman-Perez et al (2009) Phys. Rev. Lett. 103, 096102) was used.

The basis set was DZP and the energy cut-off was set at 300 Ry. The molecular systems were structurally relaxed using the iterative Conjugate Gradient (CG) method.

Results

TABLE 2 interaction energies of AOM dimers

| Molecular Configuration | | Energy of interaction (kcal/mol) |
| --- | --- | --- |
| Benzene | Sandwich | −2.6 (0.1) |
| | T-shaped | −1.3 (0.1) |
| | Displaced parallel | −2.1 (0.1) |
| Benzamide | Sandwich | −3.2 (0.1) |
| | Inverted sandwich | −3.4 (0.1) |
| | Co-axial (H-bond) | −6.7 (0.1) |
| Benzoic Acid | Sandwich | −3.1 (0.1) |
| | Inverted sandwich | −3.2 (0.1) |
| | Co-axial (H-bond) | −12.6 (0.2) |

TABLE 3 interaction energies of Cellulose-AOM complexes

| Molecular Configuration | | Energy of interaction (kcal/mol) |
| --- | --- | --- |
| Benzene | Core | −3.6 (0.7) |
| | $\pi$-OH primary | −2.5 (0.7) |
| | $\pi$-OH secondary | −4.7 (0.7) |
| Benzamide | Core | −4.8 (0.7) |
| | $\pi$-OH primary | −3.2 (0.7) |
| | $\pi$-OH secondary | −4.8 (0.7) |
| | H-bond-OH primary | −10.2 (0.7) |
| | H-bond-OH secondary | −8.0 (0.7) |
| Benzoic Acid | Core | −5.6 (0.7) |
| | $\pi$-OH primary | −4.4 (0.7) |
| | $\pi$-OH secondary | −8.4 (0.7) |
| | H-bond-OH primary | −11.2 (0.7) |
| | H-bond-OH secondary | −10.0 (0.7) |

It was found that the studied aromatic organic molecules are in general more likely to interact with cellulose than to form a dimer. Although H-bonding was particularly strong, the contribution of $\pi$-OH interactions was still significant. The results predict that there is a high affinity between cellulose and AOM and this affinity will be further amplified over the large surface area that cellulose may provide, wherein the interactions at a monolayer or close to a monolayer will be the strongest.

Particularly preferred BCS Type 2 and 4 APIs that may be mentioned in this respect include compounds which contain at least one aromatic ring (preferably at least two aromatic rings), and at least one hydrogen bond donor or hydrogen bond acceptor. Thus, a further embodiment relates to compositions of the invention containing at least one active pharmaceutical ingredient (e.g. an NSAID) having such structural features (i.e. at least one (e.g. at least two) aromatic ring, and at least one hydrogen bond donor or hydrogen bond acceptor). Particular NSAIDs that may be mentioned in this respect include arylpropionic acid derivatives (e.g. ibuprofen, ketoprofen, flurbiprofen, naproxen), anthranilic acid derivatives (e.g. flufenamic acid, mefenamic acid), acetic acid derivatives (e.g. indomethacin, sulindac), and enolic acid derivatives e.g. pyroxicam. Particular NSAIDs having at least two aromatic rings that may be mentioned in this respect include arylpropionic acid derivatives (e.g. ketoprofen, flurbiprofen, naproxen); anthranilic acid derivatives (e.g. flufenamic acid, mefenamic acid), acetic acid derivatives (e.g. indomethacin, sulindac), and enolic acid derivatives (e.g. pyroxicam).

Other classes of compounds that may be particularly suited to be formulated with algae cellulose include those which contain a free carboxylic acid group (typically together with the one (or preferably two) aromatic ring), or an amide.

The compositions of the present invention are particularly suited to the delivery of active pharmaceutical ingredients that are poorly soluble. Type 2 and 4 BCS class NSAIDs in particular are appropriate due to the inherently low solubility (in physiological media) that is typical for such compounds. Type 2 and 4 BCS class NSAIDs are also particularly suited because they typical have molecular structures which contain at least one (preferably at least two) aromatic rings and a heterocycle. A further common feature for COX-1 inhibiting NSAIDs is a free carboxylic acid group which provides hydrogen bonding capabilities (acting as both a hydrogen bond donor and an acceptor). COX-2 inhibitors, which normally contain two or more aromatic rings, are specifically designed so that they are void of free carboxylic acid group to enhance their specificity. A number of NSAIDs are Type 2 or 4 BCS drugs so their bioavailability is generally dictated by their solubility. In conventional formulations, a relatively high dose of the NSAID, especially COX-1 inhibitors, is required in order to alleviate the recipient's symptoms sufficiently quickly. Without the use of a high dose in the formulation, the poor solubility slows the rate at which the active pharmaceutical ingredient is able to be released from the formulation to be taken up by the patient. The use of high doses increases the risk of the occurrence of adverse side effects in a patient. The compositions of the invention have been found to give superior, rapid release of poorly soluble substances in physiological environments. Consequently, said compositions may be able to overcome the problems associated with poor solubility with the result that the compositions are useful for rapid delivery of pharmaceutically effective amounts of active ingredients without requiring large dosages.

It should be noted that the advantages that have been identified for the compounds of the present invention are not limited to the compositions containing NSAIDs. The advantages may be realised for any drug which has a relatively low solubility, i.e. Type 2 and 4 BCS drugs, and which is typically administered orally to patients and has desirable structural features which enable rr-rr and π-OH interactions. For the avoidance of doubt, the compositions of the invention may be administered by other routes, in particular transmucosally (such as via sublingual or buccal administration), or via rectal or vaginal administration.

Active ingredients may further be employed in salt form or any other suitable form, such as e.g. a complex, solvate or prodrug thereof, or, if relevant, in any stereoisomeric form including any enantiomeric, diastereomeric or racemic form, or a combination of any of the above.

Pharmaceutically-acceptable salts of active ingredients that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

In the compositions of the invention, the active pharmaceutical ingredient is present in a predominantly amorphous form. For example, the active pharmaceutical ingredient may be essentially amorphous (i.e. at least about 90% amorphous, that is at least about 90% by weight of the active pharmaceutical ingredient is present in an amorphous form). Preferably, the active pharmaceutical ingredient is at least about 95% amorphous, at least about 98% amorphous or preferably at least about 99% amorphous. The degree of amorphicity in the active pharmaceutical ingredient may be determined by e.g. DSC. Additionally, the XRD profile for a product which is in a predominantly amorphous form would be one in which sharp peaks associated with the crystalline product (i.e. the drug or its polymorphs in the compositions of the invention) are substantially absent. For example, for a composition in which the active pharmaceutical ingredient is present in a predominantly amorphous form, the degree of crystallinity of the active pharmaceutical ingredient may be found to be less than about 10%, when determined using DSC. Compositions in which the active pharmaceutical ingredient is present in a predominantly amorphous form may be qualitatively identified via their XRD profiles by virtue of the absence of sharp characteristic diffraction peaks typical for crystalline substances.

The change from a crystalline to an amorphous state can be monitored using a variety of techniques. For example, differential scanning calorimetry (DSC) measurements conducted on crystalline materials will show a melting endotherm, whilst amorphous materials generally will not exhibit any such endotherm. X-ray diffraction (XRD) analysis will also show characteristic sharp peaks of high intensity for crystalline materials whereas amorphous materials will typically yield a diffraction pattern that lacks any such sharp, high intensity peaks.

Infra-red absorption spectroscopy (e.g. FT-IR) can also show shifts in absorption frequencies indicating molecular rearrangement and interactions between API and excipient. Where the drug is a substance that contains an aromatic group and a carbonyl group (such groups are typically present in NSAIDs) the changes in the frequencies of the aromatic vibrations (between around 1000 and 800 cm$^{-1}$) and C=O vibrations (between around 1500 and 1800 cm$^{-1}$) will be indicative of significant molecular rearrangement. One skilled in the art will understand that shifts of other characteristic peaks for H-bond donors/acceptor groups may also be indicative of molecular rearrangement.

Prior to introduction to the composition, the active pharmaceutical ingredient may be provided in any form, including a form that is crystalline or substantially crystalline.

In a further embodiment, the weight ratio of the active pharmaceutical ingredient to the algal-derived cellulose in the composition of the invention is at most 1:3. For example, the weight ratio may be at most 1:5. In preferred embodiments, the weight ratio of the active pharmaceutical ingredient to the algal-derived cellulose in the composition is not more than 1:9. The use of a controlled amount of the active pharmaceutical ingredient in the composition of the invention is important as, without wishing to be bound by theory, it is believed that the interactions that occur between the active pharmaceutical ingredient and the cellulose component at the monolayer level are the strongest, and so the relative proportions should be chosen in order to maximise this effect.

Particularly preferred compositions of the invention include those in which the weight ratio of the active pharmaceutical ingredient to the algal-derived cellulose in the composition is not more than 1:3 (e.g. not more than 1:9), and the surface area of the algae-derived cellulose or derivative thereof is at least 60 m$^2$/g (e.g. at least about 100 m$^2$/g) as measured by N$_2$ gas adsorption technique according to the Brunauer Emmett Teller (BET) method.

Further preferred compositions of the invention include those in which the weight ratio of the active pharmaceutical ingredient to the algal-derived cellulose in the composition is not more than 1:3 (e.g. not more than 1:9), and the active pharmaceutical ingredient is at least about 90% amorphous.

Still further preferred compositions of the invention include those in which the weight ratio of the active pharmaceutical ingredient to the algal-derived cellulose in the composition is not more than 1:5 (e.g. not more than 1:9), and the active pharmaceutical ingredient is at least about 95% amorphous.

Still further preferred compositions of the invention include those in which the cellulose or derivative thereof is at least about 90% crystalline and the active pharmaceutical ingredient is at least about 90% amorphous.

Compositions of the invention may be prepared by way of a variety of routine techniques, and using standard equipment, known to the skilled person, including mixing together the active pharmaceutical ingredient and the cellulose obtained from algae, or the derivative thereof.

Typically the active pharmaceutical ingredient will be initially provided in a crystalline form. Amorphisation of the active pharmaceutical ingredient may be achieved through any technique which is capable of reducing the level of crystallinity of the active pharmaceutical ingredient in the composition without substantially degrading the cellulose component or altering adversely its physical structure. Suitable techniques include heat-assisted intensive mixing (e.g. melt extrusion), static heat sealing, intensive mixing, reduced pressure mixing, moderate heating, combined grinding and heating, and co-spray drying with a solvent.

Heat-assisted intensive mixing, for example melt extrusion, is particularly useful. During the heat-assisted mixing the components are heated while being mixed, while the heating temperature may be at or below the melting point of the active ingredient. An extruder equipped with heated compartments, e.g. similar to those used for melt extrusion, is particularly useful. For the compositions of the invention, the process involves the processing of a mixture containing the active pharmaceutical ingredient (optionally initially in a substantially crystalline form) and the algae-derived cellulose. A classical melt extrusion process is a process during which at least one component in the blend is melted (or at least heated to close to its melting point or above its glass transition temperature) and the mixture is formed into products of different shapes and sizes by forcing the components and active substances through an orifice or die under controlled temperature, pressure, feeding rate, and screw speed. Suitable melt extrusion techniques that will be known to the skilled person include those described in Shah S., et al., *Int. J. Pharm.*, 453 (2013) 233. Conventional melt extrusion techniques are typically used with thermoplastic polymers, i.e. polymers that melt before they degrade. In contrast, native cellulose, such as MCC or algae-cellulose, is a non-thermoplastic polymer, which degrades by pyrolysis before it melts. Nonetheless, melt extruders and other heat-assisted intensive mixers are particularly useful in the context of the present invention. Thus, these techniques can also be used with the non-thermoplastic cellulose-based systems of the present invention, e.g. using single- or twin-screw extruders, preferably with a heating unit as long as the temperature inside the mixture does not exceed that at which the cellulose degrades by pyrolysis. Thus, the temperature inside the mixture should not exceed about 350° C., and preferably should not exceed about 300° C.

It may also be possible to form compositions of the invention without extrusion by statically heating blends of pre-mixed active ingredient and algae-derived cellulose. The mixture is then heated to a temperature above its glass transition temperature for a sufficient period of time but below the degradation temperature of the cellulose such that the active pharmaceutical ingredient is substantially present in an amorphous form. In practice, the blends are heated in the range between 50 and 300° C.

Compositions of the invention may also be prepared by static heat sealing. In this process, mixtures of drug and cellulose are placed in a sealed vessel. The mixture is then heated to a temperature above the glass transition temperature of the active pharmaceutical ingredient for a sufficient period of time (the exact period to be determined empirically depending on the quantities of the used ingredients, e.g. between 5 min and 72 hours) such that the active pharmaceutical ingredient is substantially present in an amorphous form.

Thus a further aspect of the invention relates to a pharmaceutical composition comprising cellulose obtained from algae, or a derivative of said cellulose, and an active pharmaceutical ingredient, wherein the composition is obtained by a process involving heating a mixture of the active pharmaceutical ingredient and cellulose or cellulose derivative to a temperature close to or above the glass transition temperature of the active pharmaceutical ingredient. By "close to the glass transition temperature" in this context we mean that the heating temperature may be below the glass transition temperature by no more than 5° C. In practice, we mean that the mixture is heated to a temperature above about 50° C. The temperature should not exceed that at which degradation of the cellulose component would occur. Thus, typically in processes in which the cellulose component is heated in the presence of the active pharmaceutical ingredient, the temperature used should not exceed about 300° C.

Heat-assisted extrusion, including melt extrusion, is a particularly preferred technique for use in the context of the present invention. Thus, in one embodiment, the invention relates to a composition which is formed by a process involving heat-assisted extrusion of a mixture of the cellulose or cellulose derivative and the active pharmaceutical ingredient.

The mixing time period is likely to vary according to the equipment used, and the skilled person will have no difficulty in determining by routine experimentation a suitable mixing time for a given combination of ingredient(s) empirically.

Algae-derived celluloses and cellulose derivatives which have a high surface area (e.g. over at least 60 m$^2$/g, as measured by N$_2$ gas adsorption technique according to the Brunauer Emmett Teller (BET) method) are particularly preferred as these substances provide a high area of interaction with the active pharmaceutical ingredient. Strong interactions between the active pharmaceutical ingredient and the cellulose component help to improve the dissolution characteristics of the overall composition. The strength of the interactions is governed, at least in part, by the affinity between API and cellulose and further amplified over a large surface area. Strong interactions between cellulose and the active pharmaceutical ingredient can be observed in many ways, including FTIR spectroscopy or sometimes through colour changes associated with the active pharmaceutical ingredient itself, as well as through analysing the solid state fluorescence spectra of the mixture.

A preferred process for the formation of compositions of the invention involves the mixing together of an active pharmaceutical ingredient and an algal-derived cellulose or derivative thereof.

The product obtained by the above-mentioned process may further be adapted by: heat-assisted extrusion, e.g. melt-extrusion;
static heat sealing;
heat-assisted intensive mixing,
mixing under reduced pressure,
heating;
mild grinding (i.e. grinding which does not adversely affect the pore structure or the physical-chemical properties of the excipient); and/or
co-spray drying, or rotary evaporation at reduced pressure, with a solvent, preferably wherein the solvent is a mixture of water and lower alkyl alcohol;
using routine techniques in all cases.

Compositions of the invention may further comprise one or more further commonly-employed pharmaceutical excipients. Suitable excipients include inactive substances that are typically used as a diluent or carrier for the active ingredients in medications. Suitable excipients also include those that are employed in the pharmaceutical arts to bulk up pharmaceutical compositions that employ very potent active ingredients, to allow for convenient and accurate dosing. Alternatively, excipients may also be employed in manufacturing processes of the compositions of the invention to aid in the handling of the active ingredient concerned. One skilled in the art will understand that in pharmaceutical formulation other additives apart from diluent may be employed such as taste masking agents, glidants, superdisintegrants, coating agents, etc.

The compositions of the invention are preferably administered orally to the gastrointestinal tract and may provide for rapid release of the active pharmaceutical ingredient in the stomach and/or, preferably, the intestinal system.

In this respect, the compositions of the invention may be incorporated into various kinds of pharmaceutical preparations intended for oral administration using standard techniques (see, for example, Lachman et al, "*The Theory and Practice of Industrial Pharmacy*", Lea & Febiger, 3$^{rd}$ edition (1986) and "*Remington: The Science and Practice of Pharmacy*", Gennaro (ed.), Philadelphia College of Pharmacy & Sciences, 19$^{th}$ edition (1995)).

The compositions of the invention may also be administered to the patient through other routes, such as via transmucosal (e.g. sublingual or buccal), rectal or vaginal administration. An appropriate route of administration is one which allows for rapid uptake of the active pharmaceutical ingredient into the bloodstream following administration. Sublingual, buccal, rectal and vaginal routes of administration are suitable in this respect as they allow the active pharmaceutical ingredient to rapidly enter into the bloodstream, thereby leading to a fast onset of action.

Pharmaceutical preparations comprising compositions of the invention contain a pharmacologically effective amount of the active ingredient. By "pharmacologically effective amount", we refer to an amount of active ingredient, which is capable of conferring a desired therapeutic effect on a treated patient, whether administered alone or in combination with another active ingredient. Such an effect may be objective (i.e. measurable by some test or marker) or subjective (i.e. the subject gives an indication of, or feels, an effect).

More preferred compositions of the invention may be adapted (for example as described herein) to provide a sufficient dose of drug over the dosing interval (irrespective of the number of doses per unit time) to produce a desired therapeutic effect.

The amounts of active ingredients that may be employed in compositions of the invention may thus be determined by the physician, or the skilled person, in relation to what will be most suitable for an individual patient. This is likely to vary with the route of administration, the type and severity of the condition that is to be treated, as well as the age, weight, sex, renal function, hepatic function and response of the particular patient to be treated.

Suitable dosages of active ingredient in one oral delivery unit (e.g. one tablet) may be below 1 g, preferably below 100 mg and above 2 mg. Similar doses may also be appropriate for delivery by other routes, particularly via sublingual, buccal, rectal and vaginal administration.

While NSAIDs are typically used as analgesics, anti-inflammatory drugs and antipyretics, they can also be useful for treatment of primary dysmenorrhea and migraine.

Dysmenorrhea is the pain associated with menstruation in women. It affects approximately 25% of women and in younger women (67-90%) it occurs without underlying problem. (Livshitz and Seidman (2010) Pharmaceuticals, 3, 2082-2089). It has been found that the over-production of uterine PGs is key factor to the painful cramps that are the major symptom of dysmenorrhea. NSAIDs decrease the menstrual pain by decreasing the intrauterine pressure and lowering PGF2a levels in menstrual fluid. (Dawood, M. Y. (1988) Am. J. Med., 20, 23-29). They relieve pain in 80-85% of patients and reduce menorrhagia (bleeding), which has also been correlated with excessive PG synthesis (Ylikorkala, O. (1994) Pharmacol. Toxicol., 75, 86-88), in 30-40%.

Further, NSAIDs can be helpful for planning and timing in-vitro fertilization (IVF) treatments and in attenuating the progression of labour during pregnancy (Livshitz and Seidman (2010) *Pharmaceuticals,* 3, 2082-2089).

Enhancement of NSAIDs bioavailability may implicate important clinical effects due to two reasons: reduced side effects and rapid onset of action.

Side effects: Due to the low solubility/bioavailability NSAIDs are typically administered in high doses to achieve a therapeutic effect. The latter is partly the reason for the side effects associated with NSAIDs, such as gastric ulcers. Thus, lowering the dose when the bioavailability is enhanced may reduce toxic effects.

Onset of action: The relief in dysmenorrhea patients is associated with the rapid onset of action. It is the rapidity with which the NSAIDs are absorbed that determines how quickly the relief is obtained. Since the onset of menstrual flow is variable, it is practical to initiate the medication at the beginning of menstruation and to continue it for 3 days if necessary. With rapidly absorbed NSAIDs, pre-treatment before the onset of dysmenorrhea is unnecessary. This is of great importance since most of the women experiencing dysmenorrhea are young sexually active women.

The fenamates and arylpropionic acid derivatives (profens) are the drugs of choice for treating dysmenorrhea. They act by suppression of menstrual fluid PGs and by a direct analgesic effect. Reduction of menstrual fluid is the result of direct inhibition of PG biosynthesis and release in endometrial tissue—a phenomenon that occurs during the first 48 hours of menstruation. Arylpropionic acid derivatives (such as ibuprofen, flurbiprofen, ketoprofen and naproxen) and fenamates (such as mefenamic acid and flufenamic acid) are particularly useful for treatment of dysmenorrhea. As a rule of thumb, arylpropionic acid derivatives are preferred as they give rise to fewer side-effects, while fenamates are known to have stronger action (Marjoribanks J, et al., 2009. Nonsteroidal anti-inflammatory drugs for primary Dysmenorrhea, Cochrane report, Wiley). The stronger mechanism of fenamate action is believed to be dual, i.e. inhibition of PG synthesis and antagonism to PG in certain tissues. There is a strong correlation between the solubility, dissolution rate and bioavailability of fenamates (Shinkuma, et al., 1984, Int. J. Pharm., 21, 187-200). Varying bioavailability due to poor solubility was the reason why some fenamates have been removed from the market, e.g. flufenamic acid.

Another effective alternative for treatment of primary dysmenorrhea is administration of contraceptives, such as progesterone. The pain associated with dysmenorrhea is postulated to result from progesterone withdrawal before the onset of menses, which causes an increase in PGs. Therefore, administration of progesterone can alleviate the symptoms of primary dysmenorrhea.

With a prevalence of 8% in males and 12-15% in females migraine is extremely common (Diener, H. C.; Katsarava, Z.; Limmroth, V. Schmerz 2008, 22 (Suppl. 1), 51-58.). It is characterized by recurrent attacks of pulsatile, unilateral headache often accompanied by nausea and vomiting, photo- and phonophobia. In about 20% of patients the headache is preceded by an aura consisting of transient neurological symptoms, most frequently a scintillating scotoma. While the "triptans"—e.g., sumatriptan (Imitrex), rizatriptan (Maxalt), eletriptan (Relpax)—have been promoted over the last 2 decades, NSAIDs still remain a treatment option for acute migraine headache.

Compositions of the invention comprising NSAIDs are therefore useful in the treatment of migraine (e.g. acute migraine headache) and/or dysmenorrhea (e.g. primary dysmenorrhea). According to a further aspect of the invention there is provided a method of treatment of migraine (e.g. acute migraine headache) which method comprises administration of a composition of the invention to a person suffering from, or susceptible to, such a condition. According to a still further aspect of the invention there is provided a method of treatment of dysmenorrhea (e.g. primary dysmenorrhea) which method comprises administration of a composition of the invention to a person suffering from, or susceptible to, such a condition.

According to a further aspect of the invention there is provided the use of an active pharmaceutical ingredient (e.g. an NSAID) in the manufacture of a composition of the invention for treating migraine (e.g. acute migraine headache). Similarly, there is provided the use of an active pharmaceutical ingredient (e.g. an NSAID or a contraceptive) in the manufacture of a composition of the invention for treating dysmenorrhea (e.g. primary dysmenorrhea).

For the avoidance of doubt, by "treatment" we include the therapeutic treatment, as well as the symptomatic treatment, the prophylaxis, or the diagnosis, of the condition.

When compositions of the invention comprise NSAIDs, appropriate pharmacologically effective amounts of such compounds include those that are capable of producing (e.g. immediate) relief of pain or other symptoms when administered perorally. The amount of the NSAID active ingredient may be expressed as the amount in a unit dosage form. In such a case, the amount of NSAID active ingredient that may be present may be sufficient to provide a dose per unit dosage form that is in the range of between about 2 mg and about 1000 mg (e.g. about 200 mg or 400 mg).

The above-mentioned dosages are exemplary of the average case; there can, of course, be individual instances where higher or lower dosage ranges are merited, and such are within the scope of this invention.

Compositions of the invention possess the advantage of reducing the risks of producing side effects that are typically associated with high doses of drugs. By delivering the active pharmaceutical ingredient in such a way that the higher rates of dissolution than normal can be achieved, the compositions may contain a lower overall quantity of the active pharmaceutical ingredient while still providing a rapid therapeutic benefit for the patient. The use of a lower overall quantity of the active pharmaceutical ingredient helps to reduce the occurrence of unwanted side effects that may occur. NSAIDs in particular may benefit from being used in the compositions of the invention frequent usage of these drugs is associated with a substantially increased risk of gastrointestinal problems (e.g. gastrointestinal bleeding and ulcers) and kidney problems).

Compositions of the invention may also have the advantage that they may be prepared using established pharmaceutical processing methods and may employ materials that are approved for use in foods or pharmaceuticals or of like regulatory status.

Compositions of the invention may also have the advantage that they may be more efficacious than, be less toxic than, be longer acting than, be more potent than, produce fewer side effects than, be more easily absorbed than, and/or have a better pharmacokinetic profile than, and/or have other useful pharmacological, physical, or chemical properties over, pharmaceutical compositions known in the prior art, whether for use in the treatment of pain or otherwise.

Wherever the word "about" is employed herein in the context of dimensions (e.g. values, temperatures, pressures (exerted forces), relative humidities, sizes and weights, crystallinities, surface area, particle or grain sizes, etc.), amounts (e.g. relative amounts (e.g. numbers or percentages) of particles, individual constituents in a composition or a component of a composition and absolute amounts, such as doses of active ingredients, numbers of particles, etc.), deviations (from constants, degrees of degradation, etc.) it will be appreciated that such variables are approximate and as such may vary by ±10%, for example ±5% and preferably ±2% (e.g. ±1%) from the numbers specified herein.

Preferences and options for a given aspect, feature or parameter of the invention should, unless the context indicates otherwise, be regarded as having been disclosed in combination with any and all preferences and options for all other aspects, features and parameters of the invention. For example, combinations of the preferred active pharmaceutical ingredients (e.g. an active pharmaceutical ingredient selected from the group consisting of ibuprofen, ketoprofen, flurbiprofen, naproxen, mefenamic acid, flufenamic acid, tolfenamic acid, indomethacin, sulindac, pyroxicam, progesterone, estradiol, progestin, estrogen, cholic acid, deoxycholic acid and ursodeoxycholic acid) and the preferred algae-derived cellulose (e.g. cellulose obtained from algae of the genus *Cladophora*) should be regarded as having been disclosed.

The invention is best demonstrated by comparison of algae derived cellulose with MCC mixtures. For each cellulose, two types of mixtures have been prepared, i.e. normal, physical mixtures and statically heat sealed mixtures. The invention is illustrated by the following examples in which:

FIG. 1 shows DSC profiles of ibuprofen (IBU) and cellulose. FIG. 1(a) shows the DSC profiles of pure crystalline IBU, pure MCC and *Cladophora* cellulose samples. The DSC profile for crystalline IBU is characterized by sharp melting endotherm at 78° C. The DSC profiles for cellulose were characterized by a water evaporation broad endotherm. In a mixture the two endothermic events will overlap due to the relatively low melting temperature of IBU. FIG. 1(b) shows the DSC profile of both physical and heated mixtures of IBU and MCC (10% IBU). Both in the physical and heated mixtures of IBU with MCC the endothermic event corresponding to melting of IBU is clearly visible, although the melting temperature is shifted slightly to lower temperatures, i.e. 73° C. (heated) vs. 76° C. (physical). FIG. 1(c) shows the DSC profile of both physical and heated mixtures of IBU and *cladophora*-derived cellulose (CLAD) (10% IBU). The endothermic event corresponding to melting of IBU is clearly visible in the physical mixture but it is completely absent in the heated mixture;

FIG. 2 represents the XRD profile of IBU and cellulose. FIGS. 2(a) and 2(b) show the XRD profiles of IBU-MCC 10% physical and heated mixtures, respectively. The dotted line represents the XRD profile of crystalline XRD. The sharp peaks of crystalline IBU overlaid on MCC background are clearly visible in both physical and heated mixtures of IBU-MCC. FIGS. 2(c) and 2(d) show the XRD profiles of IBU-CLAD 10% physical and heated mixtures, respectively. The characteristic peaks for crystalline IBU, otherwise seen in the physical mixture of MCC, are either substantially suppressed (physical mixture) or completely disappear in the heated mixture of *Cladophora*;

FIG. 3 shows XRD profiles of heated IBU-CLAD samples in various ratios, (i.e. 10, 20 and 30% by weight IBU relative to the IBU-CLAD mixture) and stored at 40% relative humidity (RH) for 1 (FIG. 3(a)), 2 (FIG. 3(b)), and 6 months (FIG. 3(c)). It is seen from the graph that in heated IBU-CLAD samples below 20% IBU is essentially amorphous for up to a 6-month period;

FIG. 4 shows the FTIR profiles of pure ibuprofen, pure cellulose (MCC or CLAD) and IBU-cellulose (MCC or CLAD) in the regions corresponding to the stretch C=O bond (FIG. 4(a)/(c)/(e)) and C—H vibrations in the aromatic ring (FIG. 4(b)/(d)/(f)). FIG. 4(a) shows the FTIR profile corresponding to the stretch C=O bond (ca. 1720 cm$^{-1}$) for pure ibuprofen. FIG. 4(b) shows the FTIR profile corresponding to the C—H vibrations in the aromatic ring (ca. 900 to 750 cm$^{-1}$) for pure ibuprofen. FIG. 4(c) shows the FTIR profile corresponding to the stretch C=O bond (ca. 1720 cm$^{-1}$) for IBU-MCC in physical and heated mixtures. No shift in the position of C=O peak is observed. FIG. 4(d) shows the FTIR profile corresponding to the C—H vibrations in the aromatic ring (ca. 900 to 750 cm$^{-1}$) for IBU-MCC physical and heated mixture, which appear similar. FIG. 4(e) shows the FTIR profile corresponding to the stretch C=O bond (ca. 1720 cm$^{-1}$) for IBU-CLAD in the physical and heated mixtures. A slight shift to the right side is observed in the heated mixture suggesting significant molecular rearrangement. FIG. 4(f) shows the FTIR profile corresponding to the C—H vibrations in the aromatic ring (ca. 900 to 750 cm$^{-1}$) for IBU-CLAD physical and heated mixture. The FTIR profile for heated mixture is significantly distorted suggesting molecular interaction between cellulose and IBU involving the aromatic ring;

FIG. 5 shows the in vitro dissolution profile of IBU in mixtures with cellulose (10% IBU by weight relative to the mixture). FIG. 5(a) shows the dissolution of IBU from physical and heated mixtures of IBU-MCC. The dotted line represents the dissolution of pure crystalline IBU as a benchmark. It is seen that the dissolution of IBU is slightly improved in the heated MCC mixture compared to physical mixture and pure IBU. FIG. 5(b) shows the dissolution of IBU in CLAD physical and heated mixtures. It is seen in FIG. 5(b) that the dissolution of IBU is slightly improved in the physical mixture compared to pure IBU. The most dramatic improvement in dissolution of IBU is observed in the heated IBU-CLAD mixture;

FIG. 6 shows the plasma concentration of IBU following administration of a physical mixture of IBU-MCC, and physical and heated mixtures of IBU-CLAD. In each case, the starting mixture contained (10% IBU by weight relative to the mixture). It is seen in the graph that CLAD mixtures exhibit improved bioavailability compared to the IBU-MCC mixture. The fastest absorption was observed for the heated IBU-CLAD mixture;

FIG. 7 shows the DSC profiles for flufenamic acid (FFA) mixtures with cellulose. The DSC profile for pure FFA (not shown) showed a distinct endotherm at 135° C. corresponding to the melting temperature of crystalline FFA. The DSC profile of MCC in mixture with FFA (FIG. 7(a)) displayed several distinguishable peaks close to the melting region of FFA, typically below the specific melting temperature. The absence of the melting peak of FFA (at 135° C.) in the DSC profiles in heated FFA-CLAD samples (FIG. 7(b)) is indicative of an amorphous structure of FFA in the heated samples, since fully amorphous materials do not exhibit a melting endotherm;

FIG. 8 shows the XRD profiles of FFA with celluloses (MCC—Figs (a) and (b); *Cladophora*—Figs. (c) and (d)). In the physical mixtures (FIGS. 8(b) and 8(d)), the sharp peaks of crystalline FFA are visible. In the heated samples (FIGS. 8(a) and 8(c)) the peaks are significantly suppressed and in the heated CLAD sample the peaks are absent; the shift in the characteristic sharp diffraction peaks of crystalline FFA in mixture compared to pure FFA suggest molecular rearrangement and formation of polymorphs, while the absence of sharp diffraction peaks suggests amorphous FFA. As many as 8 different FFA polymorphs are known, see Lopez-Mejia et al. J. Am. Chem. Soc. 2012, 134, 9872-9875;

FIG. 9 shows the FTIR results of FFA with celluloses in the regions corresponding to the stretch C=O bond (FIGS. 9(a)/(c)) and C—H vibrations in the aromatic ring (FIGS. 9(b)/(d)). FIG. 9(a) shows the FTIR profile corresponding to the stretch C=O bond (ca. 1650 cm$^{-1}$) for FFA-MCC in physical and heated mixtures. No significant shift in the position of C=O peak is observed. FIG. 9(b) shows the FTIR profile corresponding to the C—H vibrations in the aromatic ring (ca. 1000 to 600 cm$^{-1}$) for FFA-MCC physical and heated mixtures, which appear similar. FIG. 9(c) shows the FTIR profile corresponding to the stretch C=O bond (ca. 1650 cm$^{-1}$) for FFA-CLAD in physical and heated mixtures. The region of 1000 to 600 cm$^{-1}$ and 1800 to 1400 cm$^{-1}$ in FTIR spectra are the most informative, since characteristic bands corresponding to the functional groups of FFA are distinctively present in these two regions. Detailed analysis of FTIR spectra is provided in S. Jabeen, T. J. Dines, S. A. Leharne and B. Z. Chowdhry, "Raman and IR spectroscopic studies of fenamates—Conformational differences in polymorphs of flufenamic acid, mefenamic acid and tolfenamic acid," *Spectrochim. Acta Part A Mol. Biomol. Spectrosc.*, vol. 96, pp. 972-985, 2012. The region of 1000 to 600 cm$^{-1}$ is predominantly related to aromatic out-of-plane C—H deformations and benzene ring deformations. In addition to the bands corresponding to C—H vibrations in the aromatic rings, the vibrations in CF$_3$ group appear in this region of 1000 to 600 cm$^{-1}$ as well. More specifically, the characteristic bands at 889, 787 and 760 cm$^{-1}$ appear due to aromatic ring deformations, while the bands at 659 and 652 cm$^{-1}$ are associated with vibrations of the CF$_3$ group. The spectral range between 1800 and 1400 cm$^{-1}$ involves signals of mixed character. The bands at 1423, 1454, and 1493 cm$^{-1}$ are due to in-plane aromatic C—H deformation, benzene ring stretching and C—N stretching. The bands at 1519 and 1578 cm$^{-1}$ are of mixed origin and arise due to benzene ring C—N stretching as well as in-plane N—H deformation. In particular, the band at 1655 cm$^{-1}$ arises due to carbonyl C=O group stretching.

The bands associated with stretching and deformations in the FFA molecule were studied to reveal potential interactions between the drug and the excipient. The FTIR spectra for physical blends of *Cladophora* cellulose-FFA display an apparent difference of band characteristics in both selected regions, i.e. the characteristic bands appeared to shift to higher wavenumbers, become broader and generally decrease in intensity. This is observed particularly for bands corresponding to CF$_3$ vibration at 659 and 652 cm$^{-1}$, aromatic out-of-plane C—H deformations at 889 cm$^{-1}$ and in-plane aromatic C—H deformation at 1422 cm$^{-1}$. The characteristic FFA bands in physical mixture with MCC demonstrated no particular deviation from relevant band positions.

The FTIR spectra for heated samples revealed even more remarkable deviations from the characteristic band positions of FFA in reference spectra. In the selected spectral regions, a shift in band positions is observed at nearly all bands of pure FFA for each heated cellulose-FFA mixture. The characteristic bands of FFA shifted in their wavenumber position and were further accompanied by a broader appearance and lower intensity in spectra for heated MCC-FFA. The heated *Cladophora* cellulose-FFA mixture expressed the most obvious shift to higher wavenumbers for characteristic FFA bands in the region of 1800-1500 cm$^{-1}$. Furthermore, the appearance of these peaks was much more prominent for *Cladophora* cellulose than MCC. The shift in the band position at 1655 cm$^{-1}$ was prominent in spectra for heated samples of *Cladophora* cellulose-FFA where the band position shifted to higher wavenumber in the heated sample of *Cladophora* cellulose-FFA. Since the band associated with carbonyl stretching at 1655 cm$^{-1}$ is especially sensitive to changes in the electrostatic environment of the molecule, a shift in the wavenumber position at this band is particularly indicative of interaction involving carboxylic group of FFA and cellulose. When the strength of the carbonyl bond is weakened by an intramolecular interaction, a shift to lower wavelengths is observed. The observed shift in the band position at 1655 cm$^{-1}$ in the heated mixture of MCC-FFA appeared inferior when compared to FFA in formulation with *Cladophora* cellulose. While some peaks for heated MCC-FFA shifted in the band position, other peaks such as 760, 1519 and 1578 cm$^{-1}$ were diffuse and of remarkably low intensity, which could be due to interference from water in these samples. Overall, the results from FTIR analysis suggest that a potential interaction is present between FFA and the different celluloses, particularly for FFA in formulation with *Cladophora* cellulose in the heated samples;

FIG. 10 shows the in vitro dissolution profiles of FFA with celluloses in simulated intenstinal fluid. The heated mixture of FFA and CLAD (FIG. 10(b)) shows an immediate and rapid increase of the FFA concentration in the solvent. This rapidity of the increase was much greater than for the physical mixture of FFA and CLAD. For heated and physical mixtures of FFA and MCC (FIG. 10(a)), the release profiles were broadly similar;

FIG. 11 shows the DSC results for mixtures of *Cladophora* cellulose with various drugs: ketoprofen (Fig. (a)), flurbiprofen (Fig. (b)), naproxen (Fig. (c)), indomethacin (Fig. (d)), sulindac (Fig. (e)), piroxicam (Fig. (f)), flufenamic acid (Fig. (g); N.B, flufenamic acid here was mixed using Turbula Mixer and heated to 138° C. for 3 hours as opposed to Example 2), and mefenamic acid (Fig. (h)). In each case, the endothermic event visible corresponding to melting of the drug in the physical mixture is completely absent in the heated mixture;

Figure 14A:
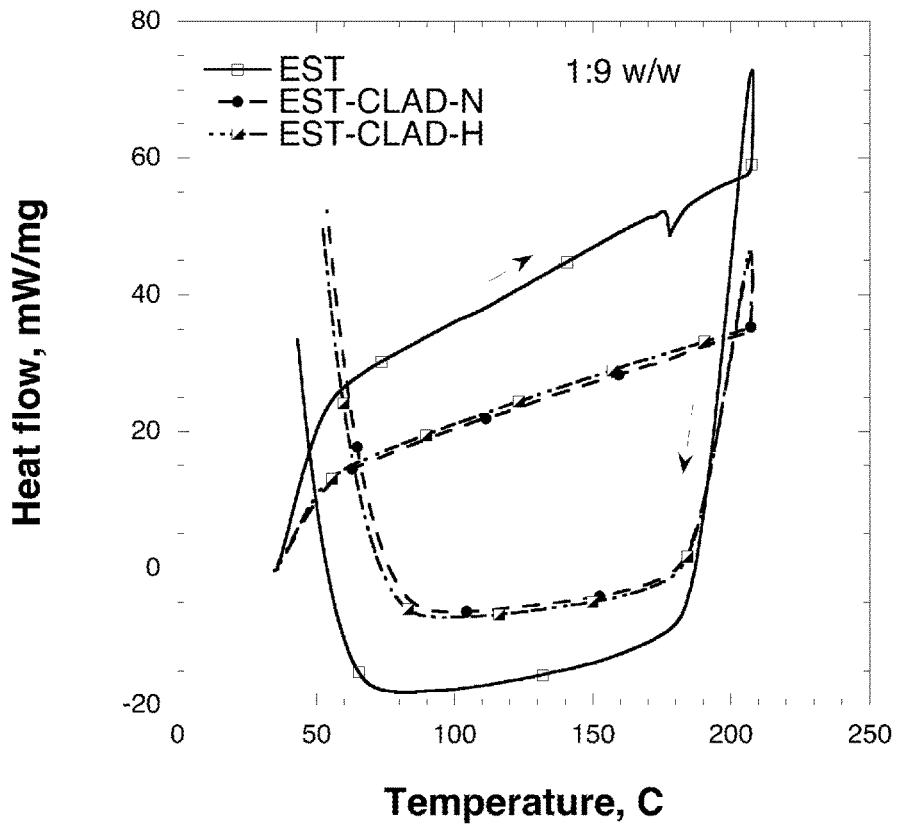
Figure 14B:
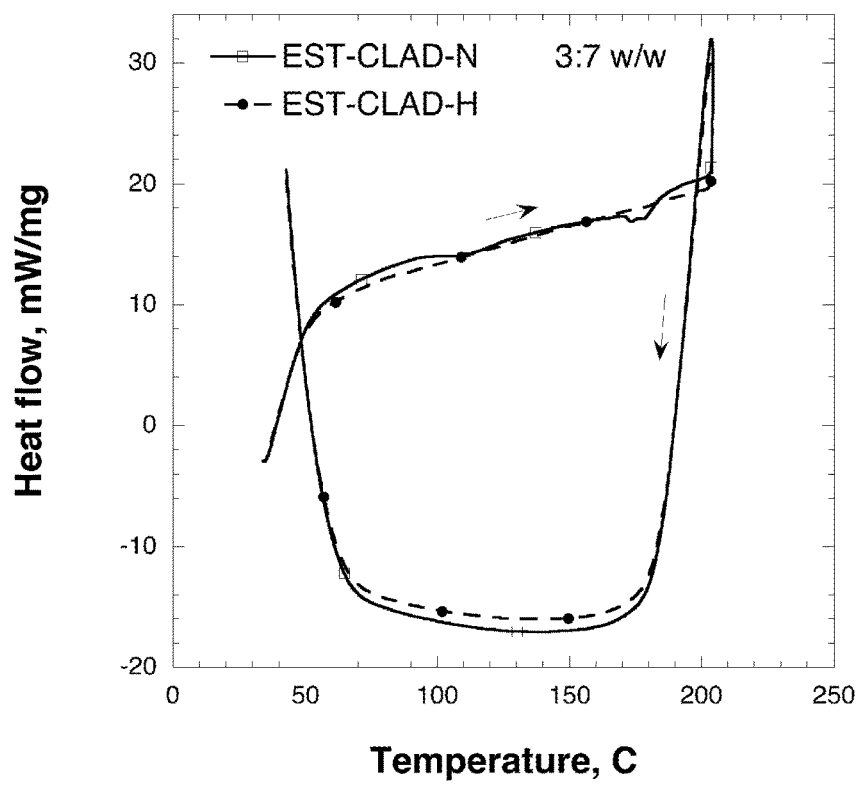
Figure 15:
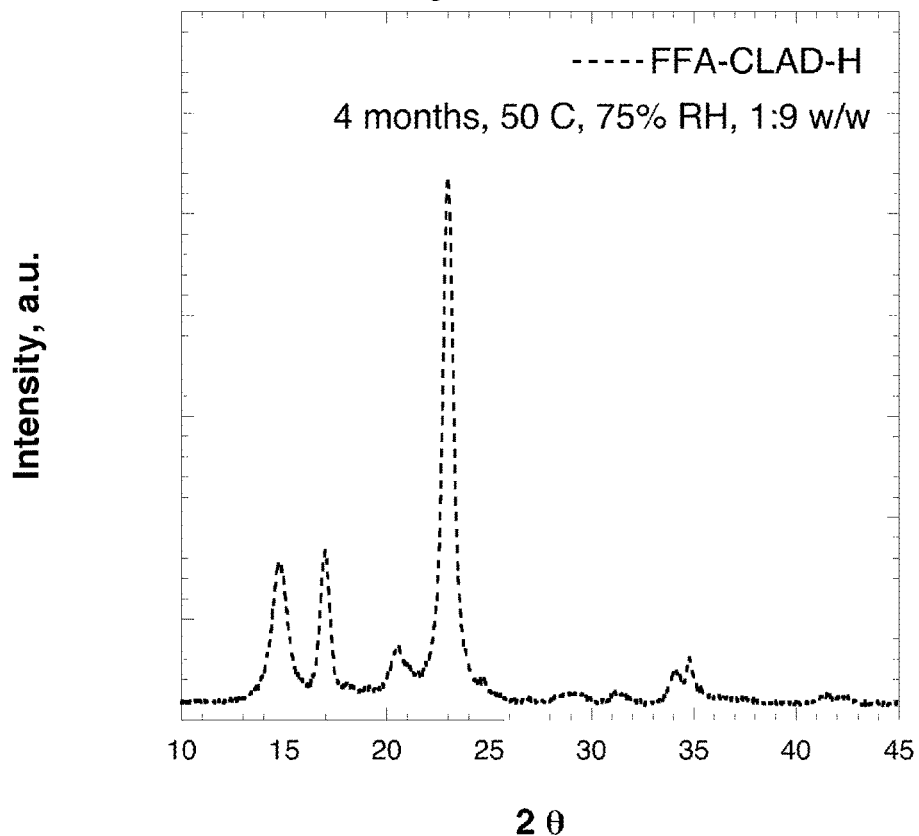
Figure 16:
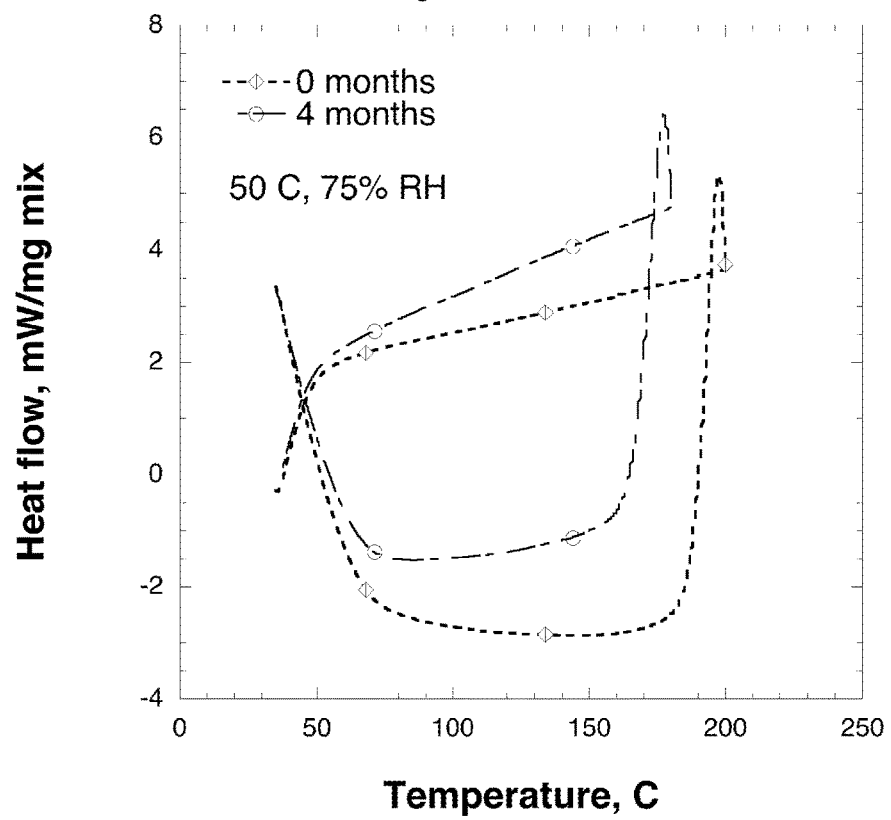

FIG. 14 shows the DSC results for normal and heated mixtures of *Cladophora* cellulose with β-estradiol in various proportions. At lower drug concentrations (10 wt %; FIG. 14(a)), no endothermic event is visible for the melting of the drug for the normal and heated mixtures. At higher drug concentrations (30 wt %; FIG. 14(b)), an endothermic event corresponding to melting of the drug in the physical mixture is visible but is completely absent in the heated mixture;

FIG. 15 shows the XRD profile of a heated mixture of FFA and CLAD cellulose following storage for 4 months at 50° C. and 75% relative humidity; and FIG. 16 shows the TGA results for a heated mixture of FFA and CLAD cellulose before and after storage for 4 months at 50° C. and 75% relative humidity.

EXPERIMENTAL

A typical process for obtaining *Cladophora*-derived cellulose from a suitable source (e.g. *Cladophora* green algae) is disclosed in Mihranyan et al. Int. J. Pharm. 2004; 269 (2), 433-442. In such a method, algae is bleached (e.g. with NaClO$_2$ adjusted with acetic acid or another suitable buffer to pH 4-5) under appropriate conditions (e.g. at about 60° C. for about 3 hours). The solution is then cooled, filtered, washed until conductivity of the wash solution is less not more than 75 μS/cm, and dried. Typically the drying is achieved through spray-drying using an outlet temperature of not less than 95° C. The resulting product is then washed until neutrality and filtered. The filtered product may be further washed with a basic solution (e.g. 0.5M NaOH or 17.5% w/v solution) before being dried and ground, e.g. hummer-type mill, e.g. Fitz Mill type D, UK. The ground material is treated using acidic hydrolysis (e.g. by adding it to a 5% HCl solution and then heating to boiling). The solution is then cooled, filtered, washed until the conductivity of wash water is not more than 75 μS/cm and dried, e.g. spray-dried using an outlet temperature not lower than 95° C.

One skilled in the art will understand that variations of this manufacturing process may be employed e.g. with respect to the bleaching procedure the use of $H_2O_2$ or an alkaline metal percarbonate salt could be employed to substitute halogen atom containing bleaches (e.g. chlorites and hypochlorites) due to environmental and safety concerns (hazardous chlorine gas evolution). Further, the hydrochloric acid may be substituted by another suitable mineral acid such as sulphuric acid or phosphoric acid in the acidic hydrolysis step.

All active pharmaceutical ingredients were purchased from Sigma Aldrich with a purity of no less than 98-99%.

Example 1—Ibuprofen (IBU)

Product Preparation

*Cladophora*-derived cellulose (CLAD) was obtained from *Cladophora* green algae using the method disclosed in Mihranyan et al. Int. J. Pharm. 2004; 269 (2), 433-442.

Physical mixtures of drug (Ibuprofen) and either microcrystalline cellulose (MCC) or *cladophora*-derived cellulose (CLAD) were prepared by blending the drug substance with the cellulose. Unless otherwise stated, the weight ratio between the drug and cellulose was 1:9. The surface area of the *cladophora*-derived cellulose was found to be 98.79 $m^2/g$ (as measured by $N_2$ gas adsorption technique according to the Brunauer Emmett Teller (BET) method). Typically, in a glass vial 5 mg of the drug was mixed with 45 g of the cellulose using a Turbula mixer (Switzerland) for 15 minutes.

Heated mixtures of drug and cellulose (e.g. MCC or CLAD) were prepared by obtaining a physical by the process above and placing it is a sealed vial. The mixture was then heated to around 10° C. higher than the corresponding melting temperature of the drug for 3 hours. All samples were used after 24 hrs from the time of preparation after cooling to room temperature.

Differential Scanning Calorimetry (DSC)

Figure 1A:
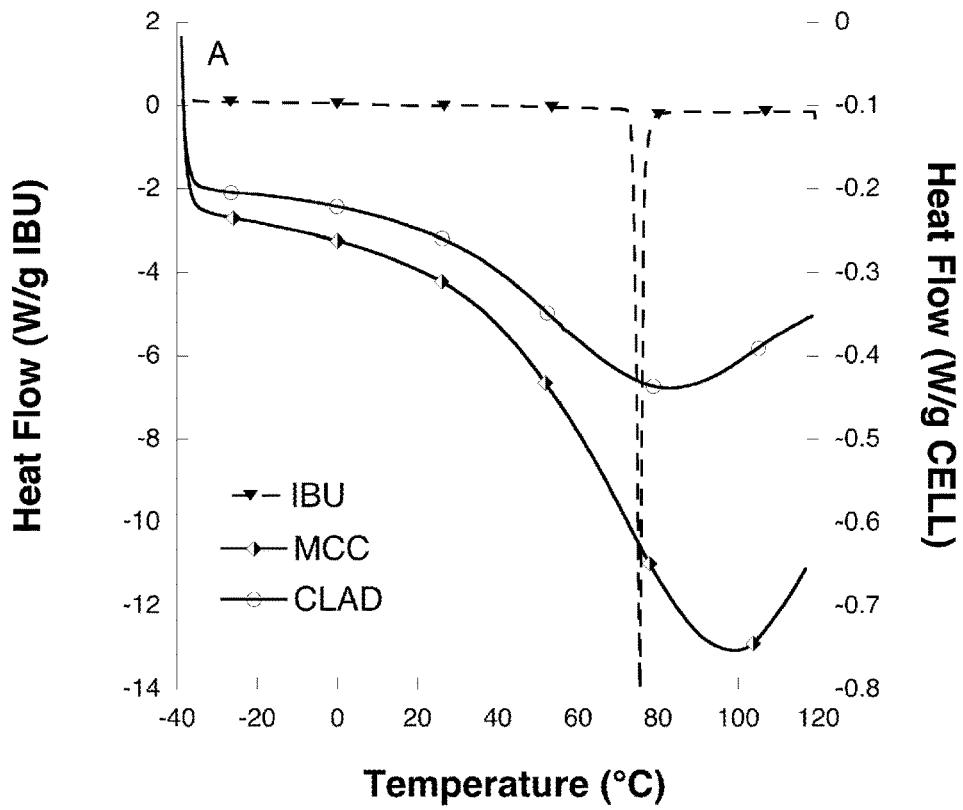
Figure 1B:
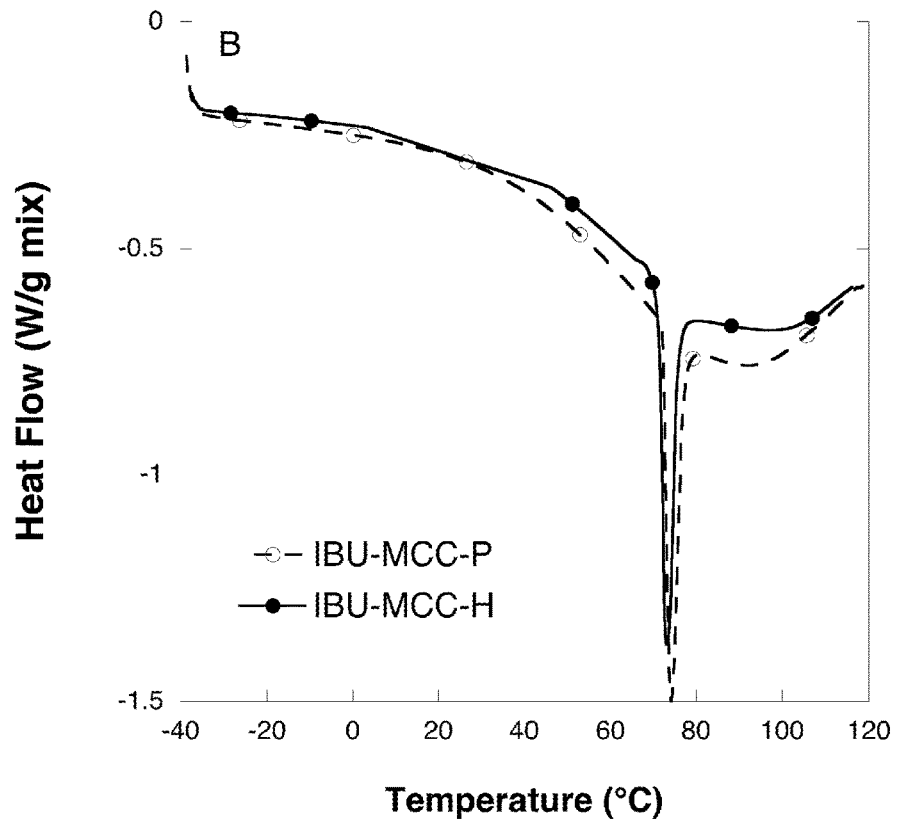
Figure 1C:
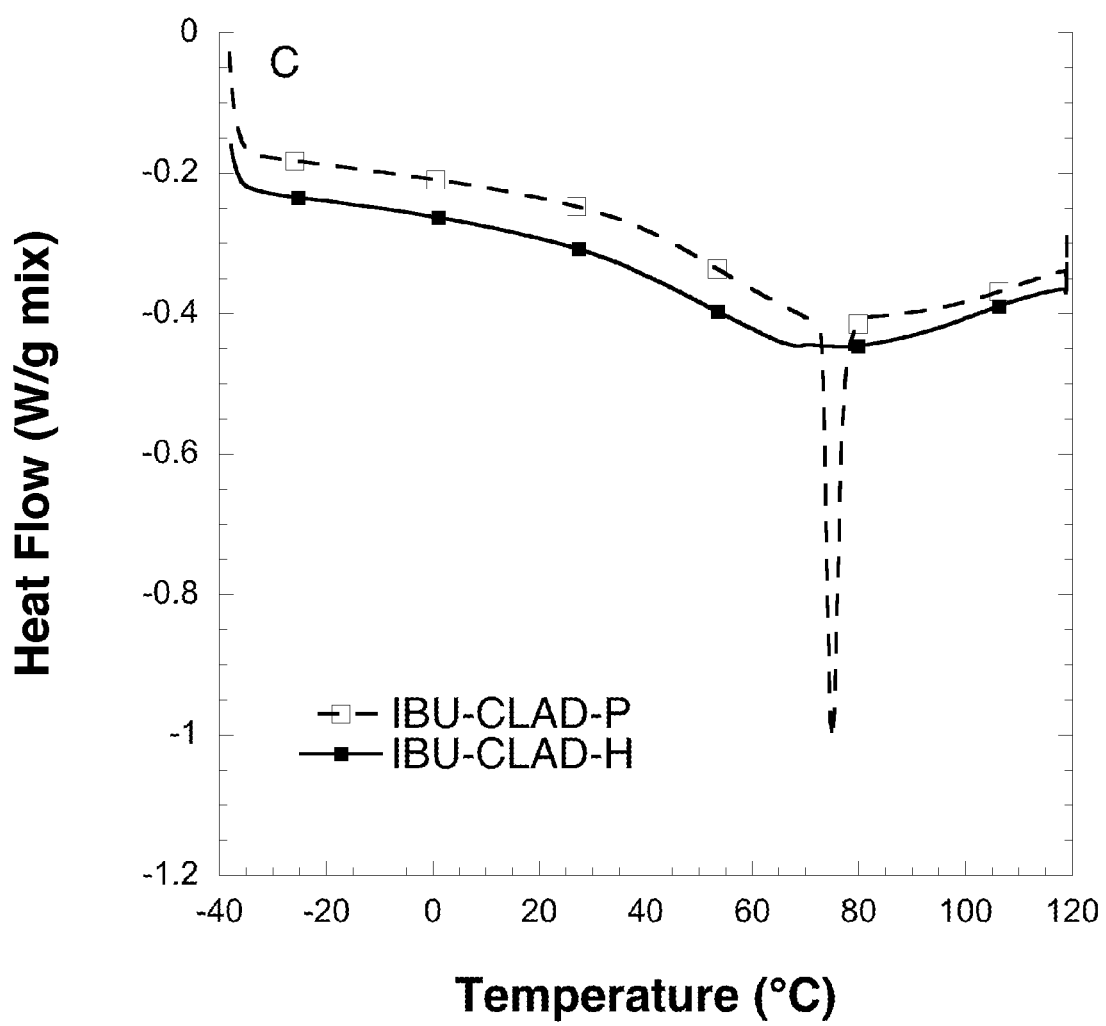
Figure 2A:
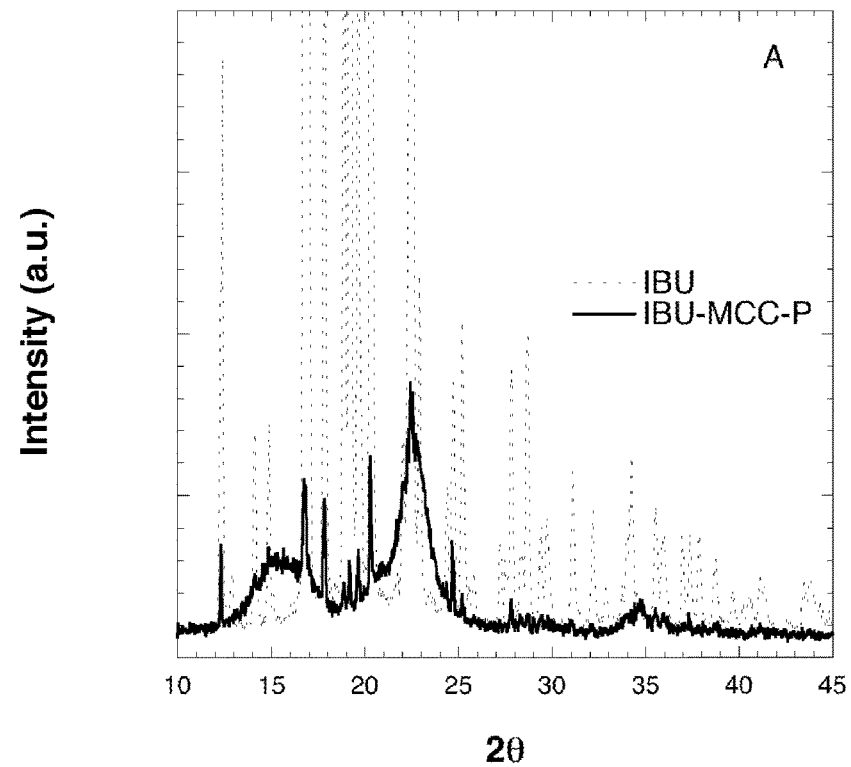
Figure 2B:
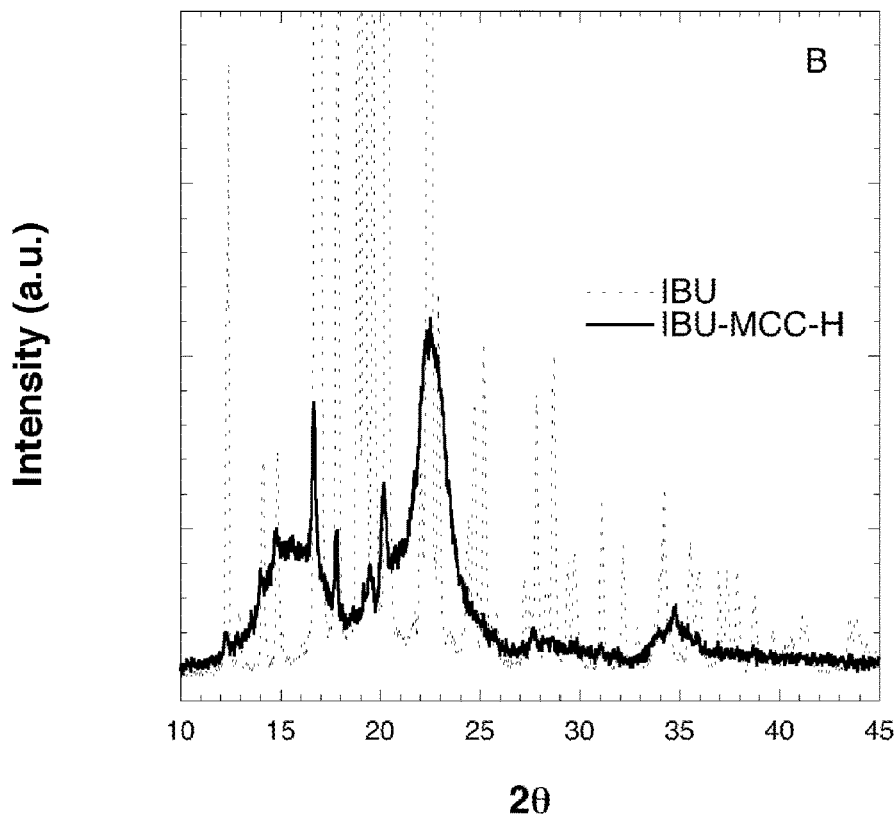
Figure 2C:
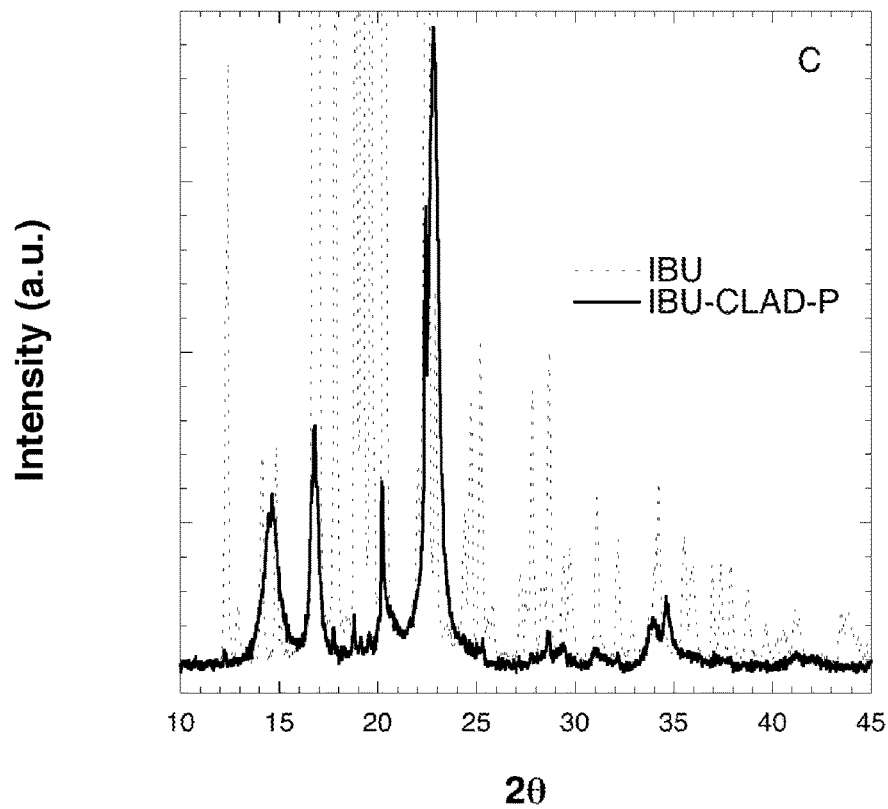
Figure 2D:
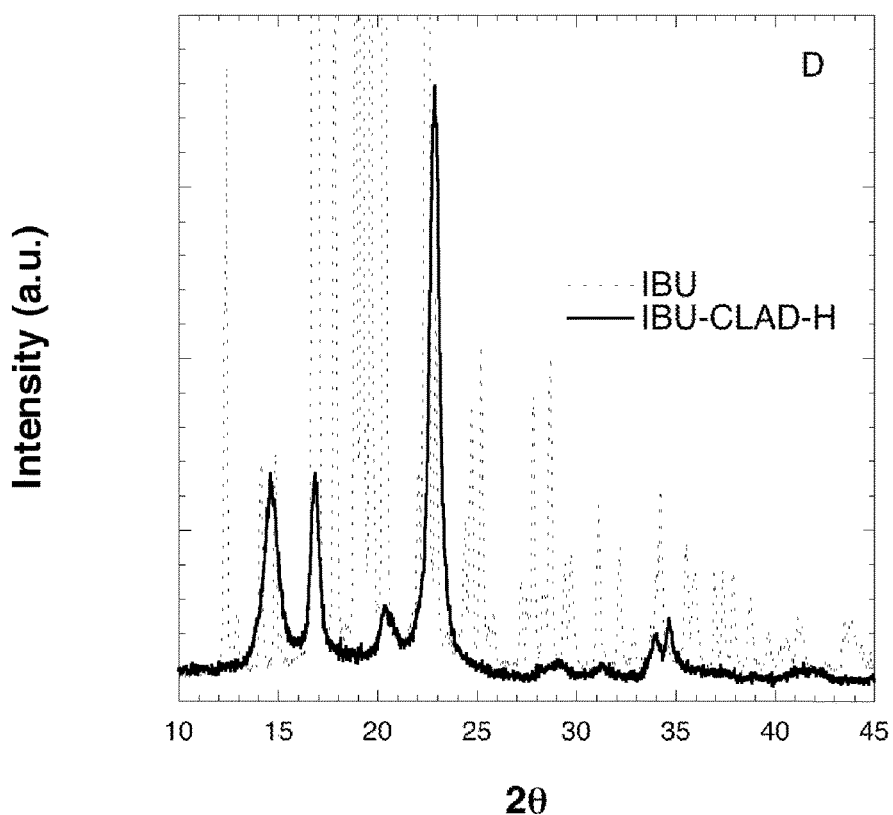

The DSC measurements were performed with Q 2000 TA instrument (USA). The samples were first cooled from room temperature to −40° C. and then heated to around 10° C. higher than the melting temperature at 10° C./min heating rate. Typically, 10 mg of 1:9 drug-cellulose mixture was used per measurement. For pure substances, 1 mg of drug and 10 mg of cellulose were used per measurement. The pan containing the sample was punctured to avoid overpressure. Results are shown in FIG. 1.

Fourier Transform Infrared Spectroscopy (FTIR)

FTIR spectrum was used to follow the interactions between the model drug and cellulose. The range for measurements was set from 4000 to 400 $cm^{-1}$. The most informative regions relevant for this study included the area from 1800 to 1600 $cm^{-1}$, corresponding to stretch of C=O bonds, and the area from 1000 to 600 $cm^{-1}$, corresponding to C—H vibrations in the aromatic ring. The measurements were performed with Bruker Tensor 27 FT-IR according to the pellets technique using potassium bromide (KBr). The amount of model drug substance in the 1:9 drug cellulose mixture was about 2 mg. The amount of KBr used was around 200 mg. Results are shown in FIG. 4.

Powder X-Ray Diffraction (PXRD)

An X-ray diffractometer (D8 Twin-Twin, Bruker) with Bragg-Brentano geometry (CuKα radiation; λ=1.54 Å) was used. Results are shown in FIG. 2.

Storage Stability Study

Figure 3A:
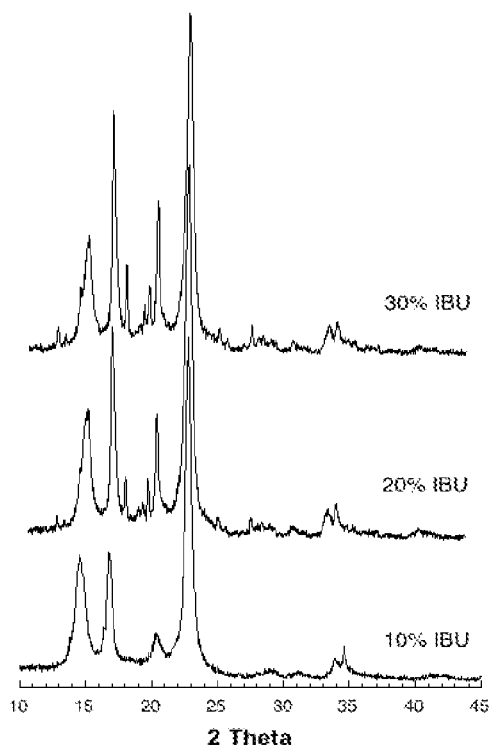
Figure 3B:
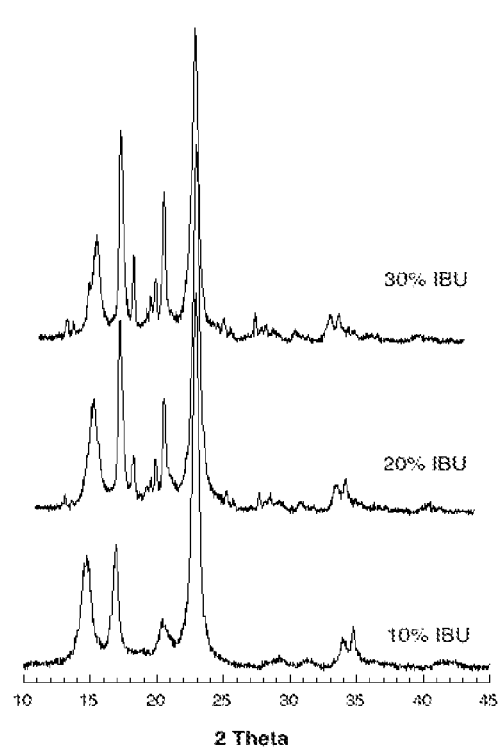
Figure 3C:
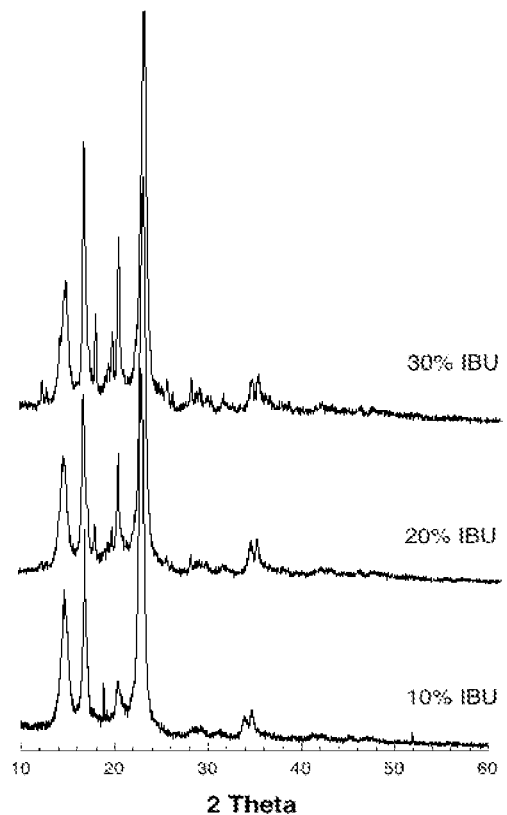
Figure 4A:
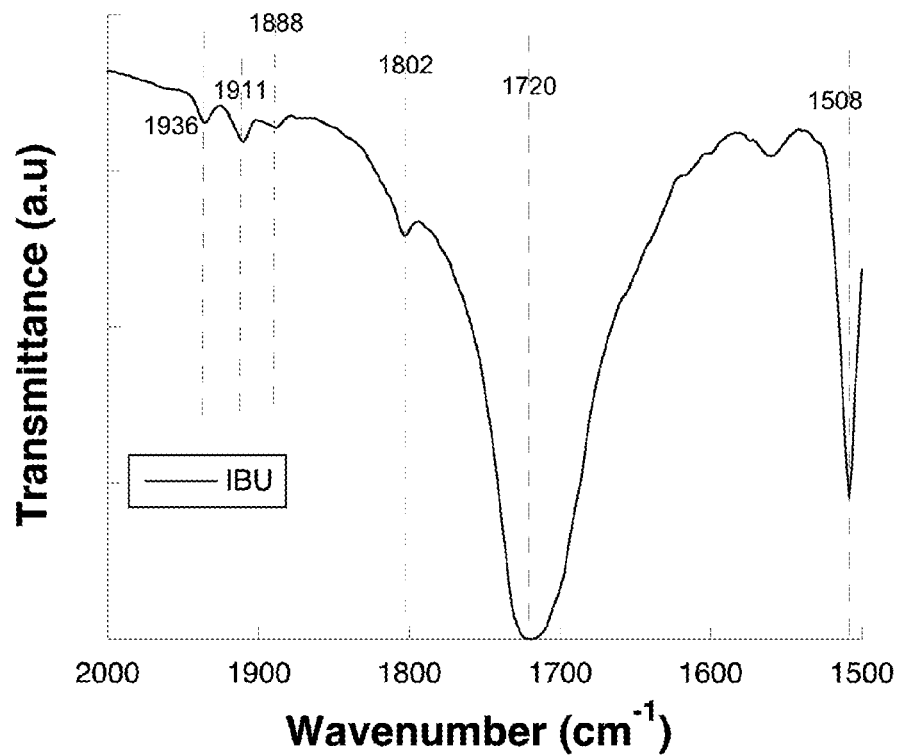
Figure 4B:
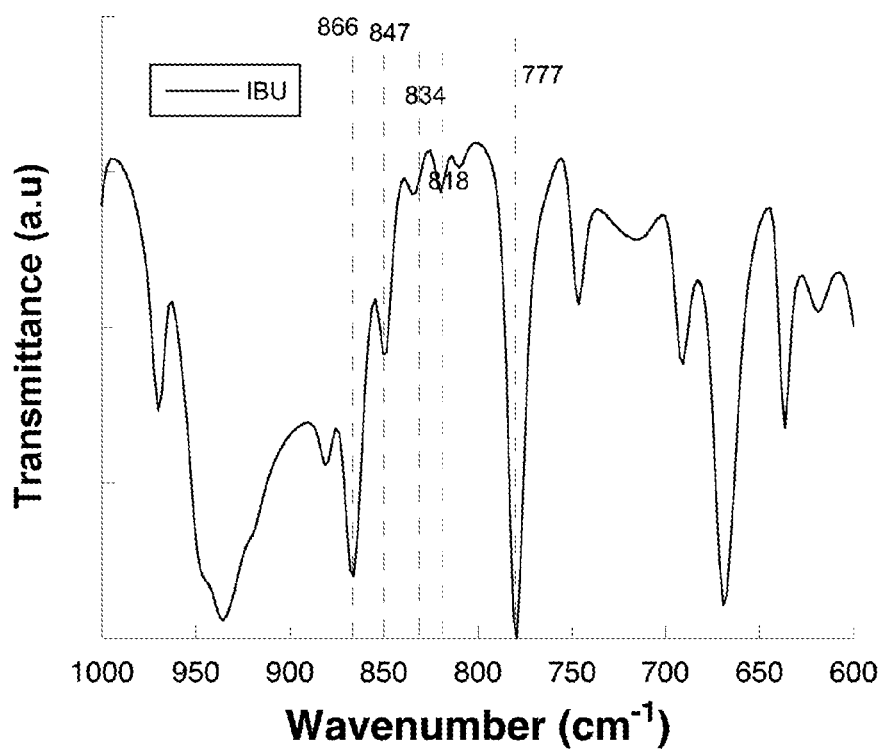
Figure 4C:
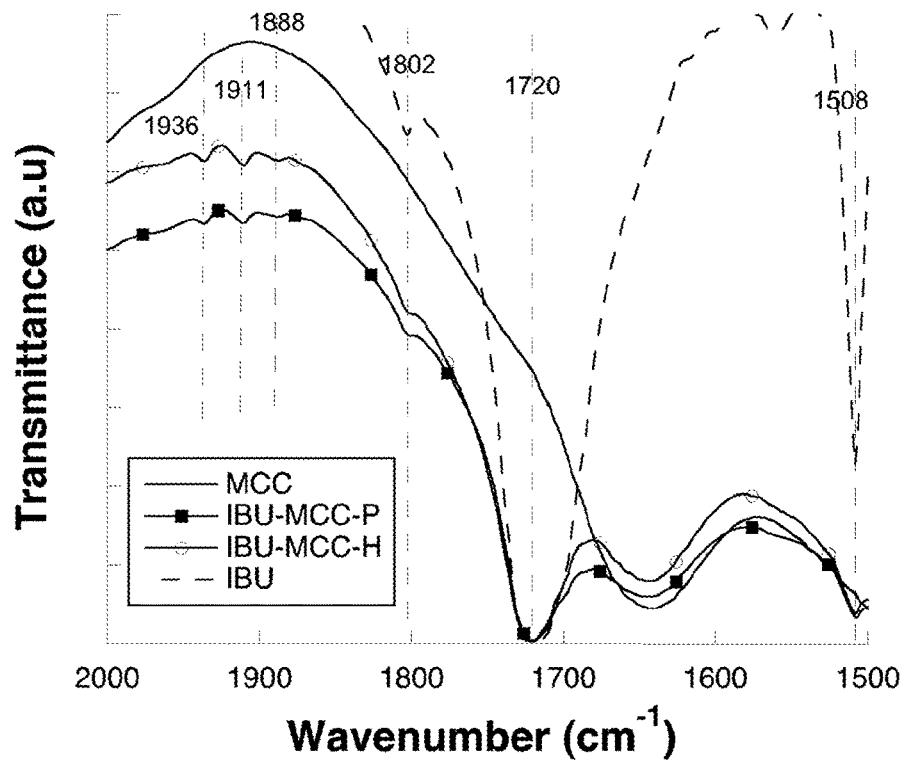
Figure 4D:
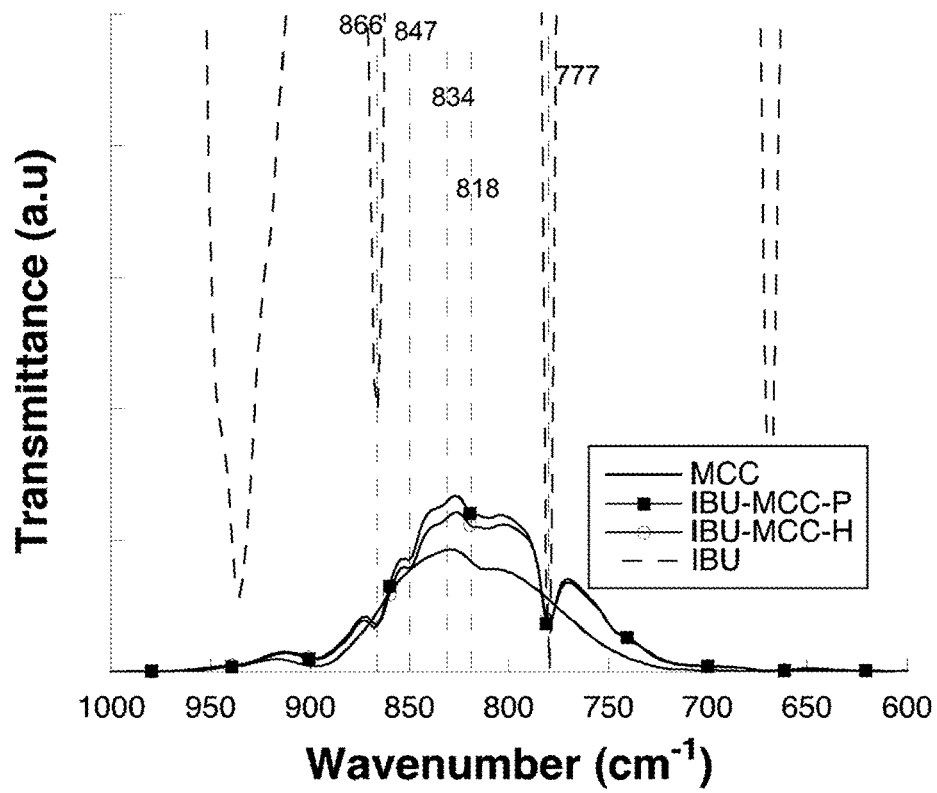
Figure 4E:
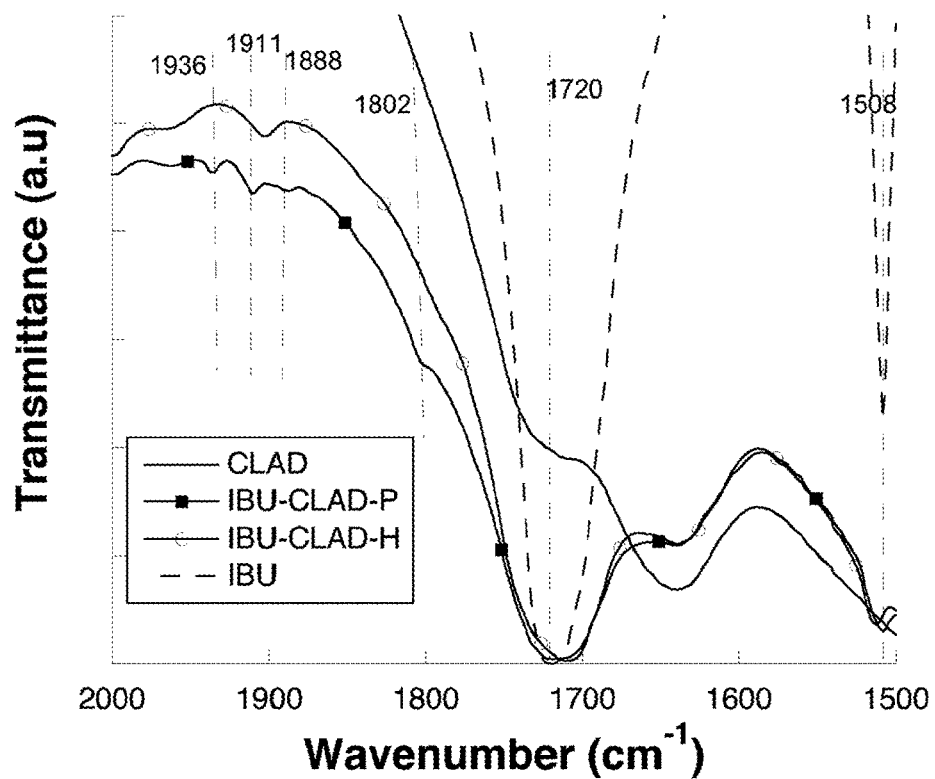
Figure 4F:
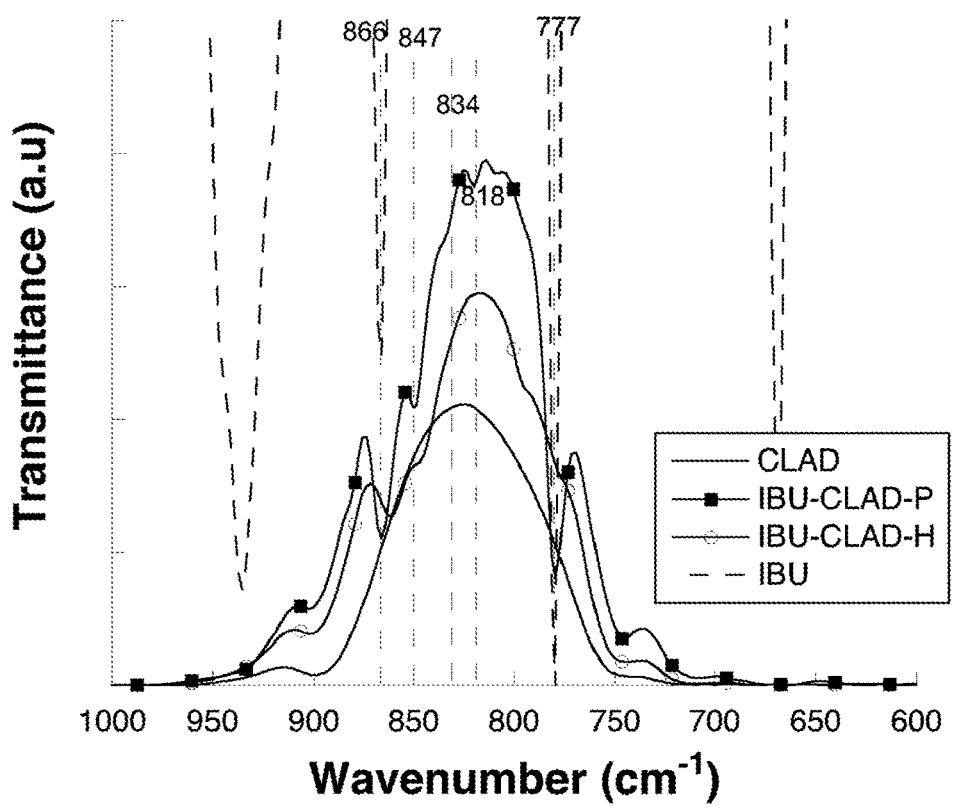

Heated IBU-CLAD samples were prepared as described above containing various proportions of cellulose and drug: 10, 20 and 30% by weight IBU relative to the IBU-CLAD mixture. Each sample was stored at 40% relative humidity (RH) for up to 6 months. Results of XRD analyses at 1, 2, and 6 months are shown in FIG. 3.

In Vitro Drug Release in Water

Figure 5A:
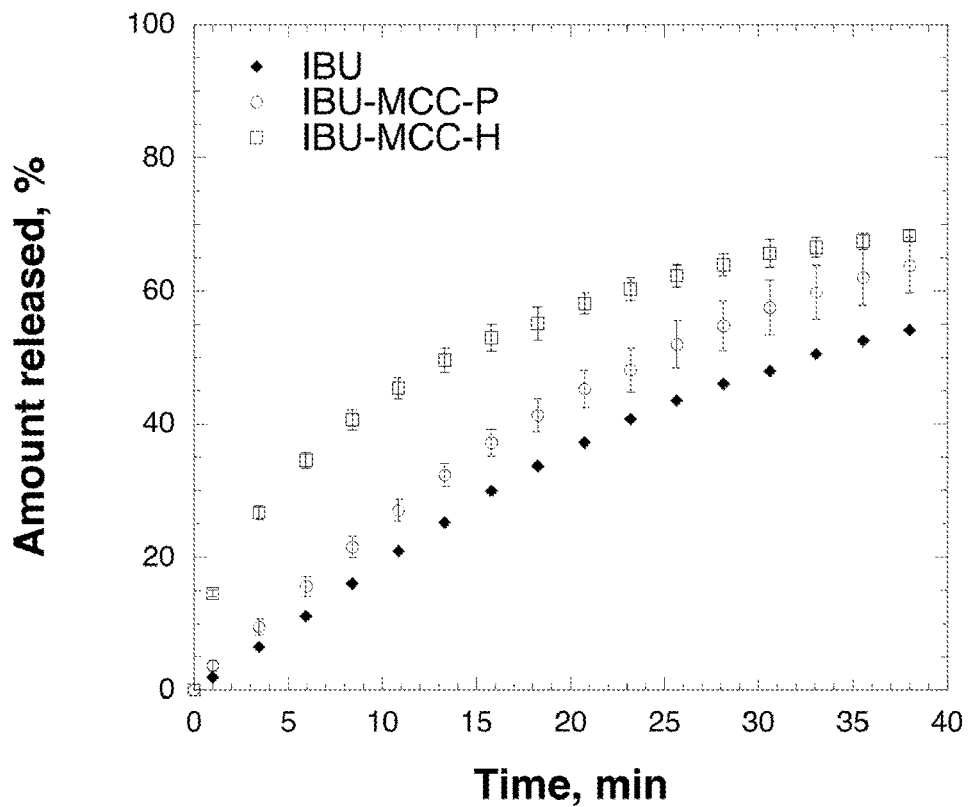
Figure 5B:
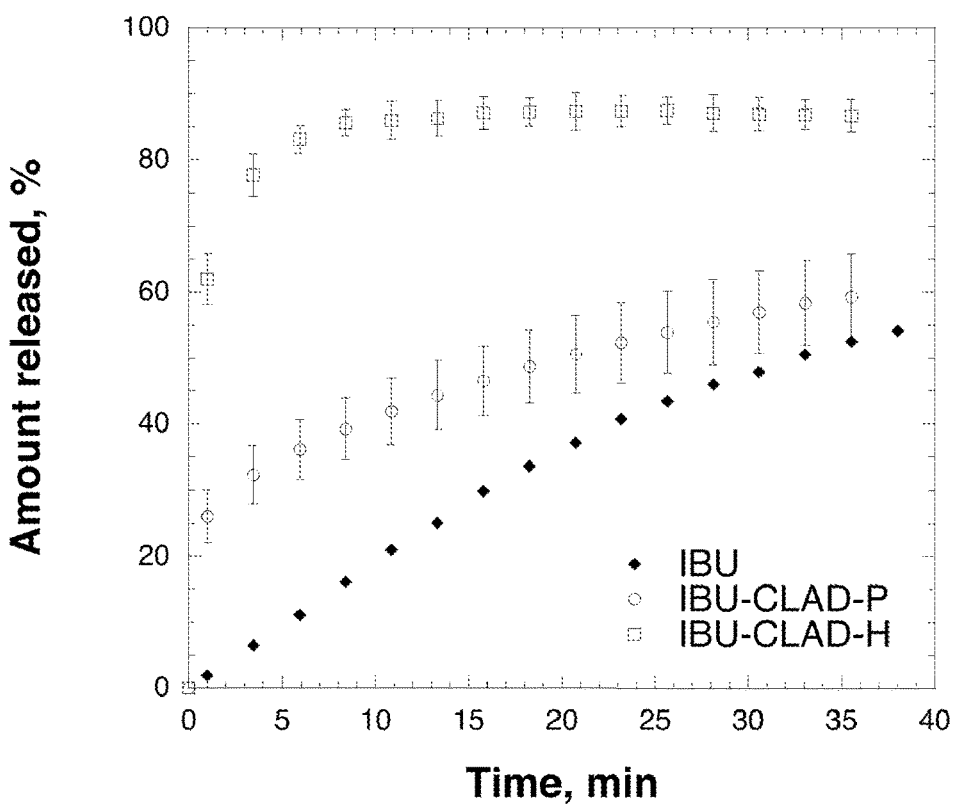

The IBU release from cellulose mixtures was studied using UV-spectroscopy (U1700 Shimadzu, Japan). The concentration of IBU was monitored at λ=222 nm. During each measurement, samples were drawn every 2 minutes during 38 minutes. An IBU-MCC and IBU-CLAD mixtures of about 50 mg with 1:9 drug-to-cellulose weight ratio were used. The drug release was performed in 250 ml of deionised water. Results are shown in FIG. 5.

Oral Pharmacokinetic Study in Rats

Naive SPF Wistar rats (HanTac:WH strain; 5-6 weeks; 100 g) were used for pharmacokinetic studies performed by oral gavage as the administration route. Samples of ibuprofen (3 mg) with cellulose in 1:9 weight ratio were used. The dose administered to each animal was 30 mg/kg. The formulations were administered by flashing the contents of the powder vial with a total of 2 ml of purified water by oral gavage. On Day 1, blood samples were collected at the following time points in relation to dosing: 0 (pre-treatment), 15, 30, 45, 60, and 120 min after dosing. At each time point 3 animals were sampled (1 animal per sample). The collected blood samples were frozen at −20° C. until analysed.

Analytical Procedure

The liquid chromatography system used was a LC-10AD pump with a SIL-HTc autosampler (Shimadzu, Kyoto, Japan) and a HyPurity C18 column (3 μm particle size, 50×4.6 mm from Thermo Scientific, MA, USA) with a guard column (HyPurity C18 column, 3 μm particle size 10×4.0 mm. from Thermo Scientific, MA, USA). For detection a Quattro Ultima [Waters, Milford, Mass., USA operated in selected reaction monitoring (SRM) mode with negative electrospray ionization was used. Data analysis was performed using Masslynx 4.1 software (Micromass, Manchester, UK)].

Quantitation was performed using multiple reaction monitoring (MRM) mode to monitor product ion (m/z) transitions. Ibuprofen and ibuprofen-D3 SRM transitions were m/z 204.9.160.9 and m/z 207.9.163.9, respectively. The source dependent parameters maintained for ibuprofen and ibuprofen-D3: 3.8 kV; source temperature: 125° C.; desolvation temperature: 450° C.; cone gas flow; 35 L/h and desolvation gas flow: 1000 L/h. Cone voltage (V) and collision energy (eV) were 35 and H, respectively for both ibuprofen and ibuprofen-D3.

Several mobile phase A candidates varying in pH were tested to achieve the most optimal reverse phased HPLC separation such as 0.1% formic acid, 0.005% formic acid and 5 mM ammonium acetate. The latter was selected. HPLC separation was performed using 5 mM ammonium acetate as a mobile phase A (MPA) and 5 mM ammonium acetate in 90:10 (v:v) acetonitrile:water as mobile phase B (MPB). The flow rate was 0.80 mL/min and the column temperature was RT ° C. Isocratic elution with 45% MPB was used. The autosampler temperature was 4° C. and the injection volume was 10 μL. The retention time for ibuprofen and ibuprofen-03 was 2.07 min and the total run time was 4 min. A basic autosampler wash, 50:50 (v:v) water:methanol, was used to reduce carryover.

Acetonitrile, methanol, ammonium acetate and formic acid were purchased from Merck (Darmstadt, Germany). The water was purified using a Milli-Q system (Millipore, Bedford, Mass.).

Calibration Standards

Ibuprofen (MW206.28 g/mol) stock solution corrected for purity and salt form was prepared in duplicate (IBU #Weight #1 9.71 mg in 5 ml DMSO, 9.41 mM and IBU #Weight #2 5.26 mg in 5 ml DMSO, 5.0999 mM) in dimethyl sulfoxide. Ibuprofen-D3 (MW209.28 g/mol) stock solution (5.14 mg in 5 ml DMSO, 4.912 mM) was also prepared in dimethyl sulfoxide. All stock solutions were stored at −20° C. Intermediate stock solutions in acetonitrile were kept at 4° C.

Calibration standards were prepared by spiking blank plasma from three male Sprague-Dawley rats with ibuprofen. Calibration standard concentrations were initially selected as 5.1, 10.2, 51, 102, 510, 1020, 1530, 1785, 2040 and 5100 nM. Due to unexpectedly high concentration of ibuprofen in several samples additional calibration standards were prepared as 10200, 20400, 15300, 51000, 76500 and 100000 nM Calibration-standards were stored at −20° C. Quadratic regression analysis with 1/y weighing was performed to quantify the concentration of the standards. The determination coefficient (R2) was greater than or equal to 0.99.

Analytical Sample Preparation

Prior to analysis, all frozen pre- and post-treatment samples and calibration standard samples were thawed and allowed to equilibrate at room temperature. To an aliquot of 50 µL of plasma sample 100 µL of ice-cold 0.1% formic acid in acetonitrile spiked with 200 nM ibuprofen-D3 was added. Further samples were vortexed for 20 s and centrifuged at 10.000 g for 3 min at room temperature. One hundred µL of the supernatant was mixed with 100 µL mobile phase A (5 mM ammonium acetate followed by vigorous vortexing and centrifugation at 10.000 g for 1 min. Ten µL were injected into the column.

Data Review

All chromatograms were reviewed to ensure that chromatographic peak shape and peak integration was satisfactory. Run acceptance criteria were set prior the analysis based on the results from calibration standards.

Results

Figure 6:
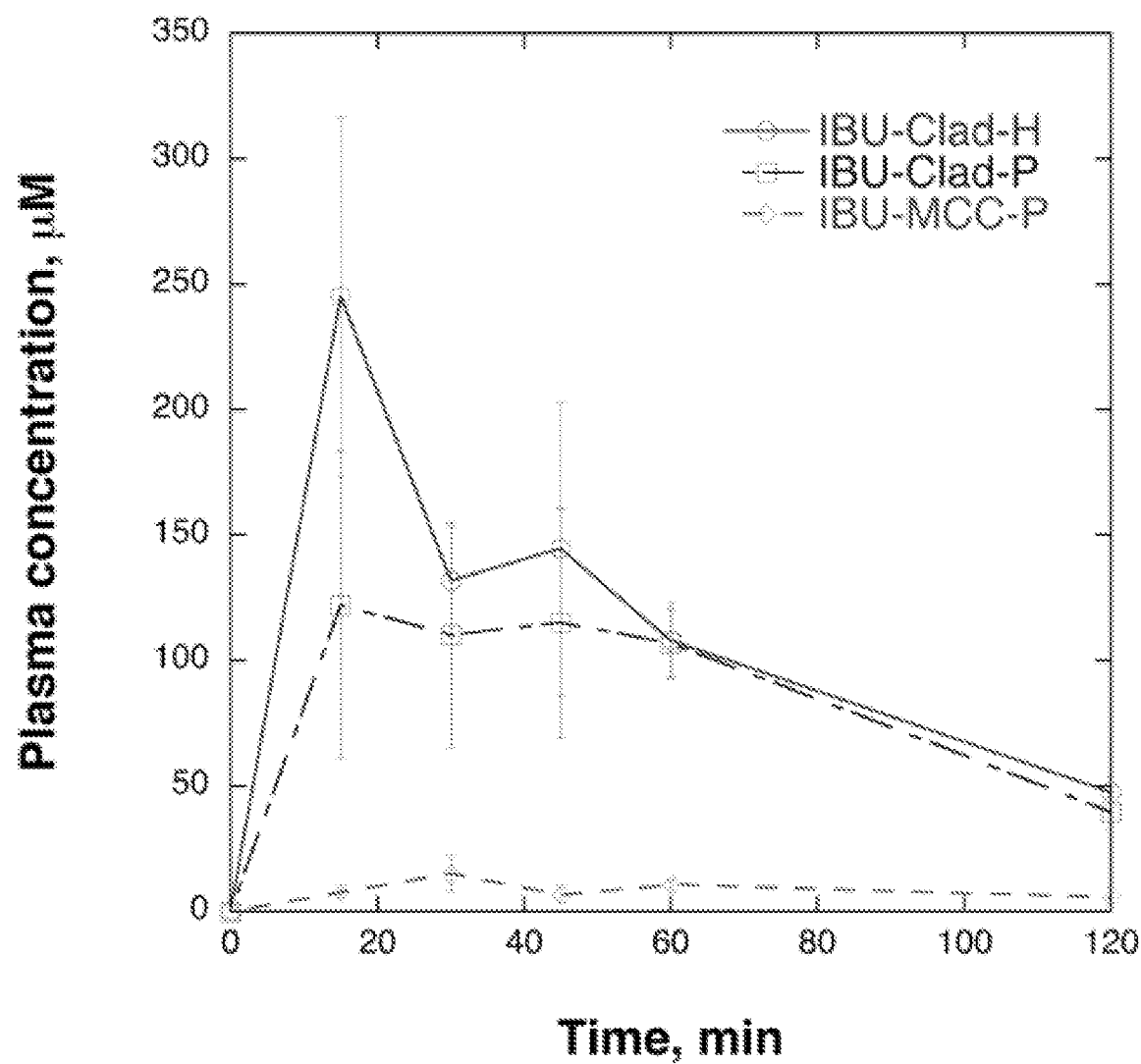

Table 4 summarizes the results of the pharmacokinetic study in rats based on the results in FIG. 6. The data support the improved bioavailability and shortened peak plasma concentration time for the heated IBU-CLAD mixture.

TABLE 4

IBU 30 mg/kg in rats PK parameters. The results are average of 3 measurements with standard error.

| Group | $AUC_{0-t}$ min (µg ml$^{-1}$) | $AUC_{0-\infty}$ Min (µg ml$^{-1}$) | MRT, min | $T_{1/2}$, min |
|---|---|---|---|---|
| IBU-MCC (physical mixture) | 197.0 ± 20.8 | 419.9 ± 328.3 | 192 ± 202 | 133 ± 140 |
| IBU-CLAD (physical mixture) | 1912.8 ± 136.3 | 2479.1 ± 165.4 | 87 ± 11 | 60 ± 7 |
| IBU-CLAD (heated mixture) | 2323.7 ± 170.1 | 3026.0 ± 186.4 | 85 ± 11 | 59 ± 8 |

MRT: mean residence time

Example 2—Flufenamic Acid (FFA)

Product Preparation

Physical mixtures of FFA and cellulose (MCC or CLAD) were prepared by blending the drug substance with the cellulose. Unless otherwise stated, the weight ratio between the FFA and cellulose was 1:9. The surface area of the cellulose was found to be 98.79 m$^2$/g (as measured by N$_2$ gas adsorption technique according to the Brunauer Emmett Teller (BET) method). Typically, in a glass vial 5 mg of FFA was mixed with 45 g of the cellulose using a Vortex mixer for 15 minutes.

Heated mixtures of FFA and cellulose (e.g. MCC or CLAD) were prepared by heating the physical mixture above in a sealed vial at 120° C. for 2 hours. All samples were used after 24 hrs from the time of preparation after cooling to room temperature.

DSC

Thermal analysis was performed with TA instrument (Model Q-2000) on both cellulose-drug mixtures and pure substances. Samples were placed inside hermetically sealed aluminium crucibles with punctured lids, in order to avoid overpressure caused by water evaporation. An empty pan was used as a reference. The analysis was conducted in the temperature range from −40° C. to 150° C. with a heating rate of 10° C. min$^{-1}$. N$_2$ gas, at a flow of 50 mL min$^{-1}$, was applied during analysis. Initially the samples were cooled from room temperature to −40° C., then heated to 150° C. and finally cooled to 25° C. again. All of the samples were stored at ambient conditions for 24 hours prior to DSC measurements. For the heated cellulose-FFA mixtures the heating conditions were 120° C. for 2 hours.

Figure 7A:
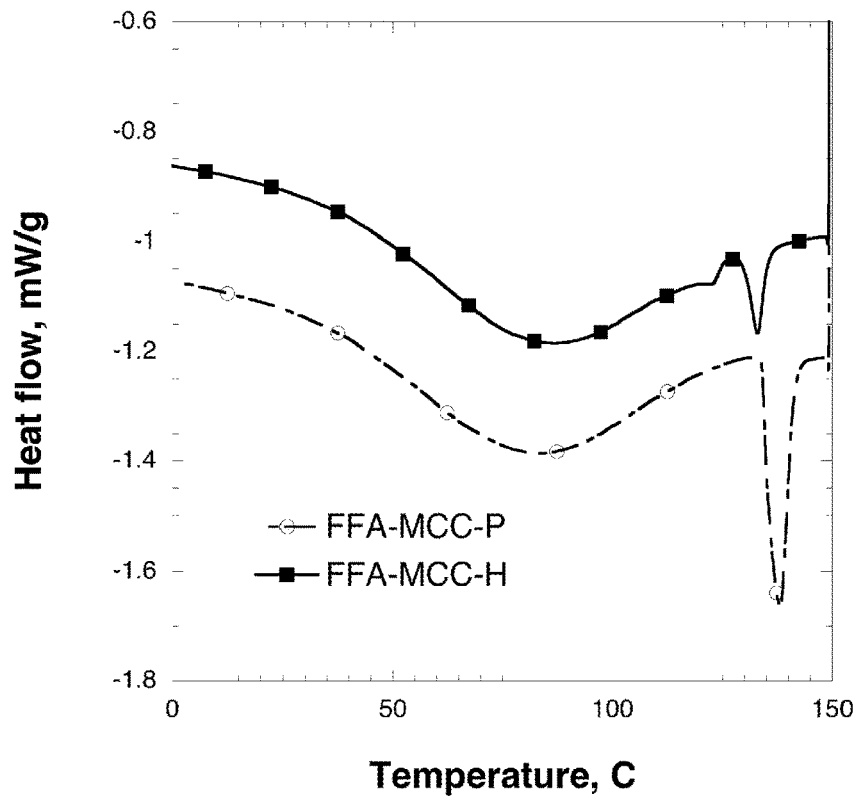
Figure 7B:
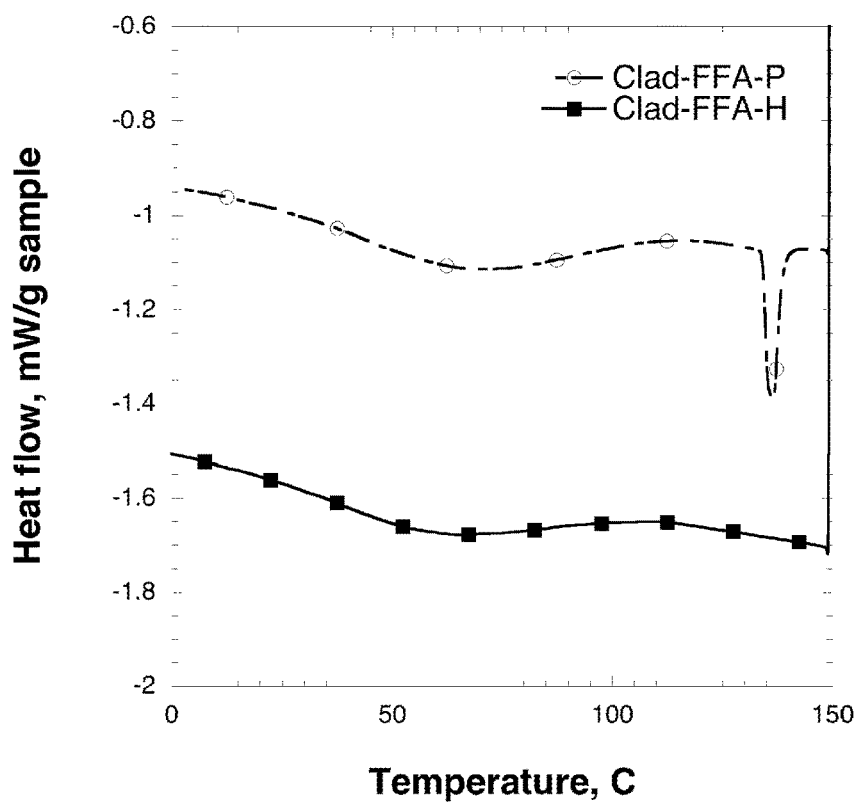
Figure 8A:
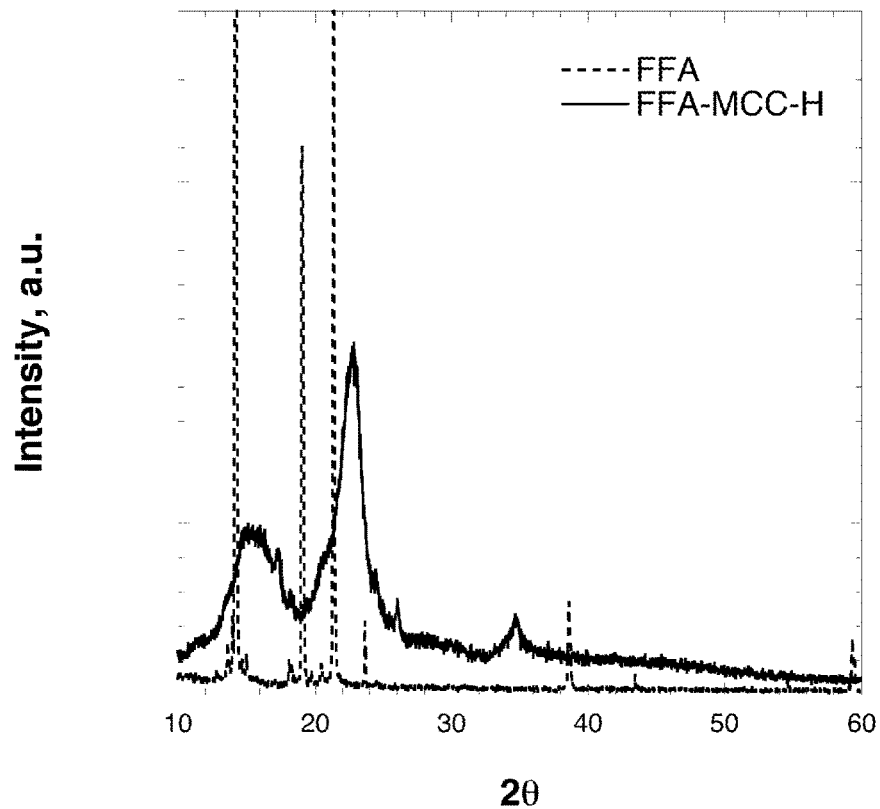
Figure 8B:
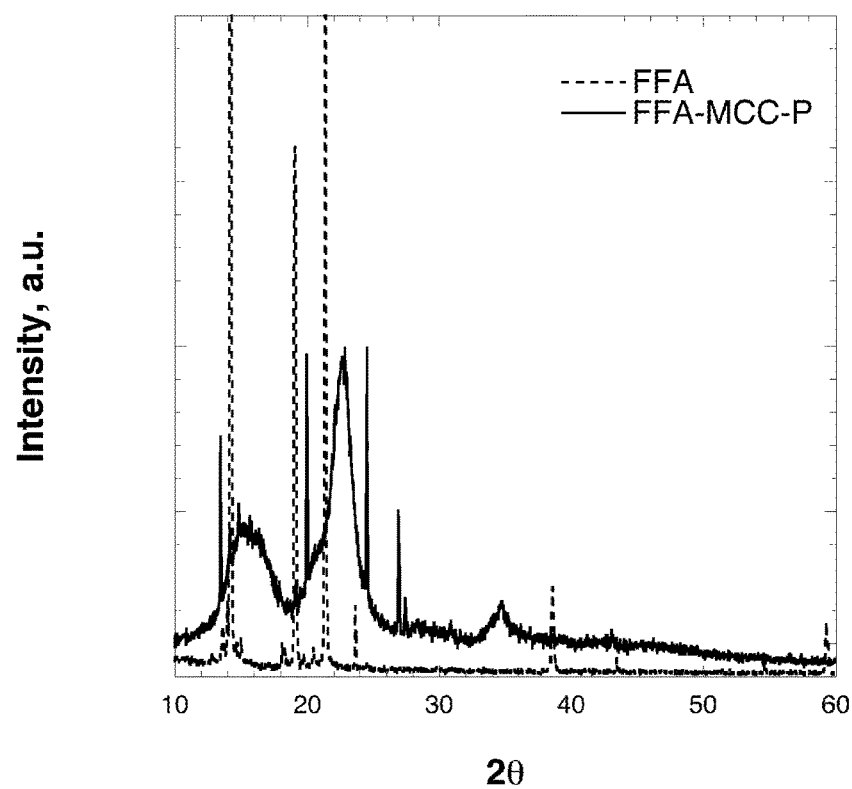
Figure 8C:
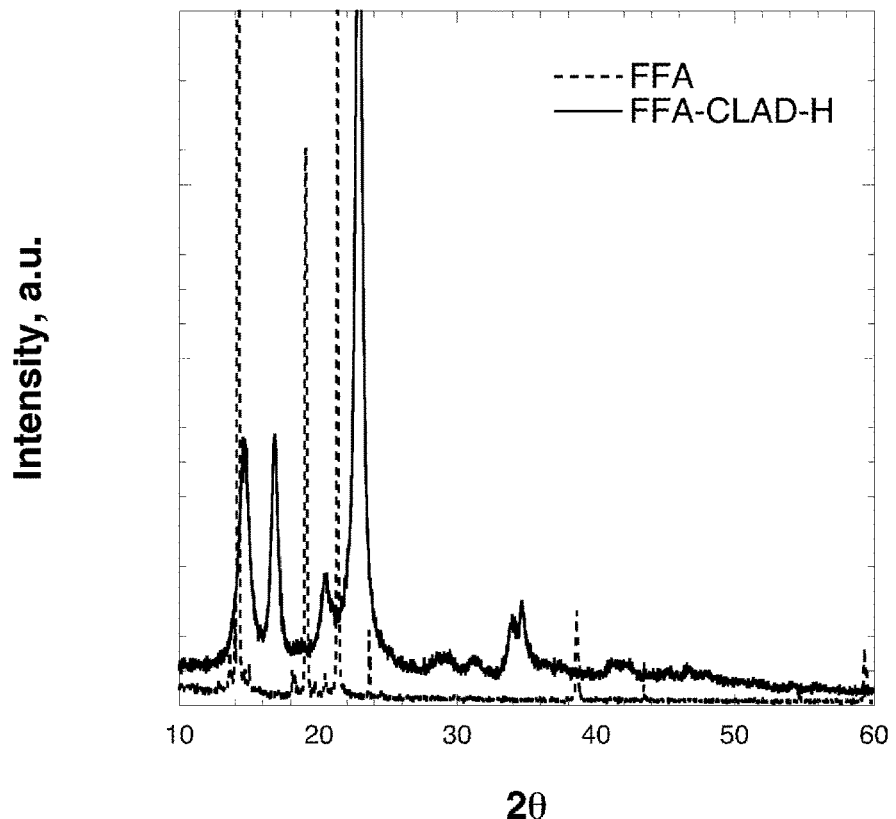
Figure 8D:
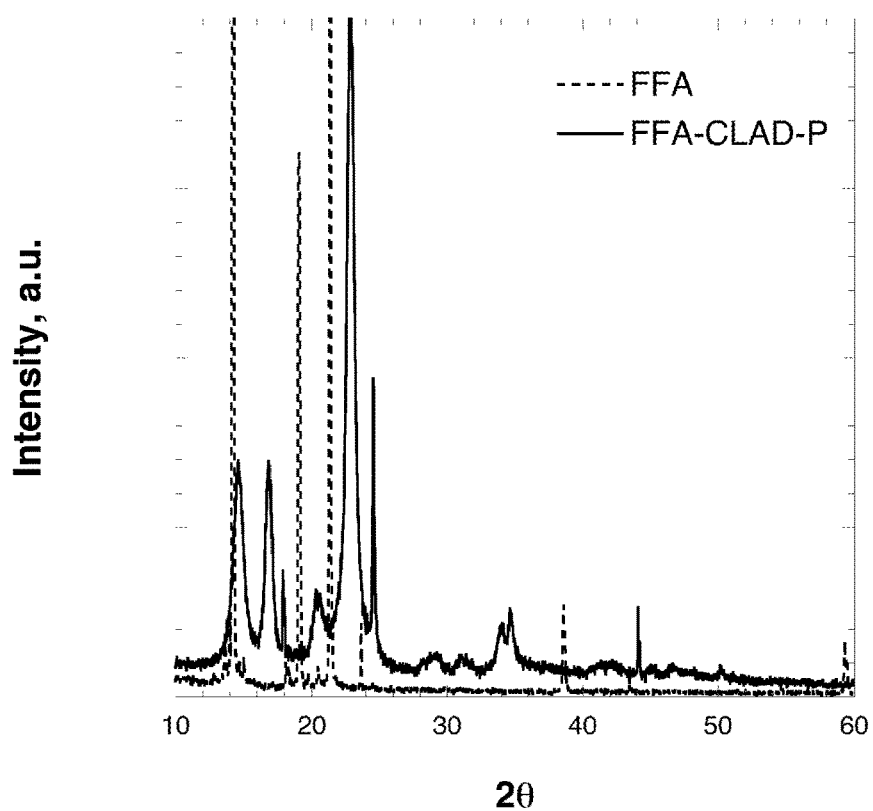
Figure 9A:
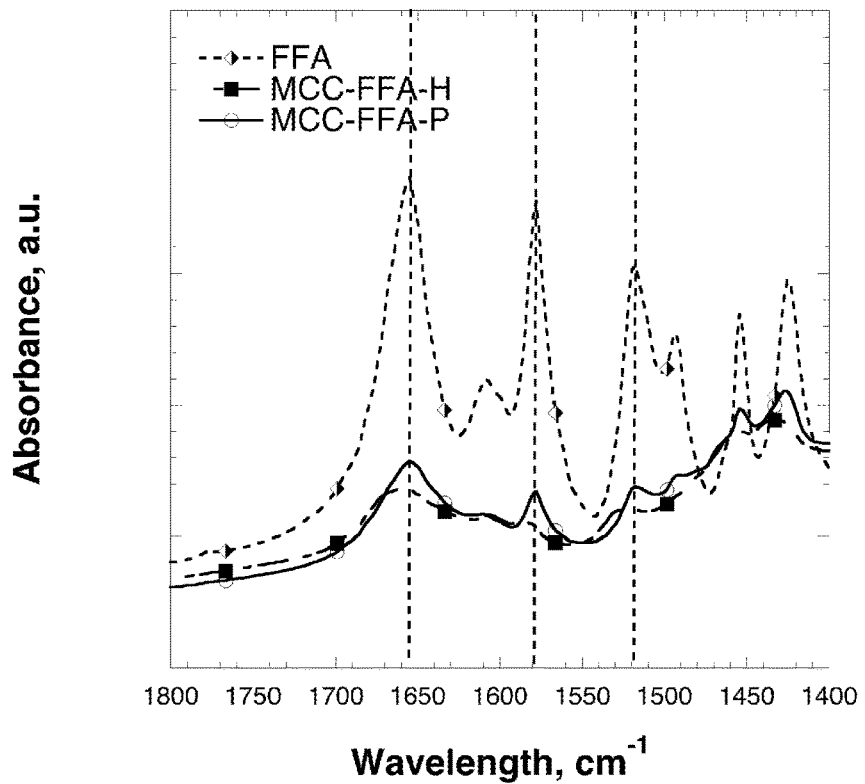
Figure 9B:
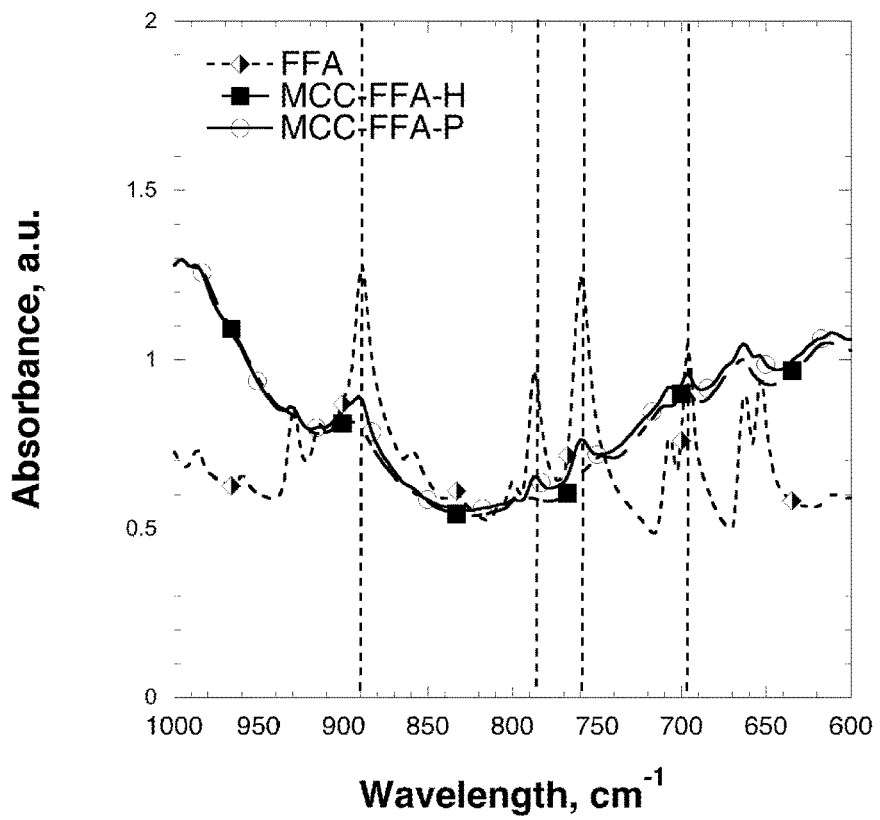
Figure 9C:
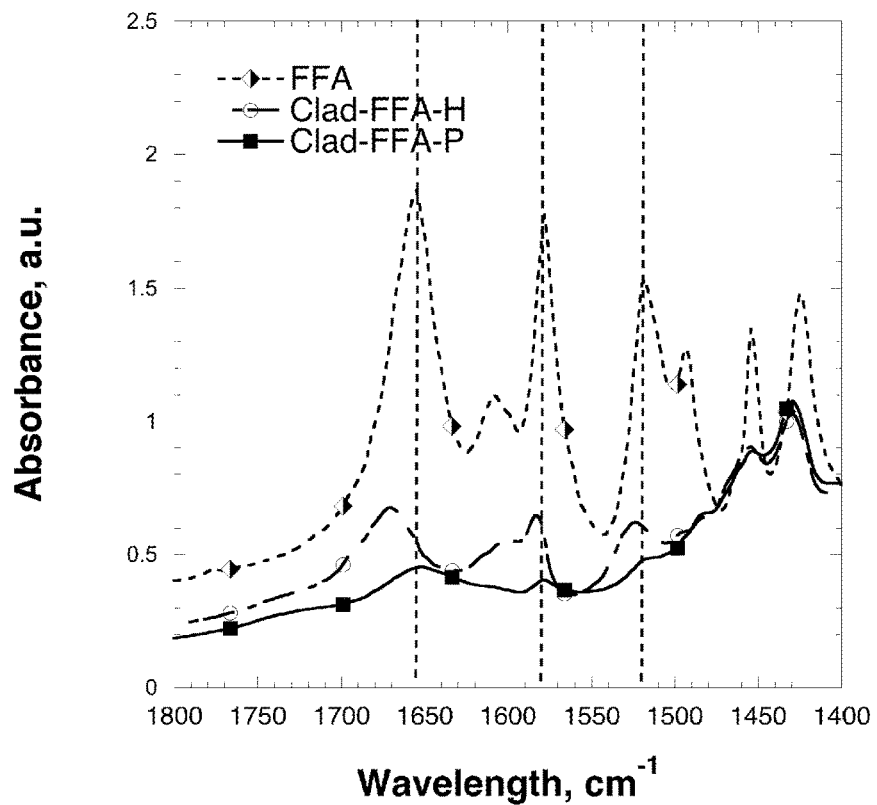
Figure 9D:
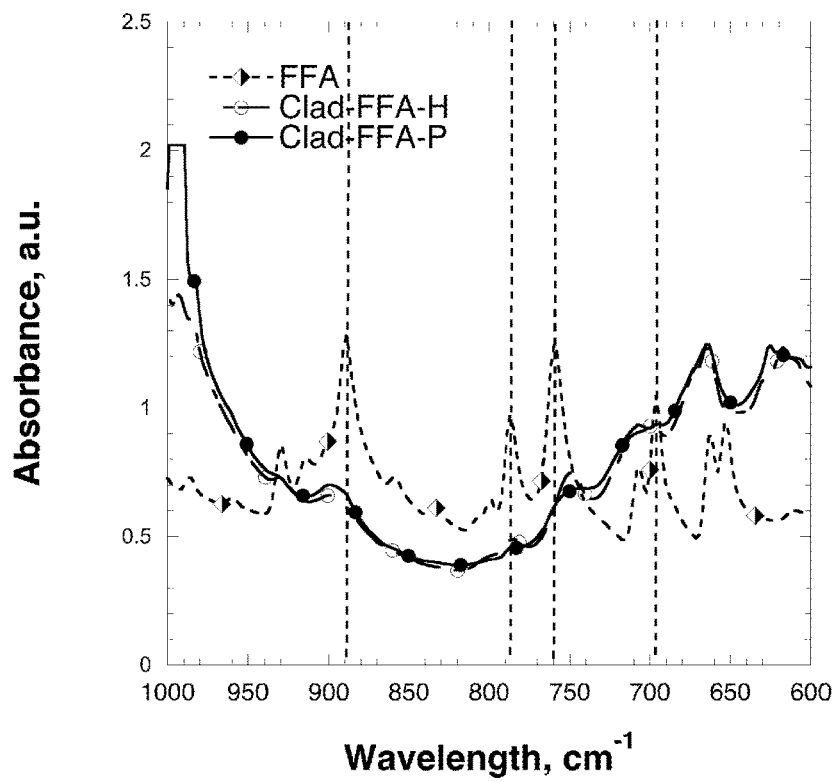

The measurements were performed in triplicate, and the estimated amount of drug in the mixtures was 10 wt %. Results are shown in FIG. 7.

XRD

The characteristic X-ray diffraction patterns were generated using an (D8 Twin-Twin, Bruker) instrument with Bragg-Brentano geometry for both FFA, as a pure drug, and FFA in a blend with different celluloses. The samples were scanned at room temperature (25° C.), CuKα radiation was utilized (λ=1.54 Å) with 2θ angle set between 10 and 60°. Pure FFA (5 mg) was used as the reference and 50 mg of both normal and heated samples of cellulose-FFA blends (approx. 10 wt % FFA in each sample) were scanned once during the analysis. Results are shown in FIG. 8.

FTIR

FTIR analysis was conducted on FFA, as a pure substrate, and FFA in blend with different celluloses. Cellulose-FFA blends from both heated and normal, i.e. unheated, samples were analysed. The FTIR spectra were obtained on a Bruker Tensor 27 (Germany) with KBr pellets. A background scan on air was subtracted from all spectra using the instrument software (Opus 7.0, Bruker, Germany). The approximate sample content in 200 mg KBr pellets was 10 wt % (i.e. 1 wt % drug). The collected data was normalized with respect to C—H stretching vibration at 2897 cm$^{-1}$. The FTIR spectra was collected with the following parameters: 64 scans at a spectrum resolution of 4 cm$^{-1}$ over a range from 4000 to 400 cm$^{-1}$. Results are shown in FIG. 9.

FFA Release

Calibration Standard

Stock solution containing 10 µg mL$^{-1}$ FFA was prepared by dissolving FFA in simulated intestinal fluid (SIF). Various amounts of stock solution between 0.1 mL and 1 mL were transferred to plastic vials and frozen at −27° C. The vials containing stock solution were freeze-dried overnight using a Scanvac CoolSafe 55-4 (LaboGene ApS, Lynge, Denmark). A total of seven working standard solutions with FFA concentration range between 0.1 and 10 μg mL$^{-1}$ were prepared by dissolving the vials containing freeze-dried FFA with 1 mL of a polar solvent, consisting of Acetonitrile-DMSO (4:1, vol/vol). Fluorescence spectral measurements were performed on an Infinite M200 microplate reader by Tecan Gmbh (Austria) equipped with two monochromators (excitation and emission). Black 96-well round-bottom (Corning 96 Round Bottom, Polystyrol) microplates were used. The maximum emission intensity of the drug in the working standards was measured spectrophotometrically at $\lambda_{ex}$=289 with a full band scan from 400 nm to 500 nm.

Dissolution measurements were performed with the rotating paddle technique at 37.0±0.5° C. and 50 rpm with SOTAX (AT7 Smart, Switzerland) dissolution apparatus. Simulated intestinal fluid (SIF, enzyme-free, from Sigma) was selected as the dissolution medium and prepared by diluting 20 mL of concentrated SIF with 480 mL deionized water. Normal and heated mixtures were poured to dissolution vessels with 500 mL dissolution medium and samples of 1 ml were extracted at various time points between 15 minutes and 5 hours (15 min, 30 min, 1 h, 2 h, 3 h, 4 h and 5 h). A total of seven samples with a volume of 1 mL was collected for each cellulose-FFA formulation and passed through a syringe filter into 2 ml plastic vials. The vials were frozen at −27° C. and further freeze-dried. The vials containing the freeze-dried FFA were filled with 1 mL Acetonitrile-DMSO (4:1, vol/vol) solvent and manually shaken until the collected FFA was dissolved. Two parallel measurements were performed for each formulation. Spectrofluorometric analysis together with previously described regression analysis was used to estimate the concentration of released FFA at different time points.

Results

Figure 10A:
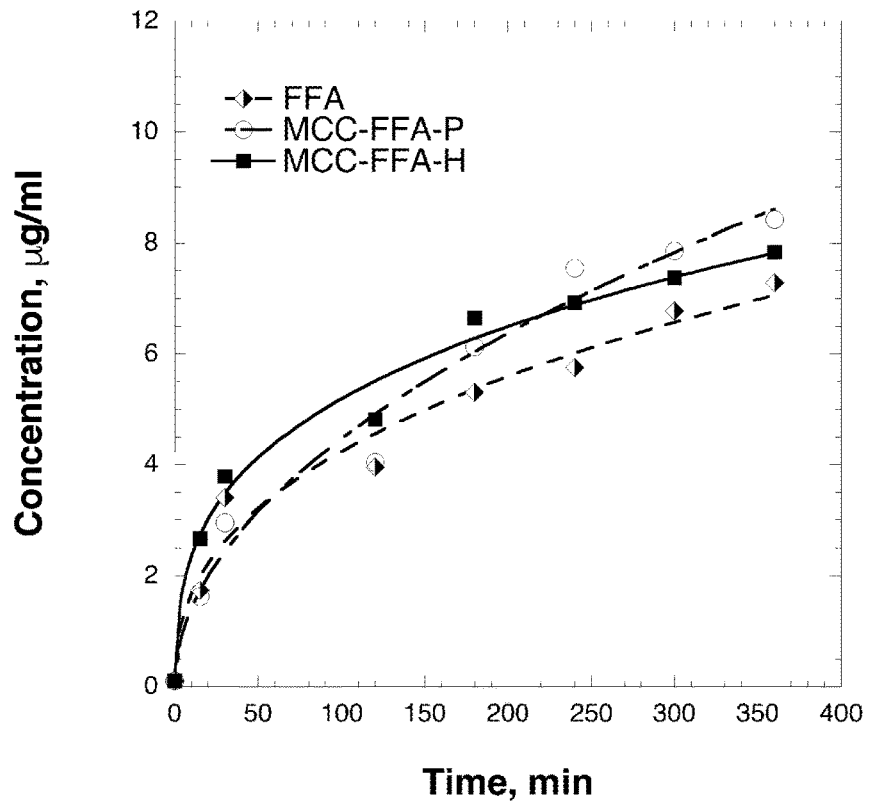
Figure 10B:
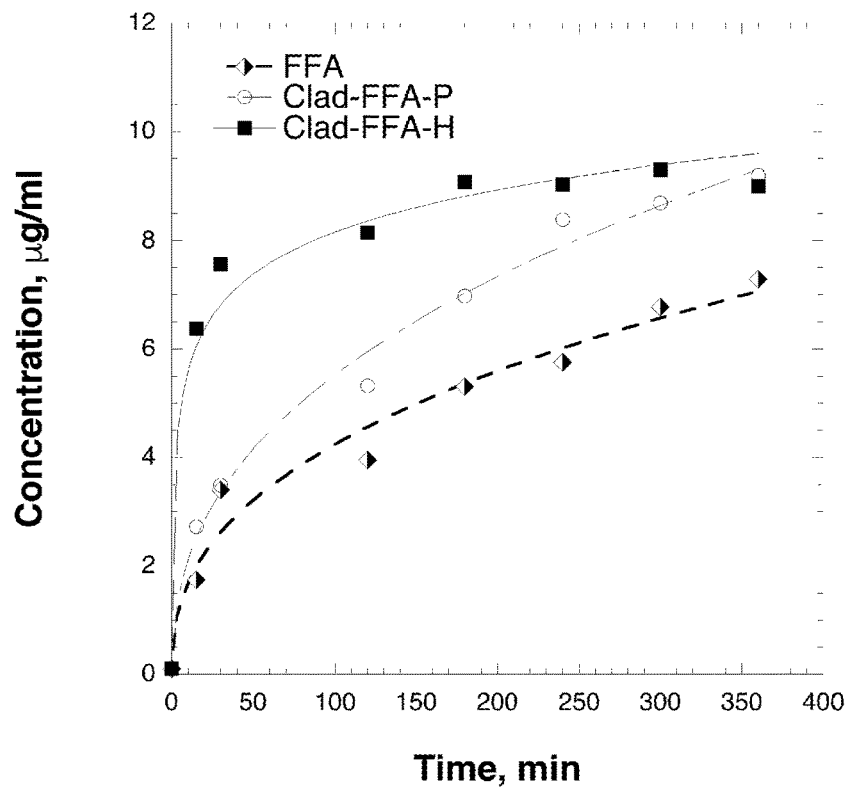
Figure 11A:
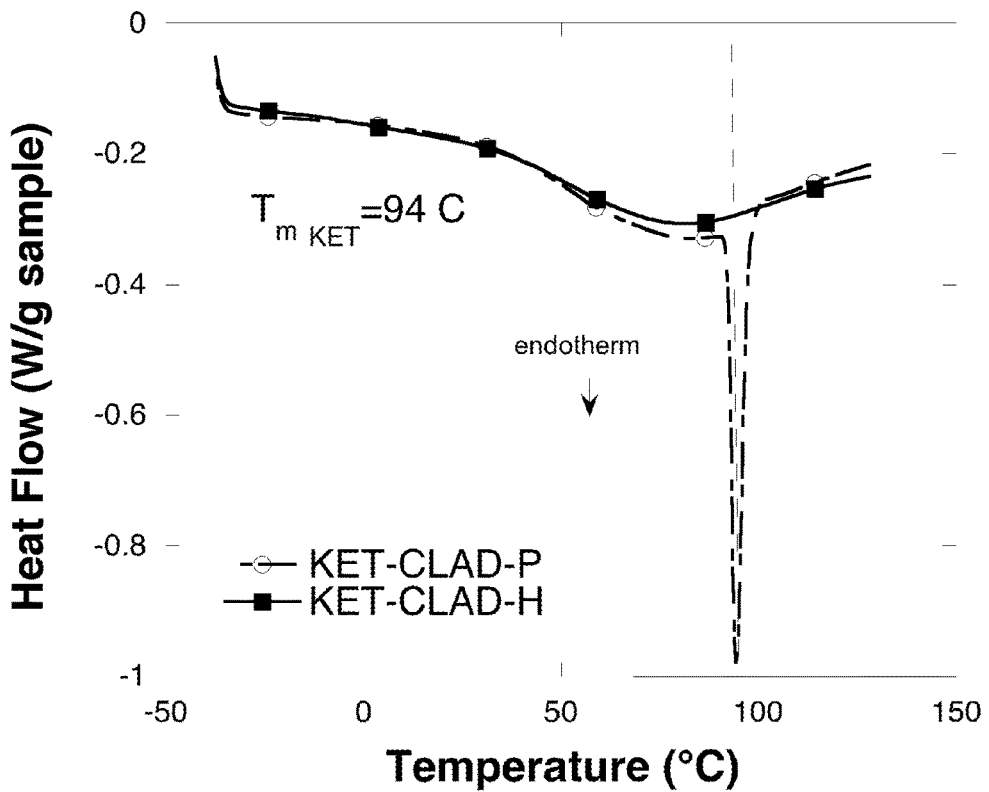
Figure 11B:
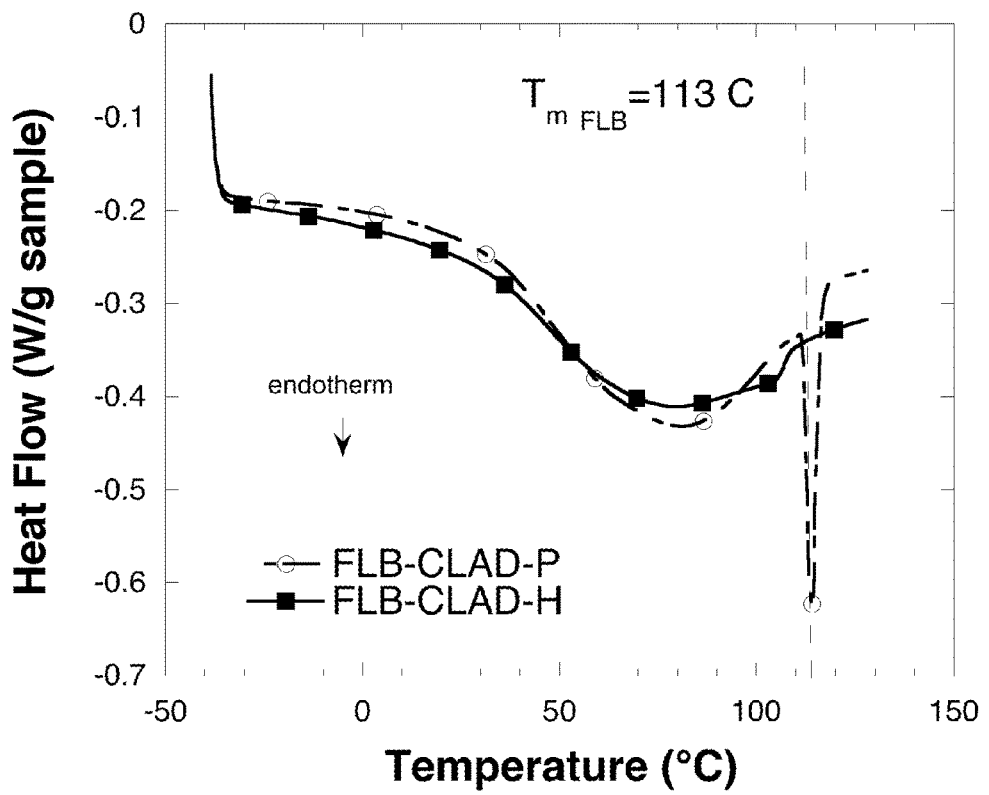
Figure 11C:
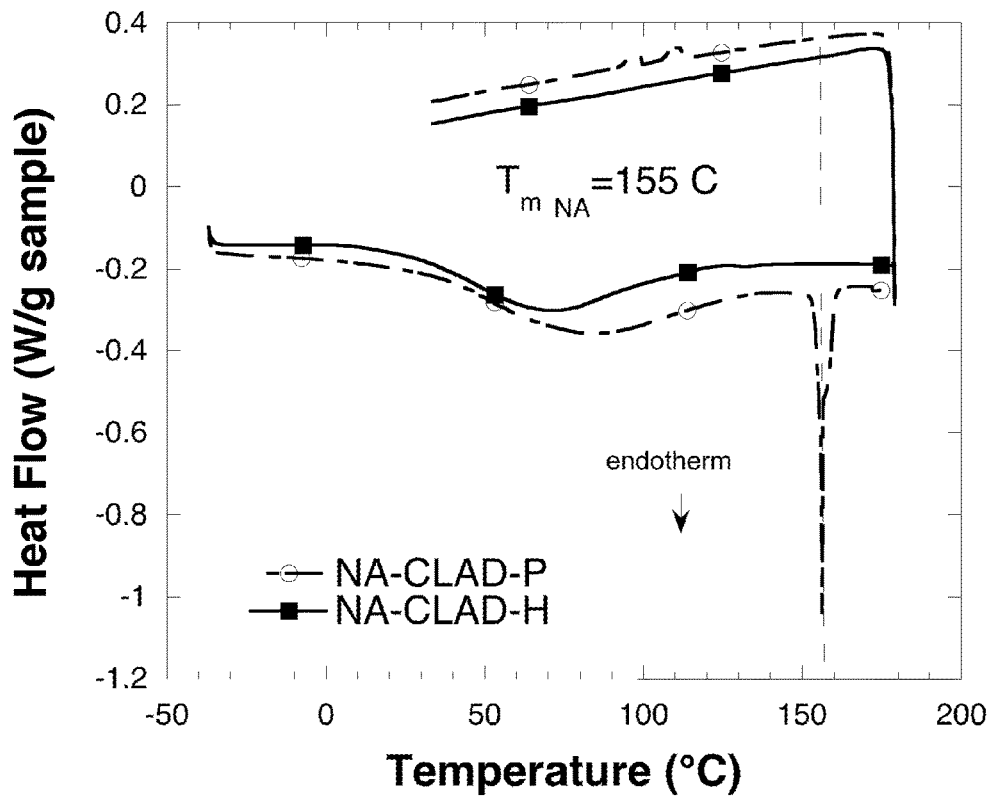
Figure 11D:
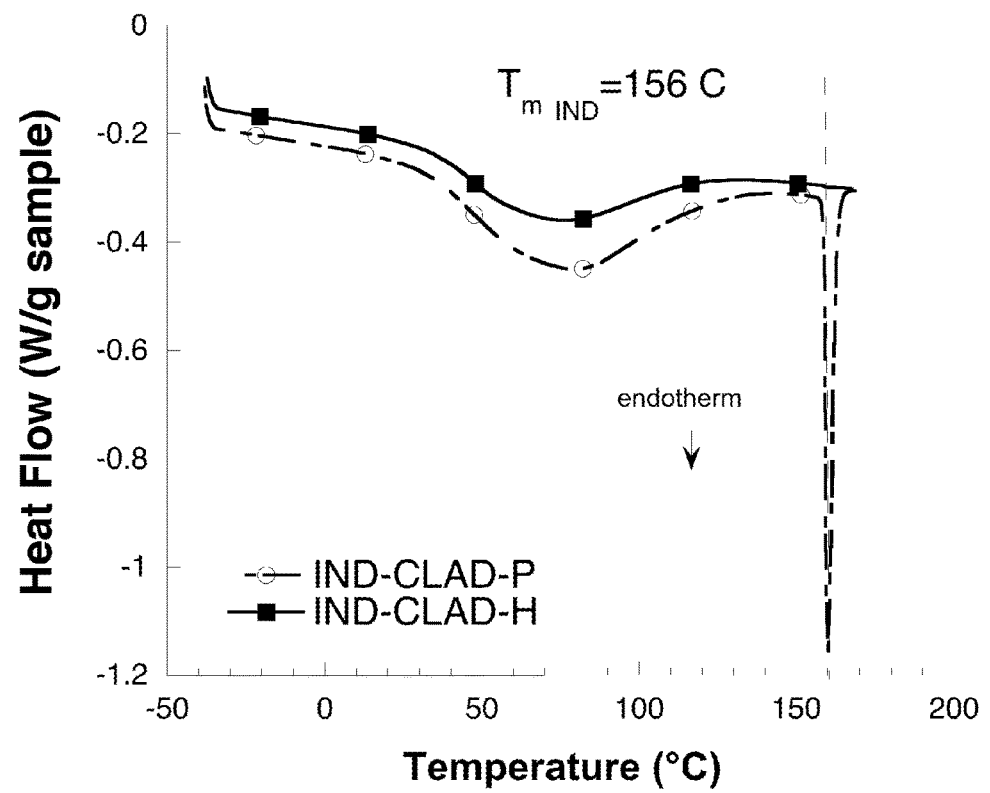
Figure 11E:
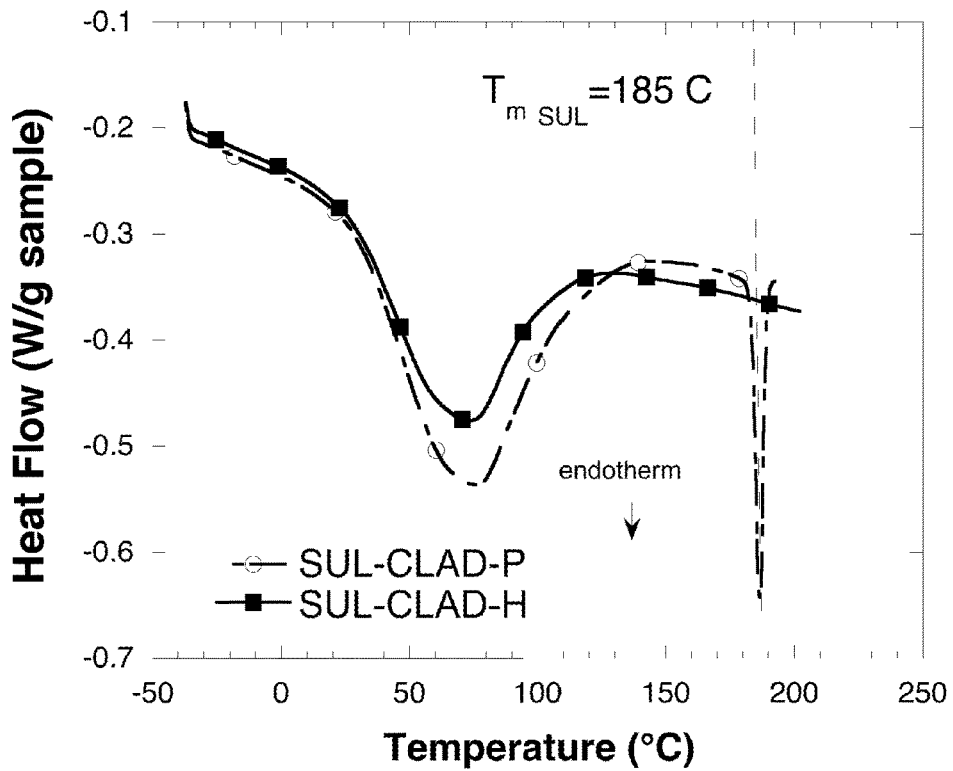
Figure 11F:
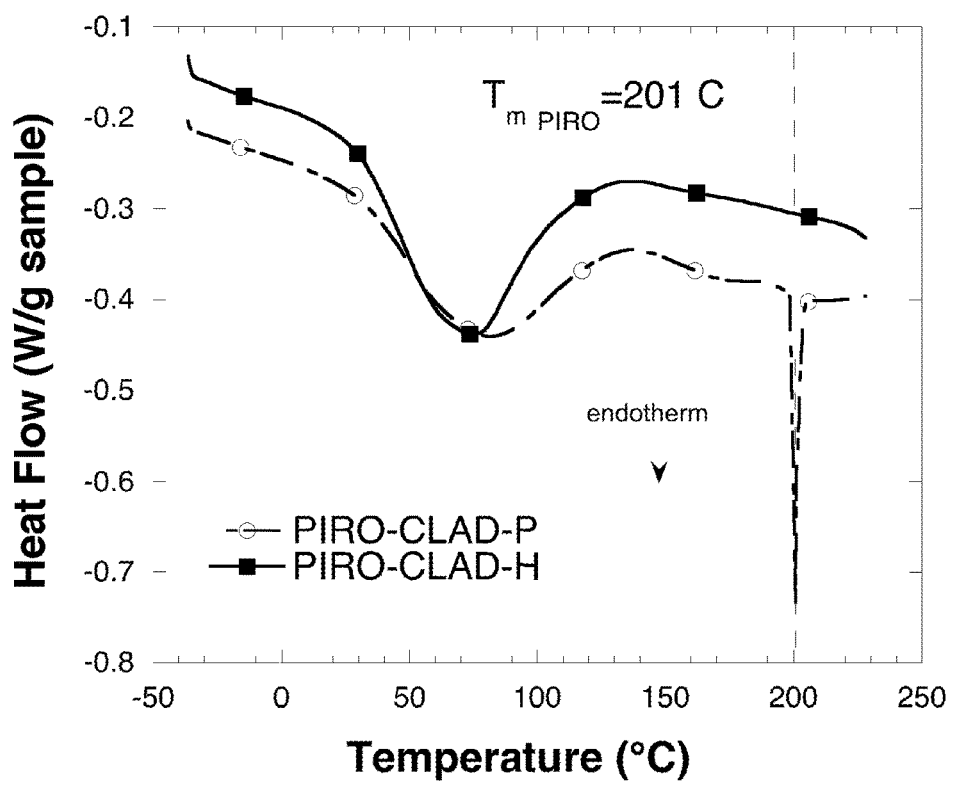
Figure 11G:
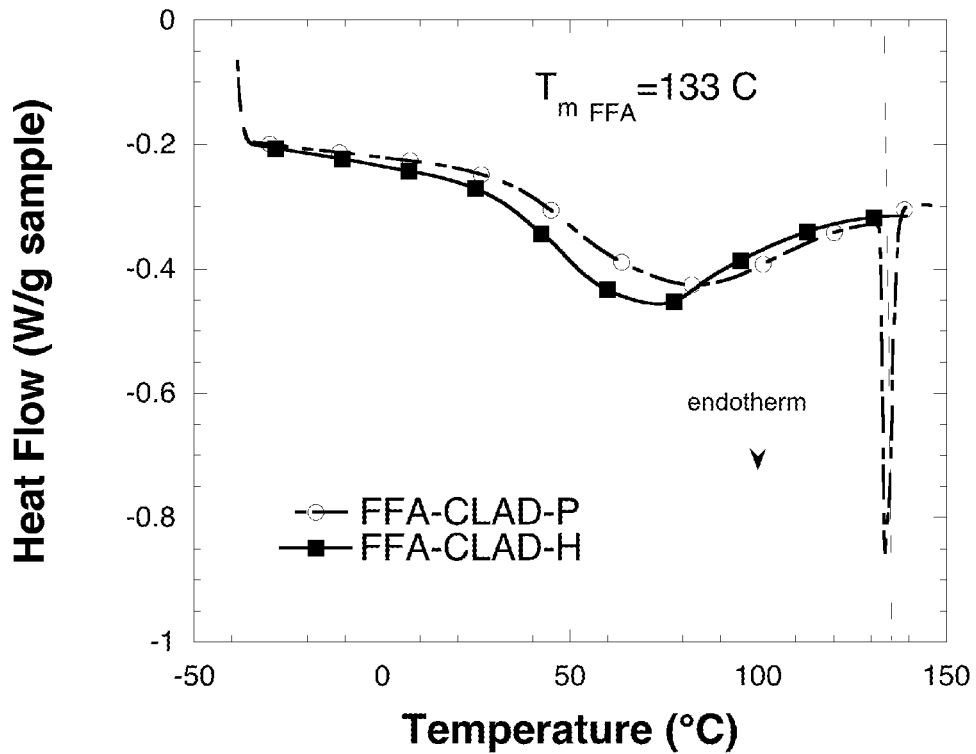
Figure 11H:
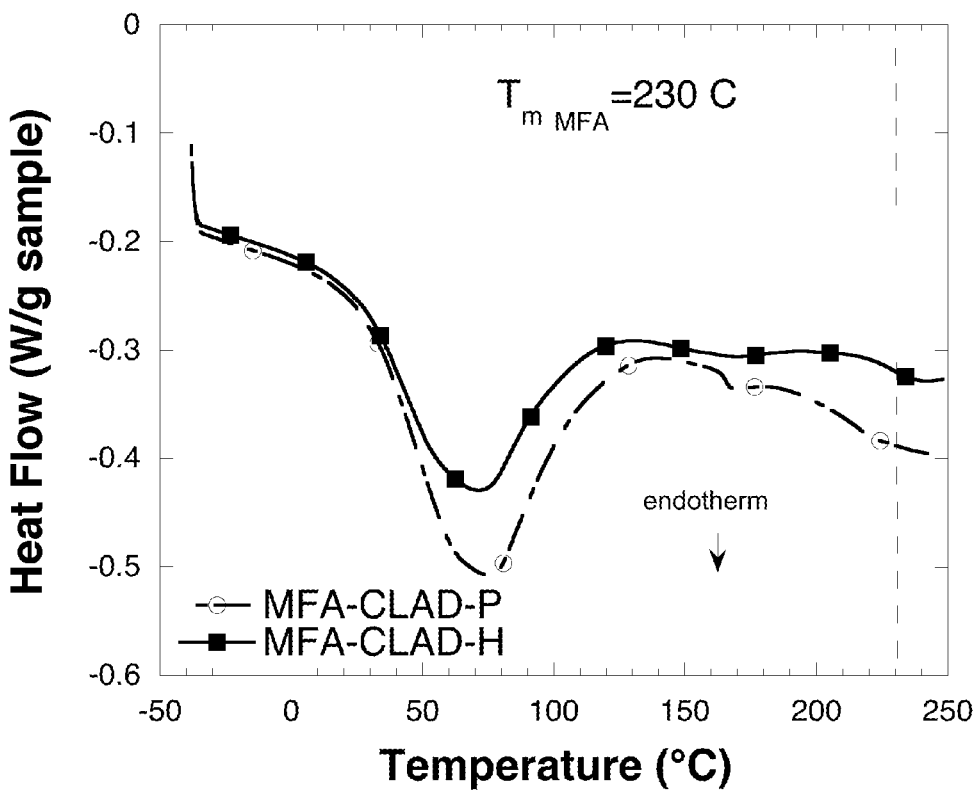

Table 5 shows the enthalpies of FFA mixtures based on the analysis of results presented in FIG. 10. It is seen from Table 5 that while the degree of crystallinity of FFA is suppressed in all mixtures with both celluloses it is only for the heated FFA-CLAD sample that FFA is fully amorphous.

In all these cases a similar trend was observed during solid state characterization of CLAD mixtures:

in DSC profiles, no melting endotherm was observed for heated drug-CLAD mixtures as compared to the physical drug-CLAD mixture and pure crystalline drug;

in XRD profiles, the sharp peaks corresponding to crystalline drug disappear or are essentially depressed for the heated drug-CLAD mixture as compared to the physical drug-CLAD mixture and pure crystalline drug;

in FTIR profiles, shifts in the position for C=O group as well as significant distortion of peaks for aromatic vibrations were observed in the heated drug-CLAD mixture as compared to the physical drug-CLAD mixture and pure crystalline drug.

Heated mixtures of these isopropionic acid derivatives, enolic acid derivatives, isopropionic acid derivatives, or anthranilic acid derivatives with nanocellulose each showed a significant degree of molecular rearrangement and with the drug becoming amorphous.

Example 4—Naproxen, progesterone and β-estradiol

Naproxen, progesterone, and β-estradiol were used as supplied by Sigma Aldrich. *Cladophora* cellulose was used as supplied by FMC Corp.

Product Preparation

Typically, 100 mg blends containing approximately 10% drug (either Naproxen, progesterone or β-estradiol) were prepared by mixing 10 mg drug with 90 mg of cellulose powder in 1 mL glass vials. Additionally, mixtures containing 20% (by weight) drug were made for progesterone, and mixtures containing 20% and 30% (by weight) drug were made for estradiol. The vials were sealed with plastic screw caps and vortexed for 30 seconds. Each cellulose-drug blend was analysed in both heated and unheated (normal) form. In order to form the heated cellulose-drug blends, vials containing the cellulose-drug blends were placed in a preheated oil bath for 2 hours at the same temperature as the melting point of the drug.

TABLE 5

Melting enthalpies of FFA in pure form and in mixtures with different celluloses. Results are presented as averages with standard deviation (n = 3).

| | ΔH$_{melt}$ (J/g$_{mix}$) | T$_{onset}$ (° C.) | T$_{melt}$ (° C.) | Crl$_{FFA}$% |
|---|---|---|---|---|
| FFA | 95.1 ± 3.1 | 133.9 ± 0.1 | 135.0 ± 0.3 | 100 |
| FFA-MCC (physical mixture) | 8.8 ± 3.5 | 134.1 ± 0.0 | 138.0 ± 1.0 | 58 |
| FFA-MCC (heated mixture)$^a$ | 0.5 ± 0.2 | 120.7 ± 1.4 | 123.9 ± 0.7 | 3 |
| | 3.3 ± 0.3 | 130.8 ± 0.7 | 133.2 ± 0.2 | 19 |
| FFA-CLAD (physical mixture) | 4.6 ± 2.3 | 134.1 ± 0.0 | 136.1 ± 0.5 | 29 |
| FFA-CLAD (heated mixture) | 0 | 0 | 0 | 0 |

$^a$Two peaks could be detected at near the melting temperature of FFA in each sample Example 3—Other Active Pharmaceutical Ingredients The invention is further illustrated for other NSAIDs such as ketoprofen, flurbiprofen, naproxen, mefenamic acid, indomethacin, pyroxicam, sulindac. Mixtures of drug and cellulose were prepared in the same manner as described above in respect of Example 1, i.e. for each respective active substance the mixture was heated statically to melting temperature or slightly above for 3 hours. The results of DCS measurements are shown in FIG. 11.

Fourier Transform Infrared Spectroscopy (FTIR)

FTIR spectra were obtained for naproxen, progesterone and β-estradiol (each mixed with cellulose) using the processes described in Example 1. The approximate sample content in 200 mg KBr pellets was 10% (i.e. 1% drug). The collected data was normalised with respect to C—H stretching vibration at 2897 cm$^{-1}$. The FTIR spectra were collected with the following parameters: 32 scans at a spectrum resolution of 4 cm$^{-1}$ over a range from 4000 to 400 cm$^{-1}$.

Thermogravimetric Analysis (TGA)

TGA was conducted on a Mettler TG50 apparatus (10 K min$^{-1}$; 35° C. to 20° C. above the melting point of the drug)

on 10-20 mg samples in aluminium crucibles under a nitrogen atmosphere (60 mL min$^{-1}$). Both normal and heated 10% mixtures were analysed and compared to the pure crystalline substance of corresponding drug content, i.e. 1-2 mg. The temperature in the furnace was continuously monitored, and the heat flow curves were collected both for heating and cooling phase to record melting or re-crystallization events.

The weight normalized enthalpies of melting observed in cellulose-drug mixtures were calculated using the STARe Excellence software (Mettler Toledo) and compared to the weight normalized enthalpy for the pure crystalline drug, to give a rough estimate of the degree of the drug crystallinity ("Crl") as follows.

$$C = \frac{\Delta H_m}{\Delta H_d} \times 100 \quad (1)$$

where $\Delta H_{melt}$ is weight normalised melting enthalpy of the drug in a specific cellulose-drug blend [in Joules/g] and $\Delta H_{drug}$ is the melting enthalpy of a pure crystalline drug [in Joules/g].

X-Ray Diffraction (XRD)

X-ray diffraction patterns were generated using the apparatus described in Example 1. The samples were scanned at room temperature (25° C.), CuKα radiation monochromatized with a graphite crystal was utilized ($\lambda$=1.54 Å) with 2θ angle set between (10 and 45°). Pure drug (about 2 mg) was used as the reference and 10-20 mg of both normal and heated samples of blends (approx. 10% drug in each sample) were scanned once during XRD analysis.

Drug Dissolution Studies

In order to study the release kinetics of naproxen and progesterone in formulations with *Cladophora* cellulose, dissolution measurements were made on normal and heated mixtures and compared to the dissolution of the pure crystalline drug of corresponding drug content. Dissolution rate was determined by the standardized USP paddle method. Release profiles for the drug were created by spectrofluorometric analysis on samples at various time points.

Standard Drug Solutions and Fluorometric Calibration

Stock solutions containing 16 μg mL$^{-1}$ naproxen or 15 μg mL$^{-1}$ progesterone were prepared by dissolving the drug in phosphate buffered saline (pH=7.4 at 25° C.). Various amounts of stock solution (between 0.1 and 1 mL) were transferred to plastic vials. These vials were dried overnight. For naproxen (NAP), a total of six working standard solutions with NAP concentration range between 2 and 12 μg mL$^{-1}$ were prepared by dissolving the contents of the vials with 1 mL of pure acetonitrile. For progesterone (PRO), the same method was used but with seven working solutions with PRO concentration range between 1.5 and 9 μg mL$^{-1}$.

Fluorescence spectral measurements were performed on Infinite M200 Tecan (Austria) microplate reader equipped with two monochromators (excitation and emission) and UV Xenon light source. Black 96-well round-bottom microplates (Corning 96 Round Bottom, polystyrol) were used. The excitation wavelength was set at $\lambda_{ex}$=230 nm. The emission intensity of the drug was scanned between 280 and 400 nm. The maximum emission intensity for naproxen was at $\lambda_{em}$=350 nm and for progesterone at $\lambda_{em}$=300 nm.

Drug Release

Dissolution measurements were performed using apparatus as described in Example 2. Phosphate buffer was selected as the dissolution medium. Five hundred mL of the prepared solution were used per beaker. Normal and heated mixtures were poured into the beakers containing the dissolution medium. Samples of 1 mL were extracted at various time points between 5 minutes and 6 hours. A total of twelve samples was taken per run. The contents of each sample were evaporated until all of the water had gone. The solid residue was re-dissolved in 1 mL using acetonitrile. Two parallel measurements were performed for each formulation. The dissolution rate was estimated from the average intensities of two measurements using the calibration curve as described above.

Results

For naproxen, the following observations were made:
  in DSC profiles, a much smaller melting endotherm was observed for heated and normal drug-CLAD mixtures as compared to the pure crystalline drug;
  in XRD profiles, the sharp peaks corresponding to crystalline drug disappear or are essentially depressed for the heated and normal drug-CLAD mixtures as compared to the pure crystalline drug. There is also a slight reduction in the sharpness of peaks corresponding to crystalline drug in the heated drug-CLAD mixture as compared to the normal drug-CLAD mixture;
  in the FTIR profile for naproxen, shifts in the positions for the C=O group were observed in the heated drug-CLAD mixture as compared to the physical drug-CLAD mixture and pure crystalline drug.

Figure 12:
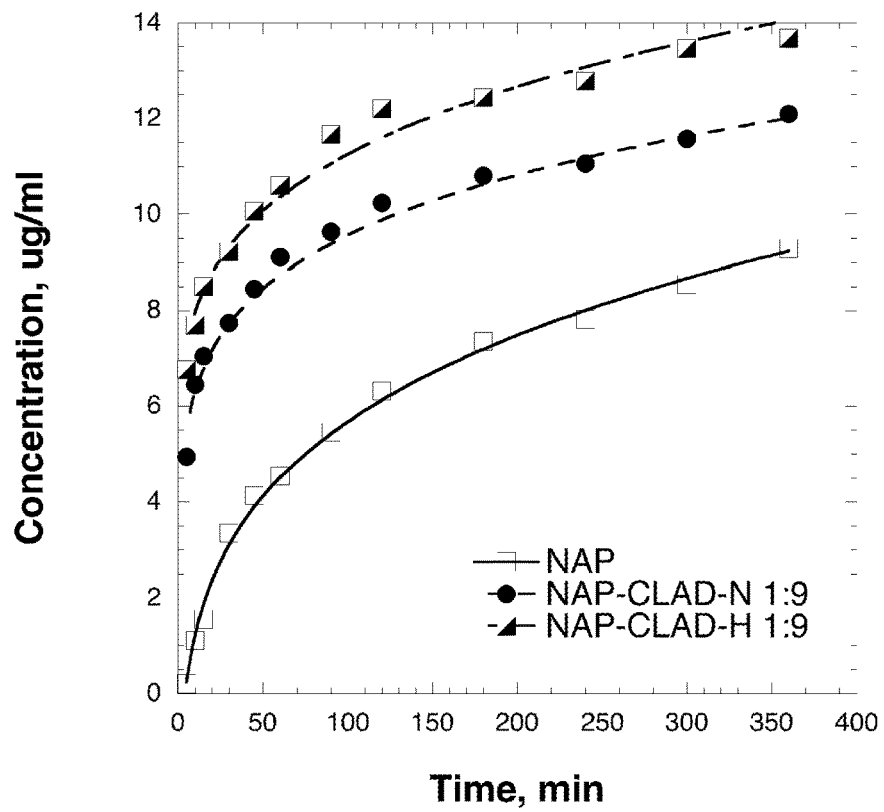
FIG. 12 shows the in vitro dissolution profile of NAP alone and in mixtures with cellulose (10% NAP by weight relative to the mixture)

The drug release measurements are shown in FIG. 12. The results show substantially accelerated release and dissolution of drug from the drug-cellulose mixtures as compared to dissolution of the pure drug. Dissolution was fastest for the drug-CLAD samples.

Table 6 shows the enthalpies of naproxen (NAP) mixtures based on the analysis of results obtained. It is seen from Table 6 that the degree of crystallinity of NAP is suppressed in both mixtures with cellulose. The heated NAP-CLAD sample shows the greatest degree of amorphicity for NAP.

TABLE 6

Melting enthalpies of NAP in pure form and in mixtures with CLAD cellulose.

| | $\Delta H_{melt}$ (J/g) | $T_{onset}$ (° C.) | $T_{peak}$ (° C.) | Crl$_{NAP}$ (%) |
|---|---|---|---|---|
| NAP melt. | −193.6 | 153.2 | 156.1 | 100 |
| NAP recryst. | 147.5 | 123.7 | 124.6 | 76 |
| NAP-CLAD-N 1:9 | −2.52 | 142.7 | 156.8 | 1.30 |
| NAP-CLAD-H 1:9 | −0 | 140.9 | 154.7 | 0 |

For progesterone, the following observations were made:
  in DSC profiles, a much smaller melting endotherm was observed for the heated and normal drug-CLAD mixtures as compared to the pure crystalline drug;
  in XRD profiles, the sharp peaks corresponding to crystalline drug disappear or are essentially depressed for the heated and normal drug-CLAD mixtures as compared to the pure crystalline drug;
  in the FTIR profile for progesterone, a shift in the position for the C=O group as well as significant distortion of peaks for aromatic vibrations were observed in the heated drug-CLAD mixture as compared to the pure crystalline drug. The shift in position for the C=O group was greatly reduced for the physical drug-CLAD mixture.

Figure 13:
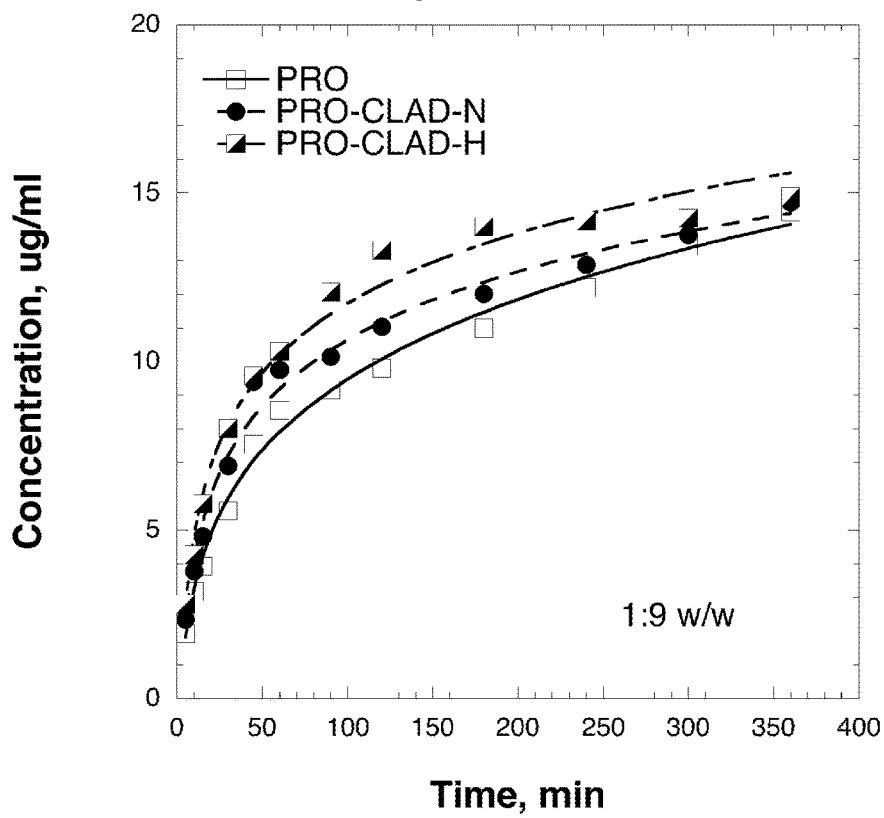
FIG. 13 shows the in vitro dissolution profile of PRO alone and in mixtures with cellulose (10% PRO by weight relative to the mixture)

The drug release measurements are shown in FIG. 13. The results show accelerated release and dissolution of drug from the drug-cellulose mixtures as compared to dissolution of the pure drug. Dissolution was fastest for the drug-CLAD samples. The results showing accelerated drug release and dissolution for progesterone are interesting as this is evidence that such effects are potentially observable across a broad range of drug molecules (for example, progesterone does not contain a carboxylic acid group unlike most NSAIDs).

Table 7 shows the enthalpies of progesterone (PRO) mixtures (both 10% and 20% by weight) based on the analysis of results obtained. It is seen from Table 7 that the degree of crystallinity of PRO is suppressed in all mixtures with cellulose. The two heated PRO-CLAD samples show the greatest degree of amorphicity for the drug.

TABLE 7

Melting enthalpies of PRO in pure form and in mixtures with CLAD cellulose.

| | $\Delta H_{melt}$ (J/g) | $T_{onset}$ (° C.) | $T_{peak}$ (° C.) | $Crl_{PRO}$ (%) |
|---|---|---|---|---|
| PRO | −108.3 | 127.6 | 130.3 | 100 |
| PRO-CLAD-N 1:9 | −19.1 | 126.3 | 136.4 | 12.9 |
| PRO-CLAD-N 2:8 | −30.2 | 129.0 | 134.3 | 27.8 |
| PRO-CLAD-H 1:9 | −15.2 | 125.8 | 136.4 | 14.0 |
| PRO-CLAD-H 2:8 | −11.5 | 128.9 | 134.0 | 10.6 |

For β-estradiol, the following observations were made:
in DSC profiles, no melting endotherm was observed for heated or normal drug-CLAD mixtures (10 wt % drug) as compared to the pure crystalline drug. In mixtures containing 30 wt % drug, no melting endotherm was observed for the heated mixture, whereas a melting endotherm was evident for the normal mixture;
in XRD profiles, the sharp peaks corresponding to crystalline drug disappear or are essentially depressed for the heated drug-CLAD mixture as compared to the normal drug-CLAD mixture;
in the FTIR profile for progesterone mixtures, alteration of peak positions for C—H vibrations was observed in the heated drug-CLAD mixture as compared to the physical drug-CLAD mixture and pure crystalline drug.

Table 8 shows the enthalpies of β-estradiol (EST) mixtures (10, 20 and 30 wt % drug) based on the analysis of results obtained. It is seen from Table 8 that the degree of crystallinity of EST is suppressed in all mixtures with cellulose. For any given drug:cellulose ratio, the heated EST-CLAD sample showed the greater degree of amorphicity for EST.

TABLE 8

Melting enthalpies of EST in pure form and in mixtures with CLAD cellulose.

| | $\Delta H_{melt}$ (J/g) | $T_{onset}$ (° C.) | $T_{peak}$ (° C.) | $Crl_{EST}$ (%) |
|---|---|---|---|---|
| EST | −136 | 176.6 | 178.1 | 100 |
| EST-CLAD-N 1:9 | −10.1 | 169.7 | 177.2 | 7.4 |
| EST-CLAD-N 2:8 | −1.5 | 175.2 | 185.9 | 1.1 |
| EST-CLAD-N 3:7 | −23.5 | 170.4 | 178.3 | 17.2 |
| EST-CLAD-H 1:9 | 0 | 169.2 | 177.0 | 0 |
| EST-CLAD-H 2:8 | −11.7 | 173.6 | 183.7 | 8.5 |
| EST-CLAD-H 3:7 | −0.9 | 172.3 | 178.4 | 0.7 |

The TGA measurements for β-estradiol are shown in FIG. 14.

Example 5—Flufenamic Acid (FFA) Storage Stability Study

Heated mixtures of FFA and CLAD cellulose were prepared according to the process described in Example 2 containing 10% by weight FFA relative to the FFA-CLAD mixture. Samples were stored in gelatin capsules at 50° C. and 75% relative humidity (RH) for up to 4 months. The samples were analysed by XRD and TGA at various time points according to the methods described in Example 2. The XRD pattern obtained at 4 months is shown in FIG. 15, and the TGA results for before and after storage are shown in FIG. 16.

TGA analysis showed that the degree of crystallinity of FFA was essentially 0% at all time points from 0 to 4 months, and thus remained significantly suppressed throughout the duration of the study.

The XRD analysis also showed minimal evidence of an increase in the crystallinity of the FFA during storage.

The invention claimed is:

1. A pharmaceutical composition comprising cellulose obtained from algae, or a derivative of said cellulose, and an active pharmaceutical ingredient, wherein the active pharmaceutical ingredient is:
   at least 90% by weight amorphous;
   solid under ambient conditions;
   a Type 2 or 4 BCS active pharmaceutical ingredient; and
   a molecule which contains at least one aromatic ring or polycondensed cyclic structure, and the cellulose or derivative thereof is obtained from algae of the Cladophorales or Siphonocladales order.

2. The pharmaceutical composition according to claim 1, wherein the cellulose or derivative thereof is obtained from algae of the genus *Cladophora*.

3. The pharmaceutical composition according to claim 1, wherein the cellulose or derivative thereof is at least 80% crystalline.

4. The pharmaceutical composition according to claim 1, wherein the cellulose or derivative thereof is at least 90% crystalline.

5. The pharmaceutical composition according to claim 1, wherein the composition is formed by a process involving heat-assisted extrusion of a mixture of the cellulose or cellulose derivative and the active pharmaceutical ingredient.

6. The pharmaceutical composition according to claim 1, wherein the weight ratio of the active pharmaceutical ingredient to the cellulose is at most 1:3.

7. The pharmaceutical composition according to claim 1, wherein the active pharmaceutical ingredient is a non-steroidal anti-inflammatory drug, a steroid or a cholate.

8. The pharmaceutical composition according to claim 7, wherein the non-steroidal anti-inflammatory drug, steroid or cholate is selected from the group consisting of ibuprofen, ketoprofen, flurbiprofen, naproxen, aspirin, ethenzamide, mefenamic acid, flufenamic acid, tolfenamic acid, indomethacin, sulindac, pyroxicam, progesterone, estradiol, progestin, estrogen, cholic acid, deoxycholic acid and ursodeoxycholic acid.

9. A pharmaceutical composition comprising cellulose obtained from algae, or a derivative of said cellulose, and an active pharmaceutical ingredient as defined in claim 1, wherein the composition is obtained by a process involving heating a mixture of the active pharmaceutical ingredient and cellulose or cellulose derivative to a temperature close to or above the glass transition temperature of the active pharmaceutical ingredient, wherein the cellulose or derivative thereof is obtained from algae of the Cladophorales or Siphonocladales order.

10. The pharmaceutical composition according to claim 1, wherein the molecule also contains at least one hydrogen bond donor or hydrogen bond acceptor.

11. The pharmaceutical composition according to of claim 1, wherein the cellulose or derivative thereof is obtained from algae of the genus *Cladophora*, and wherein the weight ratio of the active pharmaceutical ingredient to the cellulose is from 1:3 to 1:9.

12. The pharmaceutical composition according to claim 1, wherein the active pharmaceutical agent is a steroid.

13. A method of preparing a pharmaceutical composition comprising mixing together an active pharmaceutical ingredient as defined in claim 1 and cellulose obtained from algae of the Cladophorales or Siphonocladales order, or a derivative of said cellulose.

14. The method of claim 13, further comprising processing the mixture by:
heat-assisted-extrusion;
static heat sealing;
heat-assisted intensive mixing,
mixing under reduced pressure,
heating;
mild grinding which does not adversely affect the pore structure of excipient; and/or
co-spray drying, or rotary evaporation at reduced pressure, with a solvent, preferably wherein the solvent is a mixture of water and lower alkyl alcohol.

15. A method of treating dysmenorrhea or migraine, said method comprising administering a pharmaceutical composition as defined in claim 1 to a subject suffering from dysmenorrhea or migraine, wherein the active pharmaceutical ingredient is a non-steroidal anti-inflammatory drug.

16. The method of claim 11, wherein the weight ratio of the active pharmaceutical ingredient to the cellulose is at most 1:3.

* * * * *